(12) United States Patent
Stangeland et al.

(10) Patent No.: US 8,853,255 B2
(45) Date of Patent: *Oct. 7, 2014

(54) 3-PHENOXYMETHYLPYRROLIDINE COMPOUNDS

(71) Applicants: Eric L. Stangeland, Pacifica, CA (US); Jane Schmidt, San Francisco, CA (US); Daisuke Roland Saito, San Mateo, CA (US); Adam D. Hughes, Belmont, CA (US); Lori Jean Patterson, San Francisco, CA (US)

(72) Inventors: Eric L. Stangeland, Pacifica, CA (US); Jane Schmidt, San Francisco, CA (US); Daisuke Roland Saito, San Mateo, CA (US); Adam D. Hughes, Belmont, CA (US); Lori Jean Patterson, San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/870,134

(22) Filed: Apr. 25, 2013

(65) Prior Publication Data

US 2013/0237581 A1    Sep. 12, 2013

Related U.S. Application Data

(62) Division of application No. 13/588,697, filed on Aug. 17, 2012, now Pat. No. 8,455,665, which is a division of application No. 12/835,944, filed on Jul. 14, 2010, now Pat. No. 8,273,786.

(60) Provisional application No. 61/227,207, filed on Jul. 21, 2009.

(51) Int. Cl.
| | | |
|---|---|---|
| *A01N 43/36* | (2006.01) |
| *A61K 31/40* | (2006.01) |
| *C07D 405/00* | (2006.01) |
| *C07D 207/00* | (2006.01) |
| *C07D 295/22* | (2006.01) |
| *C07D 295/00* | (2006.01) |

(52) U.S. Cl.
USPC ........... 514/422; 514/428; 548/517; 548/400; 548/557; 548/570

(58) Field of Classification Search
USPC ........... 514/422, 428; 548/517, 400, 557, 570
See application file for complete search history.

(56) References Cited

U.S. PATENT DOCUMENTS

| | | | |
|---|---|---|---|
| 3,634,437 A | 1/1972 | Todd |
| 4,229,449 A | 10/1980 | Melloni et al. |
| 4,243,807 A | 1/1981 | Friebe et al. |
| 5,023,269 A | 6/1991 | Robertson et al. |
| 5,037,841 A | 8/1991 | Schohe et al. |
| 5,614,518 A | 3/1997 | Leeson et al. |
| 6,518,284 B2 | 2/2003 | Orjales Venero et al. |
| 7,294,637 B2 | 11/2007 | Aquila et al. |
| 7,317,011 B2 | 1/2008 | Wong et al. |
| 7,378,436 B2 | 5/2008 | Fish et al. |
| 7,384,941 B2 | 6/2008 | Walter et al. |
| 7,888,386 B2 | 2/2011 | Stangeland et al. |
| 7,994,209 B2 | 8/2011 | Stangeland et al. |
| 2002/0151712 A1 | 10/2002 | Lin et al. |
| 2005/0245519 A1 | 11/2005 | Barta et al. |
| 2005/0250775 A1 | 11/2005 | Fish et al. |
| 2007/0015786 A1 | 1/2007 | Allen et al. |
| 2007/0072859 A1 | 3/2007 | Boulet et al. |
| 2007/0265306 A1 | 11/2007 | Orjales Venero et al. |
| 2010/0261762 A1 | 10/2010 | Dreyfus et al. |
| 2010/0267743 A1 | 10/2010 | Stangeland et al. |
| 2011/0257243 A1 | 10/2011 | Stangeland et al. |

FOREIGN PATENT DOCUMENTS

| | | |
|---|---|---|
| WO | WO 2005/000811 A1 | 1/2005 |
| WO | WO 2005/118531 A1 | 12/2005 |
| WO | WO 2007/031828 A2 | 3/2007 |
| WO | WO 2008/023258 A1 | 2/2008 |

OTHER PUBLICATIONS

Fish et al., "Design and synthesis of morpholine derivatives. SAR for dual serotonin & noradrenaline reuptake inhibition", Bioorganic & Medicinal Chemistry Letters, 18, pp. 2562-2566, 2008.

(Continued)

*Primary Examiner* — Uma Ramachandran
(74) *Attorney, Agent, or Firm* — Jeffrey A. Hagenah; Shelley Eberle

(57) ABSTRACT

In one aspect, the invention relates to compounds of formula I:

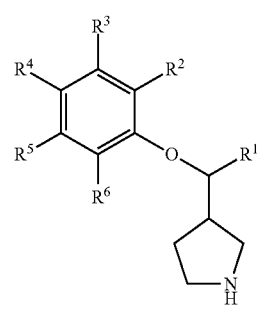

where $R^{1-6}$ are as defined in the specification, or a pharmaceutically acceptable salt thereof. The compounds of formula I are serotonin and norepinephrine reuptake inhibitors. In another aspect, the invention relates to pharmaceutical compositions comprising such compounds; methods of using such compounds; and process and intermediates for preparing such compounds.

10 Claims, No Drawings

(56) References Cited

OTHER PUBLICATIONS

Fish et al., "Derivatives of (3S)-N-(biphenyl-2-ylmethyl)pyrrolidin-3-amine as selective noradrenaline reuptake inhibitors: Reducing P-gp mediated efflux by modulation of H-bond acceptor capacity", Bioorganic & Medicinal Chemistry Letters, 18, pp. 4355-4359, 2008.

Fish et al., "4-Piperidines and 3-pyrrolidines as dual serotonin and noradrenaline reuptake inhibitors: Design, synthesis and structure-activity relationships", Bioorganic & Medicinal Chemistry Letters, 19, pp. 2829-2834, 2009.

Melloni et al., "Potential antidepressant agents. Alpha-aryloxy-benzyl derivatives of ethanolamine and morpholine", European Journal of Medicinal Chemistry, 19(3), pp. 235-242, 1984.

Orjales et al., "Synthesis and binding studies of new [(aryl)(aryloxy)methyl]piperidine derivatives and related compounds as potential antidepressant drugs with high affinity for serotonin (5-HT) and norepinephrine (NE) transporters", Journal of Medicinal Chemistry, 46, pp. 5512-5532, 2003.

International Search Report for PCT/US2010/041901 dated Sep. 28, 2010.

3-PHENOXYMETHYLPYRROLIDINE COMPOUNDS

CROSS-REFERENCE TO RELATED APPLICATIONS

This application is a divisional application of U.S. Ser. No. 13/588,697, filed Aug. 17, 2012, now U.S. Pat. No. 8,455,665, which is a divisional application of U.S. Ser. No. 12/835,944, filed Jul. 14, 2010, now U.S. Pat. No. 8,273,786, which claims the benefit of U.S. Provisional Application No. 61/227,207, filed on Jul. 21, 2009; the entire disclosures of which are incorporated herein by reference.

BACKGROUND OF THE INVENTION

1. Field of the Invention

The present invention relates to 3-phenoxymethylpyrrolidine compounds having activity as serotonin (5-HT) and norepinephrine (NE) reuptake inhibitors. The invention also relates to pharmaceutical compositions comprising such compounds, processes and intermediates for preparing such compounds and methods of using such compounds to treat a pain disorder, such as neuropathic pain, and other ailments.

2. State of the Art

Pain is an unpleasant sensory and emotional experience associated with actual or potential tissue damage, or described in terms of such damage (International Association for the Study of Pain, Pain Terminology). Chronic pain persists beyond acute pain or beyond the expected time for an injury to heal (American Pain Society. "Pain Control in the Primary Care Setting." 2006:15). Neuropathic pain is pain initiated or caused by a primary lesion or dysfunction in the nervous system. Peripheral neuropathic pain occurs when the lesion or dysfunction affects the peripheral nervous system and central neuropathic pain when the lesion or dysfunction affects the central nervous system (IASP).

Several types of therapeutic agents are currently used to treat neuropathic pain including, for example, tricyclic antidepressants (TCAs), serotonin and norepinephrine reuptake inhibitors (SNRIs), calcium channel ligands (e.g., gabapentin and pregabalin), topical lidocaine, and opioid agonists (e.g., morphine, oxycodone, methadone, levorphanol and tramadol). However, neuropathic pain can be very difficult to treat with no more than 40-60% of patients achieving, at best, partial relief of their pain (R. H. Dworkin et al. (2007) *Pain* 132:237-251 at 247). Moreover, all of the therapeutic agents currently used to treat neuropathic pain have various side effects (e.g., nausea, sedation, dizziness and somnolence) that can limit their effectiveness in some patients (Dworkin et al. supra. at 241).

SNRIs, such as duloxetine and venlafaxine, are often used as first line therapy for treating neuropathic pain. These agents inhibit the reuptake of both serotonin (5-hydroxytryptamine, 5-HT) and norepinephrine (NE) by binding to the serotonin and norepinephrine transporters (SERT and NET, respectively). However, both duloxetine and venlafaxine have higher affinity for SERT relative to NET (Vaishnavi et al. (2004) *Biol. Psychiatry* 55(3):320-322).

Preclinical studies suggest that inhibition of both SERT and NET may be necessary for maximally effective treatment of neuropathic and other chronic pain states (Jones et al. (2006) *Neuropharmacology* 51(7-8):1172-1180; Vickers et al. (2008) *Bioorg. Med. Chem. Lett.* 18:3230-3235; Fishbain et al. (2000) *Pain Med.* 1(4):310-316; and Mochizucki (2004) *Human Psychopharmacology* 19:S15-S19). However, in clinical studies, the inhibition of SERT has been reported to be related to nausea and other side effects (Greist et al. (2004) *Clin. Ther.* 26(9):1446-1455). Thus, therapeutic agents having more balanced SERT and NET affinity or slightly higher NET affinity are expected to be particularly useful for treating chronic pain while producing fewer side effects, such as nausea.

Thus, a need exists for novel compounds that are useful for treating chronic pain, such as neuropathic pain. In particular, a need exists for novel compounds that are useful for treating chronic pain and that have reduced side effects, such as nausea. A need also exists for novel dual-acting compounds that inhibit both SERT and NET with high affinity (e.g., $pIC_{50} \geq 8.0$ or $K_i \leq 10$ nM) and balanced inhibition (e.g., a SERT/NET binding $K_i$ ratio of 0.1 to 100).

SUMMARY OF THE INVENTION

The present invention provides novel compounds that have been found to possess serotonin reuptake inhibitory activity and norepinephrine reuptake inhibitory activity. Accordingly, compounds of the invention are expected to be useful and advantageous as therapeutic agents for those diseases and disorders that can be treated by inhibition of the serotonin and/or norepinephrine transporter, such as neuropathic pain.

One aspect of the invention relates to a compound of formula I:

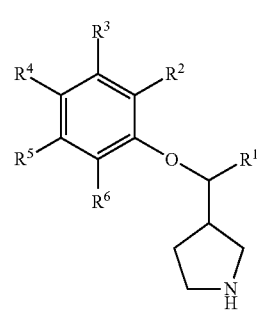

where:

$R^1$ is selected from —$CH_2OH$, —$C_{1-2}$alkylene-S—$C_{1-6}$alkyl, —$C_{1-2}$alkylene-O-phenyl, —$C_{1-2}$alkylene-S-phenyl, —$C_{1-2}$alkylene-O-benzyl, —$C_{1-2}$alkylene-S-benzyl, tetrahydropyranyl, and tetrahydrofuranyl; and $R^2$ through $R^6$ are independently selected from hydrogen, halo, —$C_{1-6}$alkyl, —$CF_3$, —O—$C_{1-6}$alkyl, —CN, —C(O)—$C_{1-6}$alkyl, —S—$C_{1-6}$alkyl, —$C_{1-8}$cycloalkyl, and —$NO_2$; or $R^4$ and $R^5$ are taken together to form —CH=CH—CH=CH—; or $R^5$ and $R^6$ are taken together to form —CH=CH—CH=CH—;

or a pharmaceutically acceptable salt thereof.

Another aspect of the invention relates to compounds of formula I having a configuration selected from:

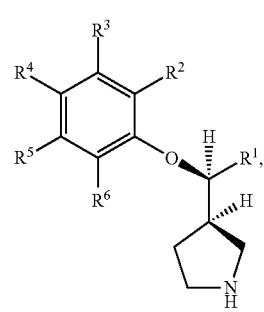

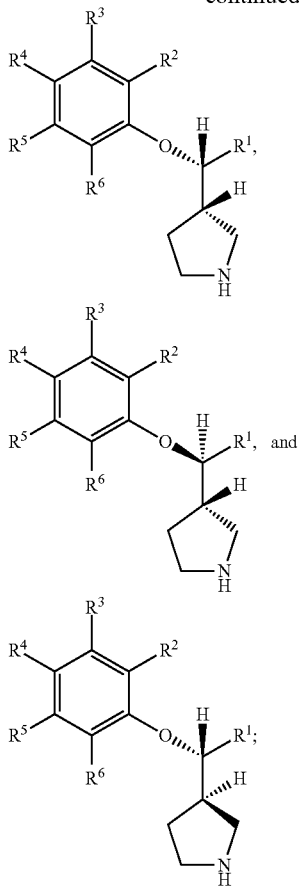

or enriched in a stereoisomeric form having such configuration.

Yet another aspect of the invention relates to pharmaceutical compositions comprising a pharmaceutically acceptable carrier and a compound of the invention. Such compositions may optionally contain other active agents such as anti-Alzheimer's agents, anticonvulsants, antidepressants, anti-Parkinson's agents, dual serotonin-norepinephrine reuptake inhibitors, non-steroidal anti-inflammatory agents, norepinephrine reuptake inhibitors, opioid agonists, selective serotonin reuptake inhibitors, sodium channel blockers, sympatholytics, and combinations thereof. Accordingly, in yet another aspect of the invention, a pharmaceutical composition comprises a compound of the invention, a second active agent, and a pharmaceutically acceptable carrier. Another aspect of the invention relates to a combination of active agents, comprising a compound of the invention and a second active agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of formula I or a pharmaceutically acceptable salt thereof and a first pharmaceutically acceptable carrier; and a second pharmaceutical composition comprising a second active agent and a second pharmaceutically acceptable carrier. The invention also relates to a kit containing such pharmaceutical compositions, for example where the first and second pharmaceutical compositions are separate pharmaceutical compositions.

Compounds of the invention possess serotonin reuptake inhibitory activity and norepinephrine reuptake inhibitory activity, and are therefore expected to be useful as therapeutic agents for treating patients suffering from a disease or disorder that is treated by the inhibition of the serotonin and/or the norepinephrine transporter. Thus, one aspect of the invention relates to a method of treating: a pain disorder such as neuropathic pain; a depressive disorder such as major depression; an affective disorder such as an anxiety disorder; attention deficit hyperactivity disorder; a cognitive disorder such as dementia; stress urinary incontinence; obesity; or vasomotor symptoms associated with menopause, comprising administering to a patient a therapeutically effective amount of a compound of the invention.

Still another aspect of the invention relates to a method for inhibiting serotonin reuptake in a mammal comprising administering to the mammal, a serotonin transporter-inhibiting amount of a compound of the invention. Yet another aspect of the invention relates to a method for inhibiting norepinephrine reuptake in a mammal comprising administering to the mammal, a norepinephrine transporter-inhibiting amount of a compound of the invention. And another aspect of the invention relates to a method for inhibiting serotonin reuptake and norepinephrine reuptake in a mammal comprising administering to the mammal, a serotonin transporter- and norepinephrine transporter-inhibiting amount of a compound of the invention.

Since compounds of the invention possess serotonin reuptake inhibitory activity and norepinephrine reuptake inhibitory activity, such compounds are also useful as research tools. Accordingly, one aspect of the invention relates to a method of using a compound of the invention as a research tool, comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a serotonin reuptake assay and a norepinephrine reuptake assay. Still another aspect of the invention relates to a method of studying a biological system or sample comprising serotonin transporters, norepinephrine transporters, or both, the method comprising: (a) contacting the biological system or sample with a compound of the invention; and (b) determining the effects caused by the compound on the biological system or sample.

The invention also relates to processes and intermediates useful for preparing compounds of the invention. Accordingly, one aspect of the invention relates to a process for preparing compounds of formula I, the process comprising deprotecting a compound of formula XVII:

(XVII)

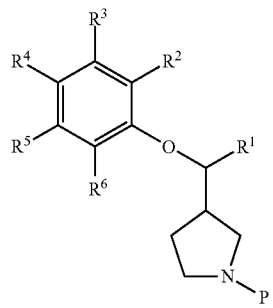

or a salt thereof, where P is an amino-protecting group to provide compounds of formula I, where x and $R^{1-6}$ are as defined for formula I. In other aspects, the invention relates to novel intermediates used in such processes.

Yet another aspect of the invention relates to the use of a compound of the invention for the manufacture of a medicament, especially for the manufacture of a medicament useful for treating pain disorders, depressive disorders, affective disorders, attention deficit hyperactivity disorder, cognitive disorders, stress urinary incontinence, for inhibiting serotonin reuptake in a mammal, or for inhibiting norepinephrine reuptake in a mammal. Still another aspect of the invention relates to the use of a compound of the invention as a research tool. Other aspects and embodiments of the invention are disclosed herein.

DETAILED DESCRIPTION OF THE INVENTION

In one aspect, this invention relates to novel compounds of formula I:

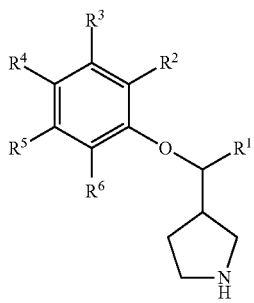

(I)

or a pharmaceutically acceptable salt thereof.

As used herein, the term "compound of the invention" includes all compounds encompassed by formula I such as the species embodied in formula Ia-Id, II-XVII and all other subspecies of such formulas. In addition, when the compound of the invention contain a basic or acidic group (e.g., amino or carboxyl groups), the compound can exist as a free base, free acid, or in various salt forms. All such salt forms are included within the scope of the invention. Accordingly, those skilled in the art will recognize that reference to a compound herein, for example, reference to a "compound of the invention" or a "compound of formula I" includes a compound of formula I as well as pharmaceutically acceptable salts of that compound unless otherwise indicated. Furthermore, solvates of compounds of formula I are included within the scope of this invention.

The compounds of formula I contain at least two chiral centers and therefore, these compounds may be prepared and used in various stereoisomeric forms. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Thus, for example, the terms "compound of formula I," "compounds of formula II," and so forth, are intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual enantiomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original enantiomers. Additionally, where applicable, all cis-trans or E/Z isomers (geometric isomers), tautomeric forms and topoisomeric forms of the compounds of the invention are included within the scope of the invention unless otherwise specified.

More specifically, compounds of formula I contain at least two chiral centers indicated by the symbols * and ** in the following formula:

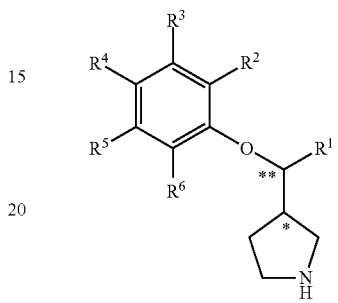

In one stereoisomer, both carbon atoms identified by the * and ** symbols have the (R) configuration. This embodiment of the invention is shown in formula Ia:

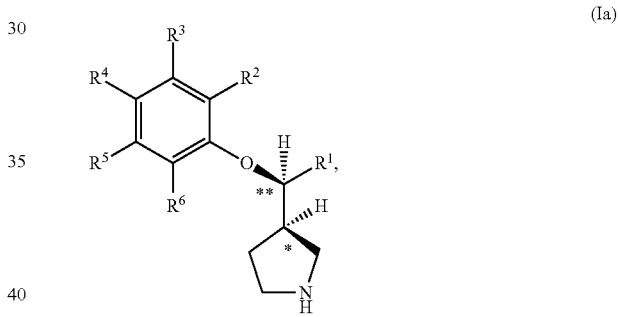

(Ia)

In this embodiment, compounds have the (R,R) configuration at the * and ** carbon atoms or are enriched in a stereoisomeric form having the (R,R) configuration at these carbon atoms.

In another stereoisomer, both carbon atoms identified by the * and ** symbols have the (S) configuration. This embodiment of the invention is shown in formula Ib:

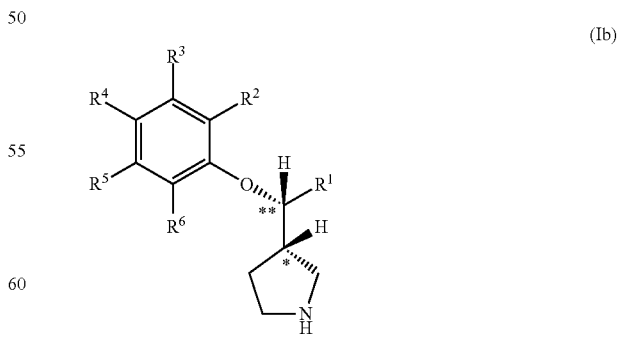

(Ib)

In this embodiment, compounds have the (S,S) configuration at the * and ** carbon atoms or are enriched in a stereoisomeric form having the (S,S) configuration at these carbon atoms.

In yet another stereoisomer, the carbon atom identified by the symbol * has the (S) configuration and the carbon atom identified by the symbol ** has the (R) configuration. This embodiment of the invention is shown in formula Ic:

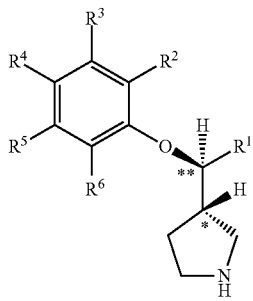

(Ic)

In this embodiment, compounds have the (S,R) configuration at the * and ** carbon atoms or are enriched in a stereoisomeric form having the (S,R) configuration at these carbon atoms.

In still another stereoisomer, the carbon atom identified by the symbol * has the (R) configuration and the carbon atom identified by the symbol ** has the (S) configuration. This embodiment of the invention is shown in formula Id:

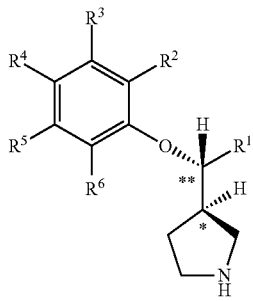

(Id)

In this embodiment, compounds have the (R,S) configuration at the * and ** carbon atoms or are enriched in a stereoisomeric form having the (R,S) configuration at these carbon atoms.

Compounds of formula Ia and Ib are enantiomers and therefore, in separate aspects, this invention relates to each individual enantiomer (i.e., Ia or Ib), a racemic mixture of Ia and Ib, or an enantiomer-enriched mixture of Ia and Ib comprising predominately Ia or predominately Ib. Similarly, compounds of formula Ic and Id are enantiomers and therefore, in separate aspects, this invention relates to each individual enantiomer (i.e., Ic or Id), a racemic mixture of Ic and Id, or a enantiomer-enriched mixture of Ic and Id comprising predominately Ic or predominately Id.

In some embodiments, in order to optimize the therapeutic activity of the compounds of the invention, e.g., to treat neuropathic pain, it may be desirable that the carbon atoms identified by the * and ** symbols have a particular (R,R), (S,S), (S,R), or (R,S) configuration or are enriched in a stereoisomeric form having such configuration. For example, in one embodiment, the compounds of the invention have the (S,R) configuration of formula Ic or are enriched in a stereoisomeric form having the (S,R) configuration, and in another embodiment, the compounds of the invention have the (R,S) configuration of formula Id, or are enriched in a stereoisomeric form having the (R,S) configuration. In other embodiments, the compounds of the invention are present as racemic mixtures, for example as a mixture of enantiomers of formula Ia and Ib, or as a mixture of enantiomers of formula Ic and Id.

This invention also includes isotopically-labeled compounds of formula I, i.e., compounds of formula I where one or more atoms have been replaced or enriched with atoms having the same atomic number but an atomic mass different from the atomic mass that predominates in nature. Examples of isotopes that may be incorporated into a compound of formula I include, but are not limited to, $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{36}Cl$, and $^{18}F$. Of particular interest are compounds of formula I enriched in tritium or carbon-14 which can be used, for example, in tissue distribution studies; compounds of formula I enriched in deuterium especially at a site of metabolism resulting, for example, in compounds having greater metabolic stability; and compounds of formula I enriched in a positron emitting isotope, such as $^{11}C$, $^{18}F$, $^{15}O$ and a $^{13}N$, which can be used, for example, in Positron Emission Topography (PET) studies.

The compounds of the invention have been found to possess serotonin reuptake inhibitory activity and norepinephrine reuptake inhibitory activity. Among other properties, such compounds are expected to be useful as therapeutic agents for treating chronic pain, such as neuropathic pain. By combining dual activity into a single compound, double therapy can be achieved, i.e., serotonin reuptake inhibitory activity and norepinephrine reuptake inhibitory activity, using a single active component. Since pharmaceutical compositions containing one active component are typically easier to formulate than compositions containing two active components, such single-component compositions provide a significant advantage over compositions containing two active components.

Many combined serotonin and norepinephrine reuptake inhibitors (SNRIs) are more selective for SERT than for NET. For example, milnacipran, duloxetine, and venlafaxine and exhibit 2.5-fold, 10-fold, and 100-fold selectivity (measured as $pK_i$) for SERT over NET, respectively. Some, however, are less selective, such as bicifadine, which has a $pK_i$ at SERT of 7.0 and a $pK_i$ at NET of 6.7. Since it may be desirable to avoid selective compounds, in one embodiment of the invention the compounds have a more balanced SERT and NET activity.

The nomenclature used herein to name the compounds of the invention is illustrated in the Examples herein. This nomenclature has been derived using the commercially-available AutoNom software (MDL, San Leandro, Calif.). Compounds of formula I have a 3-phenoxymethylpyrrolidine core. Thus, compounds of formula I where $R^1$ is —CH$_2$—O—C$_{1-6}$alkyl have been named as 3-(1-phenoxy-2-alkoxyethyl)pyrrolidines, and so forth.

REPRESENTATIVE EMBODIMENTS

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, this invention relates to compounds of formula I:

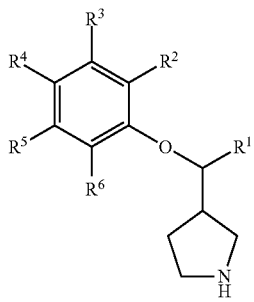

(I)

The $R^1$ moiety is —CH$_2$OH, —C$_{1-2}$alkylene-O—C$_{1-6}$alkyl, —C$_{1-2}$alkylene-S—C$_{1-6}$alkyl, —C$_{1-2}$alkylene-O-phenyl, —C$_{1-2}$alkylene-S-phenyl, —C$_{1-2}$alkylene-O-benzyl, —C$_{1-2}$alkylene-S-benzyl, tetrahydropyranyl, or tetrahydrofuranyl. In one embodiment, $R^1$ is —CH$_2$OH. In another embodiment, $R^1$ is —C$_{1-2}$alkylene-O—C$_{1-6}$alkyl, examples of which include —CH$_2$—O—CH$_3$, —(CH$_2$)$_2$—O—CH$_3$, —CH$_2$—O—CH$_2$CH$_3$, and —CH$_2$—O—CH(CH$_3$)$_2$. In another embodiment, $R^1$ is —C$_{1-2}$alkylene-S—C$_{1-6}$alkyl, examples of which include —(CH$_2$)$_2$—S—CH$_3$. In another embodiment, $R^1$ is —C$_{1-2}$alkylene-O-phenyl, examples of which include —CH$_2$—O-phenyl and —(CH$_2$)$_2$—O-phenyl. In another embodiment, $R^1$ is —C$_{1-2}$alkylene-S-phenyl, examples of which include —CH$_2$—S-phenyl and —(CH$_2$)$_2$—S-phenyl. In another embodiment, $R^1$ is —C$_{1-2}$alkylene-O-benzyl, an example of which includes —CH$_2$—O-benzyl and —(CH$_2$)$_2$—O-benzyl. In another embodiment, $R^4$ is —C$_{1-2}$alkylene-S-benzyl, examples of which include —CH$_2$—S-benzyl. In another embodiment, $R^1$ is tetrahydropyranyl. In still another embodiment, $R^1$ is tetrahydrofuranyl.

The $R^2$ through $R^6$ moieties are independently selected from hydrogen, halo, —C$_{1-6}$alkyl, —CF$_3$, —O—C$_{1-6}$alkyl, —CN, —C(O)—C$_{1-6}$alkyl, —S—C$_{1-6}$alkyl, —C$_{3-8}$cycloalkyl, and —NO$_2$; or $R^4$ and $R^5$ are taken together to form —CH=CH—CH=CH—; or $R^5$ and $R^6$ are taken together to form —CH=CH=CH—CH—.

In some embodiments of the invention, one or more positions on the aryl ring are substituted with a non-hydrogen moiety. For example, one such embodiment may be described by stating that that "$R^5$ is a non-hydrogen moiety". It is understood that this means that $R^5$ can be any of the non-hydrogen moieties defined in formula I, i.e., halo, —C$_{1-6}$alkyl, —CF$_3$, —O—C$_{1-6}$alkyl, —CN, —C(O)—C$_{1-6}$alkyl, —S—C$_{1-6}$alkyl, —CF$_3$, —C$_{3-8}$cycloalkyl, and —NO$_2$; or it is taken together with $R^4$ to form —CH=CH—CH=CH— or taken together with $R^6$ to form —CH—CH=CH—CH—. In one embodiment, at least one of the $R^2$ through $R^6$ groups is a non-hydrogen moiety. In another embodiment, at least two of the $R^2$ through $R^6$ groups are non-hydrogen moieties. In still yet another embodiment, at least three of the $R^2$ through $R^6$ groups are non-hydrogen moieties. In one embodiment, at least four of the $R^2$ through $R^6$ groups are non-hydrogen moieties, and in still another embodiment, all of the $R^2$ through $R^6$ groups are non-hydrogen moieties.

Exemplary halo groups include fluoro, chloro, bromo, and iodo. Exemplary —C$_{1-6}$alkyl groups include —CH$_3$ ("Me"), —CH$_2$CH$_3$ ("Et"), and —CH(CH$_3$)$_2$. Exemplary —O—C$_{1-6}$alkyl groups include —OCH$_3$ ("OMe"), —O—CH$_2$CH$_3$, and —OCH(CH$_3$)$_2$. Exemplary —C(O)—C$_{1-6}$alkyl groups include —C(O)CH$_3$ and —C(O)CH$_2$CH$_3$. Exemplary —S—C$_{1-6}$alkyl groups include —SCH$_3$. Exemplary —C$_{3-8}$cycloalkyl groups include cyclohexyl.

In one embodiment, $R^1$ is —CH$_2$OH, which is depicted as formula II:

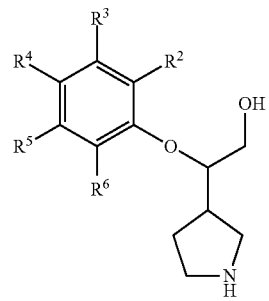

(II)

where $R^2$-$R^6$ are as defined for formula I. In another embodiment, $R^1$ is —C$_{1-2}$alkylene-O—C$_{1-6}$alkyl, which is depicted as formula III:

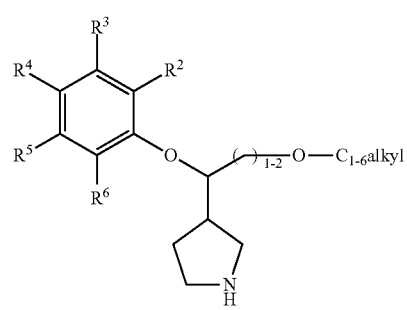

(III)

where $R^2$-$R^6$ are as defined for formula I. In still another embodiment, $R^1$ is —C$_{1-2}$alkylene-S—C$_{1-6}$alkyl which is depicted as formula IV:

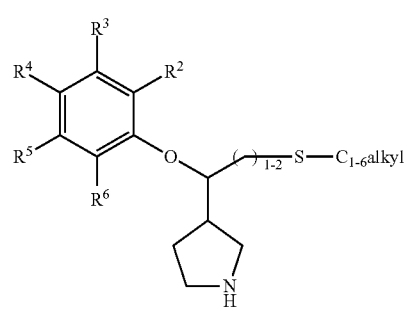

(IV)

where $R^2$-$R^6$ are as defined for formula I. In another embodiment, $R^1$ is —C$_{1-2}$alkylene-O-phenyl which is depicted as formula V:

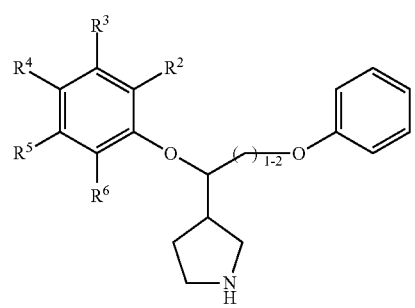

(V)

where $R^2$-$R^6$ are as defined for formula I. In another embodiment, $R^1$ is —$C_{1-2}$alkylene-S-phenyl, which is depicted as formula VI:

(VI)

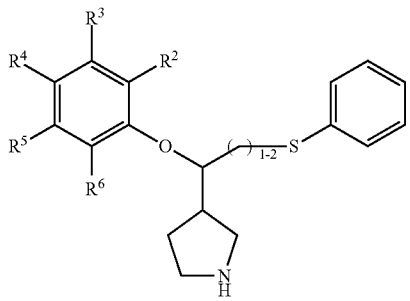

where $R^2$-$R^6$ are as defined for formula I. In another embodiment, $R^1$ is —$C_{1-2}$alkylene-O-benzyl which is depicted as formula VII:

(VII)

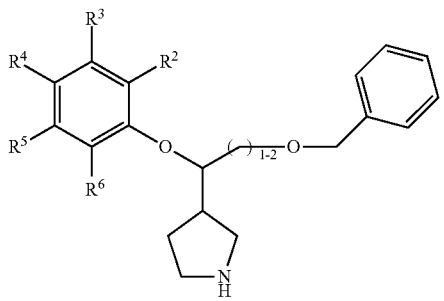

where $R^2$-$R^6$ are as defined for formula I. In another embodiment, $R^1$ is —$C_{1-2}$alkylene-S-benzyl which is depicted as formula VIII:

(VIII)

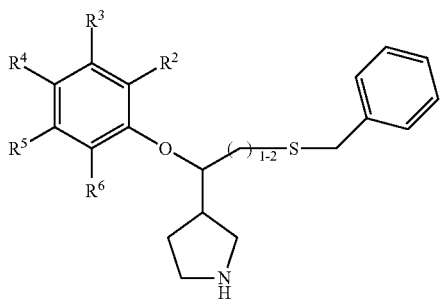

where $R^2$-$R^6$ are as defined for formula I. In one embodiment, $R^1$ is —$C_{1-2}$alkylene-tetrahydropyranyl, where tetrahydropyranyl has the formula:

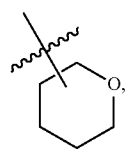

and is bonded to any available point of attachment, and includes:

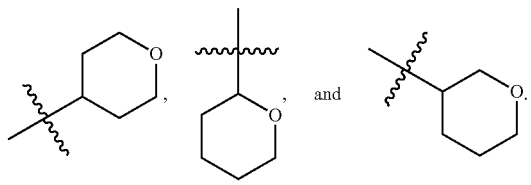

Once exemplary embodiment is depicted as formula IX:

(IX)

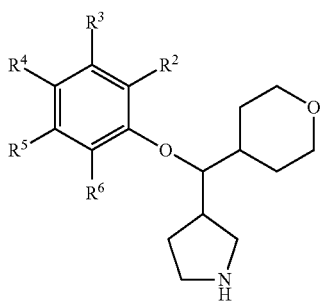

where $R^2$-$R^6$ are as defined for formula I. In yet another embodiment, $R^1$ is —$C_{1-2}$alkylene-tetrahydrofuranyl, where tetrahydrofuranyl has the formula:

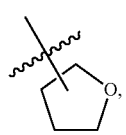

which is bonded to any available point of attachment and includes:

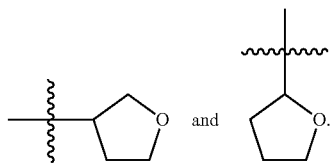 [SMILES: *C1CCOC1 ; "and" ; *C1CCCO1]

One exemplary embodiment is depicted as formula X:

(X)

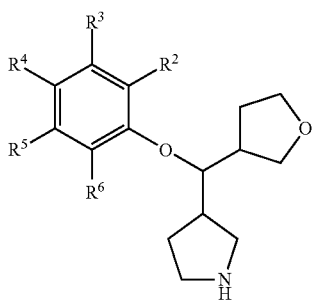

where $R^2$-$R^6$ are as defined for formula I.

In one particular embodiment, $R^2$ and $R^3$ are non-hydrogen moieties, while $R^4$, $R^5$, and $R^6$ are hydrogen, which is depicted as formula XI:

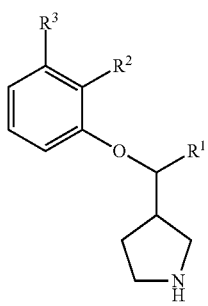

(XI)

where $R^1$ is as defined for formula I.

In one particular embodiment, $R^2$ and $R^4$ are non-hydrogen moieties, while $R^3$, $R^5$, and $R^6$ are hydrogen, which is depicted as formula XII:

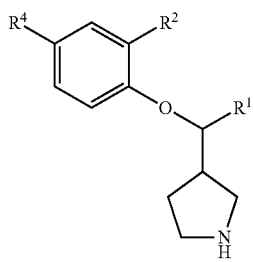

(XII)

where $R^1$ is as defined for formula I.

In one particular embodiment, $R^3$ and $R^4$ are non-hydrogen moieties, while $R^2$, $R^5$, and $R^6$ are hydrogen, which is depicted as formula XIII:

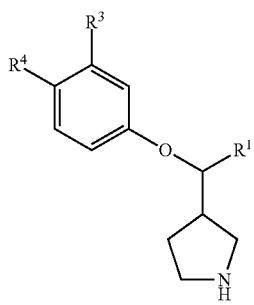

(XIII)

where $R^1$ is as defined for formula I.

In one particular embodiment, $R^2$, $R^3$, and $R^4$ are non-hydrogen moieties, while $R^5$ and $R^6$ are hydrogen, which is depicted as formula IX:

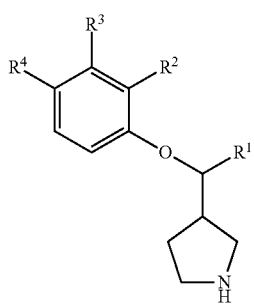

(XIV)

where $R^1$ is as defined for formula I.

In one particular embodiment, $R^2$, $R^4$, and $R^6$ are non-hydrogen moieties, while $R^3$ and $R^5$ are hydrogen, which is depicted as formula XV:

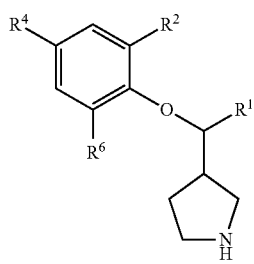

(XV)

where $R^1$ is as defined for formula I.

In one embodiment, $R^2$ is hydrogen, halo, —$C_{1-6}$alkyl, or —$CF_3$; in another aspect, this embodiment has formulas II-XV. In another embodiment, $R^2$ is hydrogen, fluoro, chloro, —$CH_3$, or —$CF_3$; in another aspect, this embodiment has formulas II-XV.

In one embodiment, $R^3$ is hydrogen, halo, or —$CF_3$; in another aspect, this embodiment has formulas II-XV. In another embodiment, $R^3$ is hydrogen, fluoro, chloro, or —$CF_3$; in another aspect, this embodiment has formulas II-XV.

In one embodiment, $R^4$ is hydrogen, halo, —$C_{1-6}$alkyl, —$CF_3$, or —CN; in another aspect, this embodiment has formulas II-XV. In another embodiment, $R^4$ is hydrogen, fluoro, chloro, —$CH_3$, —$CF_3$, or —CN; in another aspect, this embodiment has formulas II-XV.

In one embodiment, $R^5$ is hydrogen or halo; in another aspect, this embodiment has formulas II-XV. In another embodiment, $R^5$ is hydrogen or chloro; in another aspect, this embodiment has formulas II-XV.

In one embodiment, $R^6$ is hydrogen or halo; in another aspect, this embodiment has formulas II-XV. In another embodiment, $R^6$ is hydrogen, fluoro, or chloro; in another aspect, this embodiment has formulas II-XV.

In yet another embodiment, $R^4$ and $R^5$ are taken together to form —CH=CH—CH=CH— or $R^5$ and $R^6$ are taken together to form —CH=CH—CH=CH—, which is depicted as formula XVIa and XVIb, respectfully:

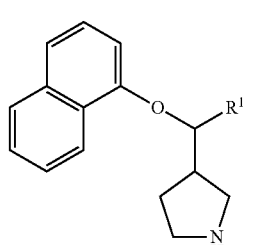

(XVIa)

and

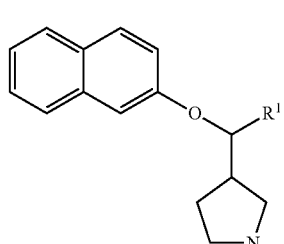

(XVIb)

where $R^1$ is as defined for formula I.

In addition, particular compounds of formula I that are of interest include those set forth in the Examples below, as well a pharmaceutically acceptable salt thereof.

DEFINITIONS

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, and an acidic moiety such as a carboxylic acid, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The term "solvate" means a complex or aggregate formed by one or more molecules of a solute, e.g., a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need thereof, i.e., the amount of drug needed to obtain the desired therapeutic effect. For example, a therapeutically effective amount for treating neuropathic pain is an amount of compound needed to, for example, reduce, suppress, eliminate or prevent the symptoms of neuropathic pain or to treat the underlying cause of neuropathic pain. On the other hand, the term "effective amount" means an amount sufficient to obtain a desired result, which may not necessary be a therapeutic result. For example, when studying a system comprising a norepinephrine transporter, an "effective amount" may be the amount needed to inhibit norepinephrine reuptake.

The term "treating" or "treatment" as used herein means the treating or treatment of a disease or medical condition (such as neuropathic pain) in a patient, such as a mammal (particularly a human), that includes one or more of the following: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating neuropathic pain" would include preventing neuropathic pain from occurring, ameliorating neuropathic pain, suppressing neuropathic pain, and alleviating the symptoms of neuropathic pain. The term "patient" is intended to include those mammals, such as humans, that are in need of treatment or disease prevention, that are presently being treated for disease prevention or treatment of a specific disease or medical condition, as well as test subjects in which compounds of the invention are being evaluated or being used in a assay, for example an animal model.

The term "alkyl" means a monovalent saturated hydrocarbon group which may be linear or branched. Unless otherwise defined, such alkyl groups typically contain from 1 to 10 carbon atoms and include, for example, —$C_{1-2}$ alkyl, —$C_{1-3}$ alkyl, —$C_{1-4}$ alkyl, —$C_{1-6}$alkyl, and —$C_{2-6}$alkyl. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. The term "alkylene" means a divalent saturated hydrocarbon group that may be linear or branched.

The term "cycloalkyl" means a monovalent saturated carbocyclic hydrocarbon group. Unless otherwise defined, such cycloalkyl groups typically contain from 3 to 10 carbon atoms and include, for example, —$C_{3-5}$cycloalkyl, —$C_{3-6}$cycloalkyl and —$C_{3-8}$cycloalkyl. Representative cycloalkyl groups include, by way of example, cyclopropyl, cyclobutyl, cyclopentyl, cyclohexyl and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, and the term "—$C_{3-8}$cycloalkyl" means a cycloalkyl group having from 3 to 8 carbon atoms, where the carbon atoms are in any acceptable configuration.

The term "halo" means fluoro, chloro, bromo and iodo.

All other terms used herein are intended to have their ordinary meaning as understood by those of ordinary skill in the art to which they pertain.

General Synthetic Procedures

Compounds of the invention can be prepared from readily available starting materials using the following general methods, the procedures set forth in the Examples, or by using other methods, reagents, and starting materials that are known to those skilled in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (i.e., reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in Greene and Wuts, *Protecting Groups in Organic Synthesis*, Third Edition, Wiley, New York, 1999, and references cited therein.

More particularly, in the schemes below, P represents an "amino-protecting group," a term used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, and the like. Standard deprotection techniques and reagents such as TFA in DCM or HCl in 1,4-dioxane, methanol, or ethanol, are used to remove protecting groups, when present. For example, a BOC group can be removed using an acidic reagent such as hydrochloric acid, trifluoroacetic acid and the like; while a Cbz group can be removed by employing catalytic hydrogenation conditions such as $H_2$ (1 atm), 10% Pd/C in an alcoholic solvent.

Suitable inert diluents or solvents for use in these schemes include, by way of illustration and not limitation, tetrahydrofuran (THF), acetonitrile, N,N-dimethylformamide (DMF), dimethylsulfoxide (DMSO), toluene, dichloromethane (DCM), chloroform ($CHCl_3$), and the like.

All reactions are typically conducted at a temperature within the range of about −78° C. to 110° C., for example at room temperature. Reactions may be monitored by use of thin layer chromatography (TLC), high performance liquid chromatography (HPLC), and/or LCMS until completion. Reactions may be complete in minutes, may take hours, typically from 1-2 hours and up to 48 hours, or days, such as up to 3-4 days. Upon completion, the resulting mixture or reaction product may be further treated in order to obtain the desired product. For example, the resulting mixture or reaction product may be subjected to one or more of the following procedures: dilution (for example with saturated $NaHCO_3$); extraction (for example, with ethyl acetate, $CHCl_3$, DCM, aqueous HCl); washing (for example, with DCM, saturated aqueous NaCl, or saturated aqueous $NaHCO_3$); drying (for example, over $MgSO_4$ or $Na_2SO_4$, or in vacuo); filtration; being concentrated (for example, in vacuo); being redissolved (for example in a 1:1 acetic acid:$H_2O$ solution); and/or purification (for example by preparative HPLC, reverse phase preparative HPLC, or crystallization).

By way of illustration, compounds of formula I, as well as their salts, can be prepared by the following schemes, as well as by the procedures set forth in the examples. The * chiral center is known to be S or R, and is depicted accordingly. However, the ** chiral center is not known unambiguously and was designated R or S based upon the first elution peak by reverse phase HPLC from the mixture of diastereomeric intermediates (the protected alcohols). Assignment of the stereochemistry of such chiral secondary alcohols can be accomplished utilizing the established Mosher ester analysis (see, for example, Dale and Mosher (1969) *J. Org. Chem.* 34(9):2543-2549). For those compounds where $R^1$ is —$CH_2OH$, —$C_{1-2}$alkylene-O—$C_{1-6}$alkyl, —$C_{1-2}$alkylene-S—$C_{1-6}$alkyl, —$C_{1-2}$alkylene-O-phenyl, —$C_{1-2}$alkylene-S-phenyl, —$C_{1-2}$alkylene-O-benzyl, or —$C_{1-2}$alkylene-5-benzyl, the following applies: for compounds where the * chiral center was known to be S, then the first eluting peak was designated R at the  chiral center and the second eluting peak was designated S at the  chiral center; and for compounds where the * chiral center was known to be R, then the first eluting peak was designated S at the  chiral center and the second eluting peak was designated R at the  chiral center. For those compounds where $R^1$ is tetrahydropyranyl, the following applies: for compounds where the * chiral center was known to be S, then the first eluting peak was designated S at the  chiral center and the second eluting peak was designated R at the  chiral center; and for compounds where the * chiral center was known to be R, then the first eluting peak was designated R at the  chiral center and the second eluting peak was designated S at the  chiral center.

While the following schemes illustrate formation of one particular stereoisomer, the other stereoisomers can be made in a similar manner by using a starting material having different stereochemistry.

Scheme I

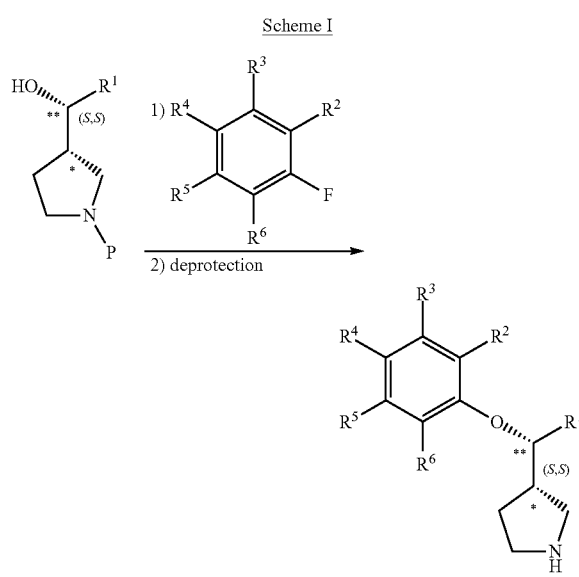

Compounds of formula I can be prepared by reacting the appropriate alcohol starting material and the desired optionally substituted fluorobenzene using a nucleophilic aromatic substitution reaction ($S_NAr$). This reaction is typically conducted using sodium hydride (NaH) in a solvent such as DMF. Deprotection then yields the desired compound of formula I.

Scheme II

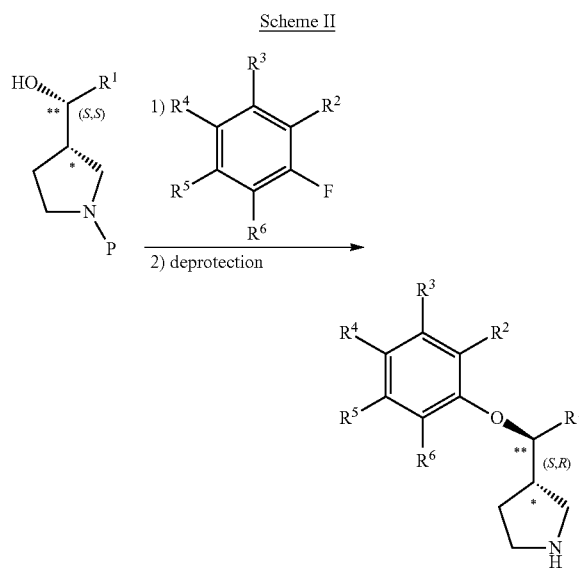

Compounds of formula I can also be prepared using the Mitsunobu coupling reaction (Mitsunobu and Yamada (1967) *M. Bull. Chem. Soc. JPN.* 40:2380-2382) of the alcohol starting material and optionally substituted phenol. This reaction is typically conducted using standard Mitsunobu coupling conditions, using a redox system containing an azodicarboxylate such as diethyl azodicarboxylate or diisopropyl azodicarboxylate and a phosphine catalyst such as triphenylphosphine. Deprotection then yields the desired compound of formula I.

The alcohol starting material can also be prepared by olefination of the aldehyde by a Wittig reaction, followed by epoxidation of the alkene using an oxygen transfer catalyst such as methyltrioxorhenium(VII) and hydrogen peroxide as the terminal oxidant. The diastereoisomers are then separated by Jacobsen kinetic resolution to give the epoxide as a single isomer.

Scheme III

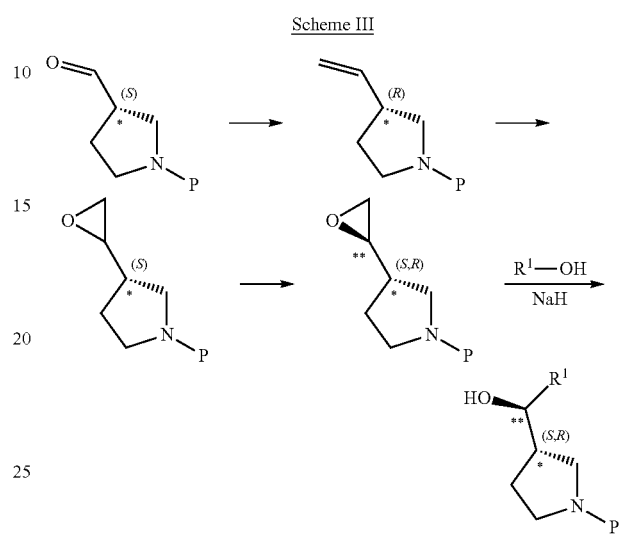

The next step involves opening the epoxide with an alkoxide, and is typically conducted using NaH. Examples of suitable alcohols include ethanol ($R^1$ is $—CH_2—OCH_2CH_3$) and isopropyl alcohol ($R^1$ is $—CH_2—OCH(CH_3)_2$). The (R,S) alcohol starting material can be prepared in a similar manner using the (R) aldehyde starting material.

The alcohol starting material can also be prepared by the 2,2,6,6-tetramethyl-1-piperidinyloxy, free radical (TEMPO) mediated oxidation of (R)-3-hydroxymethylpyrrolidine-1-carboxylic acid t-butyl ester to yield (R)-3-formylpyrrolidine-1-carboxylic acid t-butyl ester.

Scheme IV

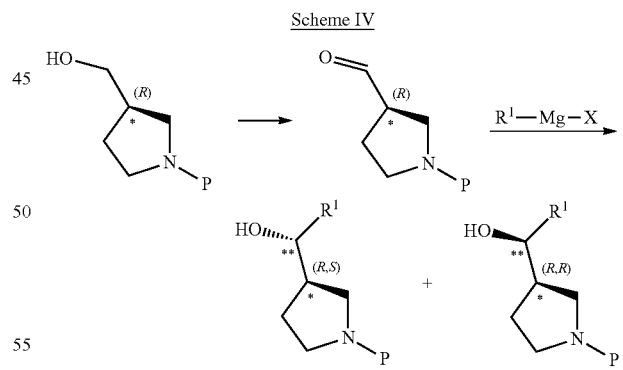

This method is particularly useful by minimizing the amount of racemization that can occur during oxidation. 3-Hydroxymethylpyrrolidine-1-carboxylic acid t-butyl ester, where P is Boc or benzyl, is commercially available. Alternately, (R)-3-hydroxymethylpyrrolidine-1-carboxylic acid t-butyl ester can be oxidized using any oxidizing agent suitable for converting a primary alcohol into an aldehyde. Representative oxidizing agents include, for example, dimethyl sulfoxide, Collin's reagent, Corey's reagent, pyridinium dichromate and the like. The next step involves a Grignard reaction between the formyl compound and the Grignard reagent, $R^1$—MgX, where X is chloro or bromo, for example. The step is typically conducted using standard Grignard reaction conditions. Exemplary Grignard reagents include 4-tetrahydropyranmagnesium chloride ($R^1$ is tetrahydropyranyl), and the like. The (S,R) and (S,S) alcohol starting materials can be prepared in a similar manner using (S)—Boc-3-pyrrolidinemethanol, also known as (S)-3-hydroxymethylpyrrolidine-1-carboxylic acid t-butyl ester.

The alcohol starting material can also be prepared by the acylation of pyrrolidinones, using a non-nucleophilic strong base such as lithium diisopropylamide (LDA), followed by a borane reduction to form the alcohol. Suitable reduction reagents include borane dimethyl sulfide complex ($BH_3.Me_2S$), 9-borabicyclo[3.3.1]nonane, borane 1,2-bis(t-butylthio)ethane complex, borane t-butylamine complex, borane di(t-butyl)phosphine complex, borane-tetrahydrofuran complex ($BH_3.THF$) and so forth.

Scheme V

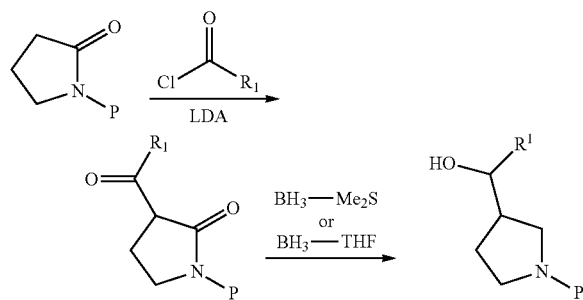

Exemplary acid chloride reagents include 3-methoxypropionyl chloride ($R^1$ is —$CH_2$)$OCH_3$) and 3-methylthiopropionyl chloride ($R^1$ is —($CH_2$)$SCH_3$).

If desired, pharmaceutically acceptable salts of the compounds of formula I can be prepared by contacting the free acid or base form of a compound of formula I with a pharmaceutically acceptable base or acid.

Certain of the intermediates described herein are believed to be novel and accordingly, such compounds are provided as further aspects of the invention including, for example, compounds of formula XVII:

(XVII)

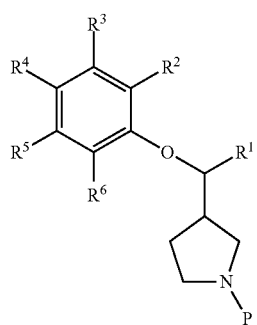

or a salt thereof, where P represents an amino-protecting group, particularly t-butoxycarbonyl (BOC) where $R^1$ and $R^{2-6}$ are as defined for formula I. In one embodiment of the invention, compounds of the invention can be prepared by deprotecting compounds of formula V to provide compounds of formula I, or a pharmaceutically acceptable salt thereof.

Further details regarding specific reaction conditions and other procedures for preparing representative compounds of the invention or intermediates thereof are described in the Examples set forth herein.

Utility

Compounds of the invention possess serotonin and norepinephrine reuptake inhibitory activity. Thus, these compounds have therapeutic utility as combined serotonin and norepinephrine reuptake inhibitors (SNRIs). In one embodiment, compounds of the invention possess equal or approximately equal serotonin reuptake inhibitory activity and norepinephrine reuptake inhibitory activity.

The inhibition constant ($K_i$) of a compound is the concentration of ligand in a radioligand binding inhibition assay that would occupy 50% of the transporters if no radioligand were present. $K_i$ values can be determined from radioligand binding studies with $^3$H-nisoxetine (for the norepinephrine transporter, NET) and $^3$H-citalopram (for the serotonin transporter, SERT), as described in Assay 1. These $K_i$ values are derived from $IC_{50}$ values in the binding assay using the Cheng-Prusoff equation and the $K_d$ of the radioligand (Cheng & Prusoff (1973) *Biochem. Pharmacol.* 22(23):3099-3108). Functional $IC_{50}$ values can be determined in the functional inhibition of uptake assays described in Assay 2. These $IC_{50}$ values can be converted to $K_i$ values using the Cheng-Prusoff equation and the $K_m$ of the transmitter for the transporter. It is noted however, that the uptake assay conditions described in Assay 2 are such that the $IC_{50}$ values are very close to the $K_i$ values, should a mathematical conversion be desired, since the neurotransmitter concentration (5-HT, NE, or DA) used in the assay is well below its $K_m$ for the respective transporter. In one embodiment, compounds of the invention exhibit a SERT $K_i$/NET $K_i$ in the range of 0.1 to 100; in another embodiment, a SERT $K_i$/NET $K_i$ in the range of 0.3 to 100; and in still another embodiment, exhibit a SERT $K_i$/NET $K_i$ in the range of 0.3 to 10.

Another measure of serotonin and norepinephrine reuptake inhibition is the $pIC_{50}$ value. In one embodiment, compounds of the invention have serotonin and norepinephrine reuptake inhibition $pIC_{50}$ values ≥7; in another embodiment, compounds of the invention have a serotonin reuptake inhibition $pIC_{50} \geq 7$ and a norepinephrine reuptake inhibition $pIC_{50} \geq 8$; in yet another embodiment, compounds of the invention have a serotonin reuptake inhibition $pIC_{50} \geq 8$ and a norepinephrine reuptake inhibition $pIC_{50} \geq 7$; and in another embodiment, compounds of the invention have serotonin and norepinephrine reuptake inhibition $pIC_{50}$ values ≥8. In one particular embodiment, such compounds have formula II-XVI.

In another embodiment, compounds of the invention are selective for inhibition of SERT and NET over the dopamine transporter (DAT). For example in this embodiment, compounds of particular interest are those that exhibit a binding affinity for SERT and NET that is at least 5 times higher than the binding affinity for DAT, or that is at least 10 times higher than for DAT, or at least 20 or 30 times higher than for DAT. In another embodiment, the compounds do not exhibit significant DAT inhibition. In still another embodiment, the compounds exhibit less than 50% inhibition of DAT activity when measured at a concentration of 794 nM. Under the assay conditions used, a compound which exhibits ≤50% inhibition would have an estimated $pK_i$ value at DAT of ≤6.1.

In still another embodiment, compounds of the invention possess dopamine reuptake inhibitory activity as well as serotonin and norepinephrine reuptake inhibitory activity. For example in this embodiment, compounds of particular interest are those that exhibit a pIC$_{50}$ at SERT and NET greater than or equal to 8.0, and a pIC$_{50}$ at DAT greater than or equal to 7.0.

It is noted that in some cases, compounds of the invention may possess either weak serotonin reuptake inhibitory activity or weak norepinephrine reuptake inhibitory activity. In these cases, those of ordinary skill in the art will recognize that such compounds still have utility as primarily either a NET inhibitor or a SERT inhibitor, respectively, or will have utility as research tools.

Exemplary assays to determine the serotonin and/or norepinephrine reuptake inhibiting activity of compounds of the invention include by way of illustration and not limitation, assays that measure SERT and NET binding, for example, as described in Assay 1 and in Tsuruda et al. (2010) *Journal of Pharmacological and Toxicological Methods* 61(2):192-204. In addition, it is useful to understand the level of DAT binding and uptake in an assay such as that described in Assay 1. Useful secondary assays include neurotransmitter uptake assays to measure inhibition of serotonin and norepinephrine uptake into cells expressing the respective human or rat recombinant transporter (hSERT, hNET, or hDAT) as described in Assay 2, and ex vivo radioligand binding and neurotransmitter uptake assays that are used to determine the in vivo occupancy of SERT, NET and DAT in tissue as described in Assay 3. Other assays that are useful to evaluate pharmacological properties of test compounds include those listed in Assay 4. Exemplary in vivo assays include the formalin paw test described in Assay 5, which is a reliable predictor of clinical efficacy for the treatment of neuropathic pain, and the spinal nerve ligation model described in Assay 6. The aforementioned assays are useful in determining the therapeutic utility, for example, the neuropathic pain relieving activity, of compounds of the invention. Other properties and utilities of compounds of the invention can be demonstrated using various in vitro and in vivo assays well-known to those skilled in the art.

Compounds of the invention are expected to be useful for the treatment and/or prevention of medical conditions in which the regulation of monoamine transporter function is implicated, in particular those conditions mediated by or responsive to the inhibition of serotonin and norepinephrine reuptake. Thus it is expected that patients suffering from a disease or disorder that is treated by the inhibition of the serotonin and/or the norepinephrine transporter can be treated by administering a therapeutically effective amount of a serotonin and norepinephrine reuptake inhibitor of the invention. Such medical conditions include, by way of example, pain disorders such as neuropathic pain, fibromyalgia, and chronic pain, depressive disorders such as major depression, affective disorders such as an anxiety disorder, attention deficit hyperactivity disorder, cognitive disorders such as dementia, and stress urinary incontinence.

The amount of active agent administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the active agent and any secondary agents being administered, and the like. Treatment of a patient suffering from a disease or medical condition (such as neuropathic pain) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating neuropathic pain, a measure of the effectiveness of treatment may involve assessment of the patient's quality of life, e.g., improvements in the patient's sleeping patterns, work attendance, ability to exercise and be ambulatory, etc. Pain scales, operating on a point basis, may also be used to help evaluate a patient's pain level. Indicators for the other diseases and conditions described herein, are well-known to those skilled in the art, and are readily available to the treating physician. Continuous monitoring by the physician will ensure that the optimal amount of active agent will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Pain Disorders

SNRIs have been shown to have a beneficial effect on pain such as painful diabetic neuropathy (duloxetine, Goldstein et al. (2005) *Pain* 116:109-118; venlafaxine, Rowbotham et al. (2004) *Pain* 110:697-706), fibromyalgia (duloxetine, Russell et al. (2008) *Pain* 136(3):432-444; milnacipran, Vitton et al. (2004) *Human Psychopharmacology* 19:S27-S35), and migraine (venlafaxine, Ozyalcin et al. (2005) *Headache* 45(2):144-152). Thus, one embodiment of the invention relates to a method for treating a pain disorder, comprising administering to a patient a therapeutically effective amount of a compound of the invention. Typically, the therapeutically effective amount will be the amount that is sufficient to relieve the pain. Exemplary pain disorders include, by way of illustration, acute pain, persistent pain, chronic pain, inflammatory pain, and neuropathic pain. More specifically, these include pain associated with or caused by: arthritis; back pain including chronic low back pain; cancer, including tumor related pain (e.g., bone pain, headache, facial pain or visceral pain) and pain associated with cancer therapy (e.g., post-chemotherapy syndrome, chronic post-surgical pain syndrome and post-radiation syndrome); carpal tunnel syndrome; fibromyalgia; headaches including chronic tension headaches; inflammation associated with polymyalgia, rheumatoid arthritis and osteoarthritis; migraine; neuropathic pain including complex regional pain syndrome; overall pain; post-operative pain; shoulder pain; central pain syndromes, including post-stroke pain, and pain associated with spinal cord injuries and multiple sclerosis; phantom limb pain; pain associated with Parkinson's disease; and visceral pain (e.g., irritable bowel syndrome). Of particular interest is the treatment of neuropathic pain, which includes diabetic peripheral neuropathy (DPN), HIV-related neuropathy, post-herpetic neuralgia (PHN), and chemotherapy-induced peripheral neuropathy. When used to treat pain disorders such as neuropathic pain, compounds of the invention may be administered in combination with other therapeutic agents, including anticonvulsants, antidepressants, muscle relaxants, NSAIDs, opioid agonists, selective serotonin reuptake inhibitors, sodium channel blockers, and sympatholytics. Exemplary compounds within these classes are described herein.

Depressive Disorders

Another embodiment of the invention relates to a method of treating a depressive disorder, comprising administering to a patient a therapeutically effective amount of a compound of the invention. Typically, the therapeutically effective amount will be the amount that is sufficient to alleviate depression and provide a sense of general well-being. Exemplary depressive disorders include, by way of illustration and not limitation: depression associated with Alzheimer's disease, bipolar disorder, cancer, child abuse, infertility, Parkinson's disease, postmyocardial infarction, and psychosis; dysthymia; grumpy or irritable old man syndrome; induced depression; major depression; pediatric depression; postmenopausal depression; post partum depression; recurrent depression; single episode depression; and subsyndromal symptomatic depression. Of particular interest is the treatment of major depression. When used to treat depressive disorders, compounds of the invention may be administered in combination with other therapeutic agents, including antidepressants and dual serotonin-norepinephrine reuptake inhibitors. Exemplary compounds within these classes are described herein.

Affective Disorders

Another embodiment of the invention relates to a method of treating an affective disorder, comprising administering to a patient a therapeutically effective amount of a compound of the invention. Exemplary affective disorders include, by way of illustration and not limitation: anxiety disorders such as general anxiety disorder; avoidant personality disorder; eating disorders such as anorexia nervosa, bulimia nervosa and obesity; obsessive compulsive disorder; panic disorder; personality disorders such as avoidant personality disorder and attention deficit hyperactivity disorder (ADHD); post-traumatic stress syndrome; phobias such as agoraphobia, as well as simple and other specific phobias, and social phobia; premenstrual syndrome; psychotic disorders, such as schizophrenia and mania; seasonal affective disorder; sexual dysfunction, including premature ejaculation, male impotence, and female sexual dysfunction such as female sexual arousal disorder; social anxiety disorder; and substance abuse disorders, including chemical dependencies such as addictions to alcohol, benzodiazepines, cocaine, heroin, nicotine and phenobarbital, as well as withdrawal syndromes that may arise from these dependencies. When used to treat affective disorders, compounds of the invention may be administered in combination with other therapeutic agents, including antidepressants. Exemplary compounds within these classes are described herein.

Atomoxetine, which is 10-fold NET selective, is approved for attention deficit hyperactivity disorder (ADHD) therapy, and clinical studies have shown that the SNRI, venlafaxine, can also have a beneficial effect in treating ADHD (Mukaddes et al. (2002) Eur. Neuropsychopharm. 12(Supp 3):421). Thus, the compounds of the invention are also expected to be useful in methods for treating attention deficit hyperactivity disorder by administering to a patient a therapeutically effective amount of a compound of the invention. When used to treat depression, compounds of the invention may be administered in combination with other therapeutic agents, including antidepressants. Exemplary compounds within these classes are described herein.

Cognitive Disorders

Another embodiment of the invention relates to a method of treating a cognitive disorder, comprising administering to a patient a therapeutically effective amount of a compound of the invention. Exemplary cognitive disorders include, by way of illustration and not limitation: dementia, which includes degenerative dementia (e.g., Alzheimer's disease, Creutzfeldt-Jakob disease, Huntingdon's chorea, Parkinson's disease, Pick's disease, and senile dementia), vascular dementia (e.g., multi-infarct dementia), and dementia associated with intracranial space occupying lesions, trauma, infections and related conditions (including HIV infection), metabolism, toxins, anoxia and vitamin deficiency; and mild cognitive impairment associated with ageing, such as age associated memory impairment, amnesiac disorder and age-related cognitive decline. When used to treat cognitive disorders, compounds of the invention may be administered in combination with other therapeutic agents, including anti-Alzheimer's agents and anti-Parkinson's agents. Exemplary compounds within these classes are described herein.

Other Disorders

SNRIs have also been shown to be effective for the treatment of stress urinary incontinence (Dmochowski (2003) Journal of Urology 170(4): 1259-1263). Thus, another embodiment of the invention relates to a method for treating stress urinary incontinence, comprising administering to a patient a therapeutically effective amount of a compound of the invention. When used to treat stress urinary incontinence, compounds of the invention may be administered in combination with other therapeutic agents, including anticonvulsants. Exemplary compounds within these classes are described herein.

Duloxetine, an SNRI, is undergoing clinical trials for evaluating its efficacy in treating chronic fatigue syndrome, and has recently been shown to be effective in treating fibromyalgia (Russell et al. (2008) Pain 136(3):432-444). The compounds of the invention, due to their ability to inhibit SERT and NET, are also expected to have this utility, and another embodiment of the invention relates to a method for treating chronic fatigue syndrome, comprising administering to a patient a therapeutically effective amount of a compound of the invention.

Sibutramine, a norepinephrine and dopamine reuptake inhibitor, has been shown to be useful in treating obesity (Wirth et al. (2001) JAMA 286(11):1331-1339). The compounds of the invention, due to their ability to inhibit NET, are also expected to have this utility, and another embodiment of the invention relates to a method for treating obesity, comprising administering to a patient a therapeutically effective amount of a compound of the invention.

Desvenlafaxine, an SNRI, has been shown to relieve vasomotor symptoms associated with menopause (Deecher et al. (2007) Endocrinology 148(3):1376-1383). The compounds of the invention, due to their ability to inhibit SERT and NET, are also expected to have this utility, and another embodiment of the invention relates to a method for treating vasomotor symptoms associated with menopause, comprising administering to a patient a therapeutically effective amount of a compound of the invention.

Research Tools

Since compounds of the invention possess both serotonin reuptake inhibition activity and norepinephrine reuptake inhibition activity, such compounds are also useful as research tools for investigating or studying biological systems or samples having serotonin or norepinephrine transporters. Any suitable biological system or sample having serotonin and/or norepinephrine transporters may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, serotonin reuptake in a mammal is inhibited by administering a serotonin reuptake-inhibiting amount of a compound of the invention. In another particular embodiment, norepinephrine reuptake in a mammal is inhibited by administering a norepinephrine reuptake-inhibiting amount of a compound of the invention. Compounds of the invention can also be used as research tools by conducting biological assays using such compounds.

When used as a research tool, a biological system or sample comprising a serotonin transporter and/or a norepinephrine transporter is typically contacted with a serotonin reuptake-inhibiting or norepinephrine reuptake-inhibiting amount of a compound of the invention. After the biological system or sample is exposed to the compound, the effects of inhibiting serotonin reuptake and/or norepinephrine reuptake are determined using conventional procedures and equipment. Exposure encompasses contacting cells or tissue with the compound, administering the compound to a mammal, for example by i.p. or i.v. administration, and so forth. This determining step may comprise measuring a response, i.e., a quantitative analysis or may comprise an observation, i.e., a qualitative analysis. Measuring a response involves, for example, determining the effects of the compound on the biological system or sample using conventional procedures and equipment, such as serotonin and norepinephrine reuptake assays. The assay results can be used to determine the activity level as well as the amount of compound necessary to achieve the desired result, i.e., a serotonin reuptake-inhibiting and a norepinephrine reuptake-inhibiting amount.

Additionally, compounds of the invention can be used as research tools for evaluating other chemical compounds, and thus are also useful in screening assays to discover, for example, new compounds having both serotonin reuptake-inhibiting activity and norepinephrine reuptake-inhibiting activity. In this manner, a compound of the invention is used as a standard in an assay to allow comparison of the results obtained with a test compound and with compounds of the invention to identify those test compounds that have about equal or superior reuptake-inhibiting activity, if any. For example, reuptake data for a test compound or a group of test compounds is compared to the reuptake data for a compound of the invention to identify those test compounds that have the desired properties, e.g., test compounds having reuptake-inhibiting activity about equal or superior to a compound of the invention, if any. This aspect of the invention includes, as separate embodiments, both the generation of comparison data (using the appropriate assays) and the analysis of the test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include serotonin and norepinephrine reuptake assays.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration. Further, the compounds of the invention may be administered, for example orally, in multiple doses per day (e.g., twice, three times or four times daily), in a single daily dose, in a twice-daily dose, in a single weekly dose, and so forth. It will be understood that any form of the compounds of the invention, (i.e., free base, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts and solvates of that compound.

Pharmaceutical compositions of the invention typically contain a therapeutically effective amount of a compound of the invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers, and the like, using conventional procedures and equipment.

In one embodiment, the pharmaceutical compositions are suitable for oral administration. One exemplary dosing regimen would be an oral dosage form administered once or twice daily. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (i.e., as capsules, tablets, pills, and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, i.e., each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, and glycerin. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (e.g., by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. A typical parenteral formulation is a sterile pH 4-7 aqueous solution of the active agent. Parenteral formulations may also contain one or more solubilizers, stabilizers, preservatives, wetting agents, emulsifiers, and dispersing agents. These formulations may be rendered sterile by use of a sterile injectable medium, a sterilizing agent, filtration, irradiation, or heat.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, compounds of the invention may be administered in combination with one or more other therapeutic agents. Thus, in one embodiment, compositions of the invention may optionally contain other drugs that are co-administered with a compound of the invention. For example, the composition may further comprise one or more drugs (also referred to as "secondary agents(s)") selected from the group of anti-Alzheimer's agents, anticonvulsants (antiepileptics), antidepressants, anti-Parkinson's agents, dual serotonin-norepinephrine reuptake inhibitors (SNRIs), non-steroidal anti-inflammatory agents (NSAIDs), norepinephrine reuptake inhibitors, opioid agonists (opioid analgesics), selective serotonin reuptake inhibitors, sodium channel blockers, sympatholytics, and combinations thereof. Numerous examples of such therapeutic agents are well known in the art, and examples are described herein. By combining a compound of the invention with a secondary agent, triple therapy can be achieved, i.e., serotonin reuptake inhibitory activity, norepinephrine reuptake inhibitory activity, and activity associated with the secondary agent (e.g., antidepressant activity), using only two active components. Since pharmaceutical compositions containing two active components are typically easier to formulate than compositions containing three active components, such two-component compositions provide a significant advantage over compositions containing three active components. Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

A compound of the invention may be either physically mixed with the second active agent to form a composition containing both agents; or each agent may be present in separate and distinct compositions which are administered to the patient simultaneously or sequentially. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (e.g., one hour later or three hours later). Alternatively, the combination may be administered by different routes of administration, i.e., one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount. i.e., are typically administered in an amount that produces a therapeutically beneficial effect when co-administered with a compound of the invention. The secondary agent can be in the form of a pharmaceutically acceptable salt, solvate, optically pure stereoisomer, and so forth. Thus, secondary agents listed below are intended to include all such forms, and are commercially available or can be prepared using conventional procedures and reagents.

Representative anti-Alzheimer's agents include, but are not limited to: donepezil, galantamine, memantine, rivastigmine, selegiline, tacrine, and combinations thereof.

Representative anticonvulsants (antiepileptics) include, but are not limited to: acetazolamide, albutoin, 4-amino-3-hydroxybutyric acid, beclamide, carbamazepine, cinromide, clomethiazole, clonazepam, diazepam, dimethadione, eterobarb, ethadione, ethosuximide, ethotoin, felbamate, fosphenyloin, gabapentin, lacosamide, lamotrigine, lorazepam, magnesium bromide, magnesium sulfate, mephenyloin, mephobarbital, methsuximide, midazolam, nitrazepam, oxazepam, oxcarbazepine, paramethadione, phenacemide, pheneturide, phenobarbital, phensuximide, phenyloin, potassium bromide, pregabalin, primidone, progabide, sodium bromide, sodium valproate, sulthiame, tiagabine, topiramate, trimethadione, valproic acid, valpromide, vigabatrin, zonisamide, and combinations thereof. In a particular embodiment, the anti convulsant is selected from carbamazepine, gabapentin, pregabalin, and combinations thereof.

Representative antidepressants include, but are not limited to: adinazolam, amitriptyline, clomipramine, desipramine, dothiepin (e.g., dothiepin hydrochloride), doxepin, imipramine, lofepramine, mirtazapine, nortriptyline, protriptyline, trimipramine, venlafaxine, zimelidine, and combinations thereof.

Representative anti-Parkinson's agents include, but are not limited to: amantadine, apomorphine, benztropine, bromocriptine, carbidopa, diphenhydramine, entacapone, levodopa, pergolide, pramipexole, ropinirole, selegiline, tolcapone, trihexyphenidyl, and combinations thereof.

Representative dual serotonin-norepinephrine reuptake inhibitors (SNRIs) include, but are not limited to: bicifadine, desvenlafaxine, duloxetine, milnacipran, nefazodone, venlafaxine, and combinations thereof.

Representative non-steroidal anti-inflammatory agents (NSAIDs) include, but are not limited to: acemetacin, acetaminophen, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, nimesulide, nitroflurbiprofen, olsalazine, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof. In a particular embodiment, the NSAID is selected from ibuprofen, indomethacin, nabumetone, naproxen (for example, naproxen sodium), and combinations thereof.

Representative muscle relaxants include, but are not limited to: carisoprodol, chlorzoxazone, cyclobenzaprine, diflunisal, metaxalone, methocarbamol, and combinations thereof.

Representative norepinephrine reuptake inhibitors include, but are not limited to: atomoxetine, buproprion and the buproprion metabolite hydroxybuproprion, maprotiline, reboxetine (for example, (S,S)-reboxetine), viloxazine, and combinations thereof. In a particular embodiment, the norepinephrine reuptake inhibitor is selected from atomoxetine, reboxetine, and combinations thereof.

Representative opioid agonists (opioid analgesics) include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid agonist is selected from codeine, dihydrocodeine, hydrocodone, hydromorphone, morphine, oxycodone, oxymorphone, tramadol, and combinations thereof.

Representative selective serotonin reuptake inhibitors (SSRIs) include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof. In certain embodiments, the SSRI is selected from citalopram, paroxetine, sertraline, and combinations thereof.

Representative sodium channel blockers include, but are not limited to: carbamazepine, fosphenyloin, lamotrignine, lidocaine, mexiletine, oxcarbazepine, phenyloin, and combinations thereof.

Representative sympatholytics include, but are not limited to: atenolol, clonidine, doxazosin, guanethidine, guanfacine, modafinil, phentolamine, prazosin, reserpine, tolazoline (e.g., tolazoline hydrochloride), tamsulosin, and combinations thereof.

The following formulations illustrate representative pharmaceutical compositions of the present invention:

Exemplary Hard Gelatin Capsules for Oral Administration

A compound of the invention (50 g), spray-dried lactose (440 g) and magnesium stearate (10 g) are thoroughly blended. The resulting composition is then loaded into hard gelatin capsules (500 mg of composition per capsule).

Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of compositions per tablet).

Exemplary Suspension Formulation for Oral Administration

The following ingredients are mixed to form a suspension containing 100 mg of active agent per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Injectable Formulation for Administration By Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration By Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 10 µg to about 500 µg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 µg to about 500 µg of the compound of the invention per dose.

EXAMPLES

The Preparations and Examples are provided to illustrate specific embodiments of the invention. These specific embodiments, however, are not intended to limit the scope of the invention in any way unless specifically indicated. The following abbreviations have the following meanings unless otherwise indicated and any other abbreviations used herein and not defined have their standard meaning:

| | |
| --- | --- |
| AcOH | acetic acid |
| $BH_3 \cdot Me_2S$ | borane dimethylsulphide complex |
| BSA | bovine serum albumin |
| DCM | dichloromethane (i.e., methylene chloride) |
| DIAD | diisopropyl azodicarboxylate |
| DMEM | Dulbecco's Modified Eagle's Medium |
| DMF | N,N-dimethylformamide |
| DMSO | dimethylsulfoxide |
| EDTA | ethylenediaminetetraacetic acid |
| EtOAc | ethyl acetate |
| EtOH | ethanol |
| FBS | fetal bovine serum |
| hDAT | human dopamine transporter |
| HEPES | 4-(2-hydroxyethyl)-1-piperazineethanesulfonic acid |
| hNET | human norepinephrine transporter |
| hSERT | human serotonin transporter |
| Me | methyl |
| MeCN | acetonitrile |
| MeOH | methanol |
| PBS | phosphate buffered saline |
| $PPh_3$ | triphenylphosphine |
| TEMPO | 2,2,6,6-tetramethyl-1-piperidinyloxy, free radical |
| TFA | trifluoroacetic acid |
| THF | tetrahydrofuran |

Any other abbreviations used herein but not defined have their standard, generally accepted meaning. Unless noted otherwise, all materials, such as reagents, starting materials and solvents, were purchased from commercial suppliers (such as Sigma-Aldrich, Fluka Riedel-de Haën, and the like) and were used without further purification.

In all of the compounds described in the examples, the two chiral centers are identified by the * and ** symbols. When describing the stereochemistry, the carbon atom indicated by the * symbol is designated first. Thus, an "SR" designation represents a compound having the (S) configuration at the carbon atom indicated by the * symbol and having the (R) configuration at the ** carbon atom. The same hold true for racemic mixtures. For example, an "RS/SR" designation represents a racemic mixture of (R,S) compounds and (S,R) compounds, i.e., a mixture of compounds having the (R) configuration at the * carbon atom and the (S) configuration at the ** carbon atom and compounds having the (S) configuration at the * carbon atom and the (R) configuration at the ** carbon atom.

Preparation 1

(S)—(R)-3-Oxiranylpyrrolidine-1-carboxylic Acid t-Butyl Ester and (S)-3-((S)-1,2-Dihydroxyethyl) pyrrolidine-1-carboxylic Acid t-Butyl Ester A solution of (S)-3-hydroxymethylpyrrolidine-1-carboxylic acid t-butyl ester (25.0 g, 124 mmol) in DCM (200 mL) was cooled with stirring to 0° C. A solution of potassium bromide (1.5 g, 12.4 mmol) and sodium bicarbonate (1.5 g, 17.4 mmol) dissolved in water (100 mL) was added. After 15 minutes of stirring at 0° C. 2,2,6,6,-tetramethylpiperidin-1-oxyl (195.3 mg, 1.2 mmol) was added, followed by the slow addition of sodium hypochlorite (77.3 mL, 136.6 mmol) dropwise keeping the internal temperature in the 6-8° C. range. The mixture was placed in an ice bath until the layers separated and the layers were back extracted with DCM (200 mL). The combined organic layers were washed with 1M NaCl in water (200 mL), dried over $Na_2SO_4$, filtered and concentrated to yield crude (S)-3-formylpyrrolidine-1-carboxylic acid t-butyl ester (21.5 g).

A slurry of methyltriphenylphosphonium bromide (16.1 g, 45.2 mmol) in THF (50 mL) was cooled to −78° C. 1M Sodium bis(trimethylsilyl)amide in THF (38.0 mL) was added and the mixture was stirred for 30 minutes. A solution of (S)-3-formylpyrrolidine-1-carboxylic acid t-butyl ester (3.0 g, 15.0 mmol) in THF (10 mL) was slowly added and the mixture was stirred at −78° C. for 2 hours. The mixture was warmed to room temperature over 3 hours and the reaction was quenched with half saturated $NH_4Cl$ (50 mL). The organic layer was washed with saturated aqueous NaCl (50 mL). The organic layer was collected, dried over $MgSO_4$, filtered, and concentrated. The resulting oil was slurried in hexanes (50 mL) and the precipitate was filtered off. The filtrate was concentrated, diluted with hexanes (25 mL) and chilled at −20° C. overnight. The precipitate was filtered off and the filtrate was purified by column chromatography eluting with EtOAc in hexanes (0-100%) to yield (R)-3-vinylpyrrolidine-1-carboxylic acid t-butyl ester as an oil (2.1 g).

$^1$H-NMR (400 MHz, DMSO): δ (ppm)=5.81-5.71 (m, 1H), 5.13-5.07 (m, 1H), 5.05-5.01 (m, 1H), 3.56-3.42 (m, 2H), 3.32-3.24 (m, 1H), 3.08-3.00 (m, 1H), 2.83-2.71 (m, 1H), 2.04-1.95 (m, 1H), 1.74-1.60 (m, 1H), 1.45 (s, 9H).

To (R)-3-vinylpyrrolidine-1-carboxylic acid t-butyl ester (6.1 g, 30.8 mmol) was added 3-pyridinecarbonitrile (320 mg, 3.1 mmol) and methyltrioxorhenium(VII) (192 mg, 769 μmol). The mixture was stirred until homogeneous. The mixture was placed in an ice water bath and 30% hydrogen peroxide (33:77, hydrogen peroxide:$H_2O$, 4.08 mL, 40.0 mmol) was added, while keeping the temperature below 35° C. The mixture was stirred for 2 hours. Additional methyltrioxorhenium(VII) (50 mg) was added and the mixture was stirred for 2 hours. The organic layer was collected and washed with a saturated sodium metabisulfite solution (10 mL) under an ice bath. The material was then washed with saturated aqueous NaCl. The organic layer was collected, dried over $Na_2SO_4$, filtered, and concentrated. The crude product was purified by column chromatography (0-100% EtOAc in hexanes) to give (S)-3-oxiranylpyrrolidine-1-carboxylic acid t-butyl ester as a yellowish oil (4.2 g).

$^1$H-NMR (400 MHz, DMSO): δ (ppm)=3.38-3.28 (m, 2H), 3.24-3.12 (m, 1H), 3.08-2.98 (m, 1H), 2.94-2.88 (m, 1H), 2.72-2.66 (m, 1H), 2.52-2.46 (m, 1H), 2.28-2.00 (m, 1H), 1.98-1.84 (m, 1H), 1.76-1.60 (m, 1H), 1.40 (s, 9H).

(R,R)-(−)-N,N'-Bis(3,5-di-t-butylsalicylidene)-1,2-cyclohexanediaminocobalt (II) (32.6 mg, 53.9 μmol) was dissolved in toluene (2.0 mL). AcOH was added (6.1 μL), and the resulting mixture was stirred at room temperature for 1 hour under air. The mixture was then concentrated and dried under high vacuum. (S)-3-Oxiranylpyrrolidine-1-carboxylic acid t-butyl ester (2.3 g, 10.8 mmol) was added, followed by water (97.1 μL), and the resulting mixture was stirred vigorously for 6 hours. Hexanes (15 mL) was added. The resulting solid was manually crushed and additional hexanes was added and stirred until the red solid became a yellowish precipitate. The precipitate was filtered and washed with 2 portions of hexanes. The precipitate was dried under vacuum to yield (S)-3-((S)-1,2-dihydroxyethyl)pyrrolidine-1-carboxylic acid t-butyl ester as an off-white solid (1.3 g). The filtrate was concentrated and purified by $SiO_2$ flash chromatography (0-100% EtOAc in hexanes) to yield (S)—(R)-3-oxiranylpyrrolidine-1-carboxylic acid t-butyl ester as an oil (970 mg).

(S)—(R)-3-Oxiranylpyrrolidine-1-carboxylic acid t-butyl ester: $^1$H-NMR (400 MHz, DMSO): δ (ppm)=3.38-3.28 (m, 2H), 3.24-3.12 (m, 1H), 3.08-2.98 (m, 1H), 2.94-2.88 (m, 1H), 2.72-2.66 (m, 1H), 2.52-2.46 (m, 1H), 2.28-2.00 (m, 1H), 1.98-1.84 (m, 1H), 1.76-1.60 (m, 1H), 1.40 (s, 9H).

Preparation 2

(S)-3-((S)-2-benzyloxy-1-hydroxyethyl)pyrrolidine-1-carboxylic acid t-butyl ester To a solution of (S)-3-((S)-1,2-dihydroxyethyl)pyrrolidine-1-carboxylic acid t-butyl ester (294.0 mg, 1.3 mmol) in DCM (6.3 mL) at room temperature, was added benzyl bromide (181.4 μL, 1525 μmol) followed by silver(II) oxide (472.4 mg, 3.8 mmol). The resulting mixture was stirred overnight. The mixture was filtered and the filtrate was subjected to same amount of silver (II) oxide and benzyl bromide and stirred overnight. The mixture was concentrated and the residue was purified by flash chromatography (12 g silica gel, 0-50% EtOAc/Hexanes). Desired fractions were combined and concentrated to yield the title compound as a colorless oil (165.6 mg).

Alternate Synthesis

To a solution of (S)—(S)-3-oxiranylpyrrolidine-1-carboxylic acid t-butyl ester (3.0 g, 14.1 mmol) in DMF (30 mL), was added benzyl alcohol (1460 μL, 14.1 mmol) followed by NaH (506 mg, 21.1 mmol). The resulting mixture was stirred at 50° C. for 3 hours, then cooled to room temperature. The mixture was extracted with EtOAc (25 mL) and saturated NaCl (25 mL). The aqueous layer was washed with EtOAc (5 mL). The organic layers were collected, dried over $Na_2SO_4$, filtered, and concentrated. The crude product was purified by flash chromatography (30-80% EtOAc/Hexanes) to yield the title compound (2.14 g).

Preparation 3

(S)-3-[(R)-2-Benzyloxy-1-(4-chloro-2-methylphenoxy)ethyl]pyrrolidine

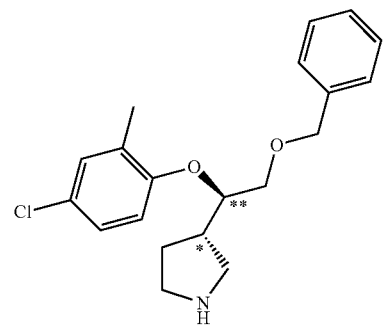 [SMILES: Cc1cc(Cl)ccc1O[C@@H](COCc1ccccc1)[C@H]1CCNC1]

4-Chloro-2-methylphenol (14.1 mg, 98.9 μmol) was combined with $PPh_3$ (26.0 mg, 98.9 μmol) dissolved in toluene (87.8 μL), and the mixture heated at 100° C. DIAD (19.5 μL, 98.9 μmol) was combined with (S)-3-((S)-2-benzyloxy-1-hydroxyethyl)pyrrolidine-1-carboxylic acid t-butyl ester (19.1 mg, 59.3 mmol) dissolved in toluene (58.0 μL), and slowly added to the heated mixture and stirred for two hours. The mixture was cooled to room temperature and concentrated. The residue was treated with 1.25M HCl in EtOH (474.6 μL) overnight at room temperature. The mixture was concentrated, the residue was redissolved in a mixture of MeCN (0.4 mL), AcOH (0.6 mL) and water (0.6 mL), filtered and purified by reverse phase preparative HPLC to yield the title compound as a mono-TFA salt (7.8 mg, 99% purity). MS m/z: $[M+H]^+$ calcd for $C_{20}H_{24}ClNO_2$, 346.15. found 346.2.

Example 1

(R)-2-(4-Chloro-2-methylphenoxy)-2-(S)-pyrrolidin-3-yl-ethanol

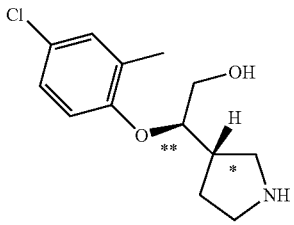 [SMILES: Cc1cc(Cl)ccc1O[C@@H](CO)[C@H]1CCNC1]

To a solution of (S)-3-[(R)-2-benzyloxy-1-(4-chloro-2-methylphenoxy)ethyl]-pyrrolidine.TFA (4.6 mg, 10 μmol) in EtOH (2.0 mL) at room temperature, was added concentrated HCl (~50 μL). To the stirred mixture was added 20% Pd(OH)$_2$/C (50 wt % water, 4.0 mg). The resulting mixture was degassed and flushed with hydrogen three times and then hydrogenated under a hydrogen balloon for 25 minutes. The mixture was filtered and the filtrate was concentrated. The resulting residue was redissolved in a mixture of AcOH (0.5 mL) and water (1.0 mL), filtered and purified by reverse phase preparative HPLC to yield the title compound as a mono-TFA salt (0.6 mg, 98% purity). MS m/z: $[M+H]^+$ calcd for $C_{13}H_{18}ClNO_2$, 256.10. found 256.2.

Example 2

Following the procedures described in the examples above, and substituting the appropriate starting materials and reagents, compounds 2-1 and 2-2, having formula II, were prepared as mono-TFA salts:

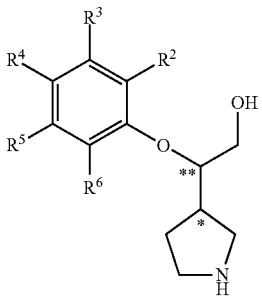

| Ex. | * | ** | $R^2$ | $R^3$ | $R^4$ | $R^5$ | $R^6$ | Formula | MS m/z: $[M+H]^+$ calcd | found |
|---|---|---|---|---|---|---|---|---|---|---|
| 1 | S | R | Cl | H | Cl | H | H | $C_{12}H_{15}Cl_2NO_2$ | 276.05 | 276.0 |
| 2 | S | R | Cl | Cl | H | H | H | $C_{12}H_{15}Cl_2NO_2$ | 276.05 | 276.0 |

1. (R)-2-(2,4-Dichlorophenoxy)-2-(S)-pyrrolidin-3-yl-ethanol
2. (R)-2-(2,3-Dichlorophenoxy)-2-(S)-pyrrolidin-3-yl-ethanol

Preparation 4

(S)-3-((S)-1-Hydroxy-2-methoxyethyl)pyrrolidine-1-carboxylic Acid t-Butyl Ester and (S)-3-((R)-1-Hydroxy-2-methoxyethyl)pyrrolidine-1-carboxylic Acid t-Butyl Ester To MeOH (30 mL) was carefully added sodium metal (2.7 g, 120 mmol) to produce a solution of sodium methoxide in methanol. (S)—(S)-3-Oxiranylpyrrolidine-1-carboxylic acid t-butyl ester (5.0 g, 23 mmol) was added and the reaction was stirred at 50° C. for 2 hours. The mixture was concentrated and water (100 mL) was added. The product was extracted with EtOAc (2×50 mL). The organic layer was collected, dried over $Na_2SO_4$, filtered, and concentrated. The crude product was purified by preparative HPLC to give (S)-3-((S)-1-hydroxy-2-methoxyethyl)pyrrolidine-1-carboxylic acid t-butyl ester an oil (3.0 g).

$^1$H-NMR (400 MHz, DMSO): δ (ppm)=4.80 (d, J=5.4 Hz, 1H), 3.52-3.42 (m, 1H), 3.37-3.29 (m, 2H), 3.28-3.20 (m, 5H), 3.18-3.06 (m, 1H), 3.06-2.98 (m, 1H), 2.23-2.09 (m, 1H), 1.82-1.72 (m, 1H), 1.68-1.50 (m, 1H), 1.38 (s, 9H).

(S)-3-((R)-1-Hydroxy-2-methoxyethyl)pyrrolidine-1-carboxylic acid t-butyl ester was prepared in the same manner, but using (S)—(R)-3-oxiranylpyrrolidine-1-carboxylic acid t-butyl ester.

$^1$H-NMR (400 MHz, DMSO): δ (ppm)=4.80 (d, J=5.5 Hz, 1H), 3.54-3.46 (m, 1H), 3.36-3.26 (m, 2H), 3.26-3.21 (m, 5H), 3.14-3.03 (m, 1H), 3.00-2.88 (m, 1H), 2.23-2.07 (m, 1H), 1.90-1.77 (m, 1H), 1.73-1.58 (m, 1H), 1.38 (s, 9H).

Example 3

(S)-3-[(R)-1-(2,4-Dichlorophenoxy)-2-methoxyethyl]pyrrolidine

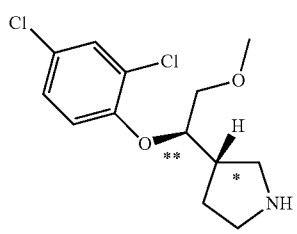 [SMILES: COC[C@H](Oc1ccc(Cl)cc1Cl)[C@H]1CCNC1]

(S)-3-((R)-1-Hydroxy-2-methoxyethyl)pyrrolidine-1-carboxylic acid t-butyl ester (10.0 mg, 40.8 μmol) was dissolved in DMF (0.1 mL). NaH (1.5 mg, 61.1 μmol) was slowly added and the mixture was stirred at room temperature for 15 minutes. Then, 2,4-dichloro-1-fluorobenzene (20.2 mg, 122 μmol) was added. The mixture was stirred at 100° C. for 1 hour, then cooled to room temperature. The mixture was concentrated then dissolved in 1.2M HCl in EtOH (1.0 mL, 1.2 mmol) and stirred overnight at room temperature. The product was concentrated and purified by preparative HPLC to yield the title compound as a mono-TFA salt (12.8 mg, 99% purity). MS m/z: [M+H] calcd for $C_{13}H_{17}Cl_2NO_2$, 290.06. found 290.0.

Example 4

Following the procedures described in the examples above, and substituting the appropriate starting materials and reagents, compounds 4-1 to 4-30, having formula IIIa, were prepared as mono-TFA salts:

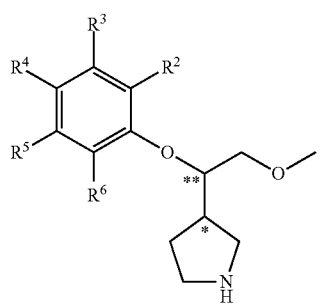

(IIIa)

| Ex. | * | ** | $R^2$ | $R^3$ | $R^4$ | $R^5$ | $R^6$ | Formula | MS m/z: $[M+H]^+$ calcd | found |
|---|---|---|---|---|---|---|---|---|---|---|
| 1 | | RS/SR | Cl | H | H | H | H | $C_{13}H_{18}ClNO_2$ | 256.10 | 257.2 |
| 2 | | RR/SS | Cl | H | H | H | H | $C_{13}H_{18}ClNO_2$ | 256.10 | 257.2 |
| 3 | S | R | H | —$CF_3$ | H | H | H | $C_{14}H_{18}F_3NO_2$ | 290.13 | 290.2 |
| 4 | | RR/SS | H | H | Cl | H | H | $C_{13}H_{18}ClNO_2$ | 256.10 | 257.2 |
| 5 | | RR/SS | Cl | Cl | H | H | H | $C_{13}H_{17}Cl_2NO_2$ | 290.06 | 290.2 |
| 6 | | RS/SR | Cl | Cl | H | H | H | $C_{13}H_{17}Cl_2NO_2$ | 290.06 | 290.2 |
| 7 | R | S | Cl | Cl | H | H | H | $C_{13}H_{17}Cl_2NO_2$ | 290.06 | 290.0 |
| 8 | R | R | Cl | Cl | H | H | H | $C_{13}H_{17}Cl_2NO_2$ | 290.06 | 290.0 |
| 9 | S | S | Cl | Cl | H | H | H | $C_{13}H_{17}Cl_2NO_2$ | 290.06 | 290.0 |
| 10 | S | R | Cl | Cl | H | H | H | $C_{13}H_{17}Cl_2NO_2$ | 290.06 | 290.0 |
| 11 | R | S | Cl | F | H | H | H | $C_{13}H_{17}ClFNO_2$ | 274.09 | 274.2 |
| 12 | S | R | Cl | F | H | H | H | $C_{13}H_{17}ClFNO_2$ | 274.09 | 274.0 |
| 13 | S | S | Cl | F | H | H | H | $C_{13}H_{17}ClFNO_2$ | 274.09 | 274.2 |
| 14 | R | S | Me | Cl | H | H | H | $C_{14}H_{20}ClNO_2$ | 270.12 | 270.2 |
| 15 | S | S | Me | Cl | H | H | H | $C_{14}H_{20}ClNO_2$ | 270.12 | 270.2 |
| 16 | S | R | Me | Cl | H | H | H | $C_{14}H_{20}ClNO_2$ | 270.12 | 270.2 |
| 17 | R | R | Me | Cl | H | H | H | $C_{14}H_{20}ClNO_2$ | 270.12 | 270.2 |
| 18 | | RR/SS | —$CF_3$ | Cl | H | H | H | $C_{14}H_{17}ClF_3NO_2$ | 324.09 | 324.8 |
| 19 | R | S | —$CF_3$ | Cl | H | H | H | $C_{14}H_{17}ClF_3NO_2$ | 324.09 | 324.0 |
| 20 | S | S | —$CF_3$ | Cl | H | H | H | $C_{14}H_{17}ClF_3NO_2$ | 324.09 | 324.0 |
| 21 | S | R | —$CF_3$ | Cl | H | H | H | $C_{14}H_{17}ClF_3NO_2$ | 324.09 | 324.0 |
| 22 | R | S | Cl | H | Cl | H | H | $C_{13}H_{17}Cl_2NO_2$ | 290.06 | 290.0 |
| 23 | S | S | Cl | H | Cl | H | H | $C_{13}H_{17}Cl_2NO_2$ | 290.06 | 290.0 |
| 24 | R | S | Cl | H | Me | H | H | $C_{14}H_{20}ClNO_2$ | 270.12 | 270.2 |
| 25 | S | R | Me | H | Cl | H | H | $C_{14}H_{20}ClNO_2$ | 270.12 | 270.2 |
| 26 | | RR/SS | Me | H | Cl | H | H | $C_{14}H_{20}ClNO_2$ | 270.12 | 270.8 |
| 27 | S | S | Cl | H | H | H | Cl | $C_{13}H_{17}Cl_2NO_2$ | 290.06 | 290.2 |
| 28 | S | R | Cl | H | H | H | Cl | $C_{13}H_{17}Cl_2NO_2$ | 290.06 | 290.2 |
| 29 | | RS/SR | H | Cl | H | Cl | H | $C_{13}H_{17}Cl_2NO_2$ | 290.06 | 290.2 |
| 30 | | RR/SS | H | Cl | H | Cl | H | $C_{13}H_{17}Cl_2NO_2$ | 290.06 | 290.2 |

1. 3-[1-(2-Chlorophenoxy)-2-methoxyethyl]pyrrolidine
2. 3-[1-(2-Chlorophenoxy)-2-methoxyethyl]pyrrolidine
3. (S)-3-[(R)-2-Methoxy-1-(3-trifluoromethylphenoxy)ethyl]pyrrolidine
4. 3-[1-(4-Chlorophenoxy)-2-methoxyethyl]pyrrolidine
5. 3-[1-(2,3-Dichlorophenoxy)-2-methoxyethyl]pyrrolidine
6. 3-[1-(2,3-Dichlorophenoxy)-2-methoxyethyl]pyrrolidine
7. (R)-3-[(S)-1-(2,3-Dichlorophenoxy)-2-methoxyethyl]pyrrolidine
8. (R)-3-[(R)-1-(2,3-Dichlorophenoxy)-2-methoxyethyl]pyrrolidine
9. (S)-3-[(S)-1-(2,3-Dichlorophenoxy)-2-methoxyethyl]pyrrolidine
10. (S)-3-[(R)-1-(2,3-Dichlorophenoxy)-2-methoxyethyl]pyrrolidine
11. (R)-3-[(S)-1-(2-Chloro-3-fluorophenoxy)-2-methoxyethyl]pyrrolidine
12. (S)-3-[(R)-1-(2-Chloro-3-fluorophenoxy)-2-methoxyethyl]pyrrolidine
13. (S)-3-[(S)-1-(2-Chloro-3-fluorophenoxy)-2-methoxyethyl]pyrrolidine
14. (R)-3-[(S)-1-(3-Chloro-2-methylphenoxy)-2-methoxyethyl]pyrrolidine
15. (S)-3-[(S)-1-(3-Chloro-2-methylphenoxy)-2-methoxyethyl]pyrrolidine
16. (S)-3-[(R)-1-(3-Chloro-2-methylphenoxy)-2-methoxyethyl]pyrrolidine
17. (R)-3-[(R)-1-(3-Chloro-2-methylphenoxy)-2-methoxyethyl]pyrrolidine
18. 3-[1-(3-Chloro-2-trifluoromethylphenoxy)-2-methoxyethyl]pyrrolidine
19. (R)-3-[(S)-1-(3-Chloro-2-trifluoromethylphenoxy)-2-methoxyethyl]pyrrolidine
20. (S)-3-[(S)-1-(3-Chloro-2-trifluoromethylphenoxy)-2-methoxyethyl]pyrrolidine
21. (S)-3-[(R)-1-(3-Chloro-2-trifluoromethylphenoxy)-2-methoxyethyl]pyrrolidine
22. (R)-3-[(S)-1-(2,4-Dichlorophenoxy)-2-methoxyethyl]pyrrolidine
23. (S)-3-[(S)-1-(2,4-Dichlorophenoxy)-2-methoxyethyl]pyrrolidine
24. (R)-3-[(S)-1-(2-Chloro-4-methylphenoxy)-2-methoxyethyl]pyrrolidine
25. (S)-3-[(R)-1-(4-Chloro-2-methylphenoxy)-2-methoxyethyl]pyrrolidine
26. 3-[1-(4-Chloro-2-methylphenoxy)-2-methoxyethyl]pyrrolidine
27. (S)-3-[(S)-1-(2,6-Dichlorophenoxy)-2-methoxyethyl]pyrrolidine
28. (S)-3-[(R)-1-(2,6-Dichlorophenoxy)-2-methoxyethyl]pyrrolidine
29. 3-[1-(3,5-Dichlorophenoxy)-2-methoxyethyl]pyrrolidine
30. 3-[1-(3,5-Dichlorophenoxy)-2-methoxyethyl]pyrrolidine Preparation 5

3-(1-Hydroxy-3-methoxypropyl)pyrrolidine-1-carboxylic Acid t-Butyl Ester

2-Oxopyrrolidine-1-carboxylic acid t-butyl ester (1.4 mL, 8.2 mmol) was dissolved in THF (10 mL) under nitrogen, then was cooled at −78° C. 2M Lithium diisopropylamide in heptane/THF/ethylbenzene (8.2 mL; 16 mmol) was added over 20 minutes, and the resulting mixture was stirred for 1.5 hours at −78° C. 3-Methoxypropionyl chloride (1.0 g, 8.2 mmol) was dissolved in THF (10 mL) and slowly added dropwise via syringe to the mixture over 30 minutes, then stirred overnight at room temperature. The reaction was quenched with saturated aqueous $NH_4Cl$ (50 mL), and the mixture stirred at room temperature for 30 minutes. The mixture was extracted with EtOAc (200 mL). The organic layer was washed with saturated aqueous $NaHCO_3$ (2×75 mL), then saturated aqueous NaCl (2×75 mL). The aqueous layers were combined and re-extracted with EtOAc (75 mL). The organic layers were combined, dried over $Na_2SO_4$, filtered, and concentrated by rotary evaporation. The material was then placed on high vacuum for 10 minutes to yield a crude red oil (2.0 g). The oil was purified by preparative HPLC (sample dissolved in 50% AcOH/$H_2O$; 10-70% MeCN/$H_2O$; 0.05% TFA; over 80 minutes on a 2" column at 40 mL/min). The fractions were collected and lyophilized to yield a yellow oil.

The oil was dissolved in THF (2.0 mL). While cooling in an ice bath, 2M $BH_3.Me_2S$ in THF (10 mL, 20 mmol) was slowly added. The mixture was stirred at room temperature for 1 hour, then at 60° C. for 2 hours. The reaction was then carefully quenched with cold MeOH (20 mL) (caution exothermic), and the mixture stirred overnight at room temperature. The mixture was then diluted with EtOAc (30 mL), and washed with $NaHCO_3$ (50 mL×2) and then saturated aqueous NaCl (30 mL). The organic layer was dried over $Na_2SO_4$, filtered, and concentrated by rotary evaporation to yield the title compound as a yellow oil (50 mg). MS m/z: $[M+H]^+$ calcd for $C_{13}H_{25}NO_4$, 259.34. found 260.4.

Example 5

3-[1-(4-Chloro-2-methylphenoxy)-3-methoxypropyl] pyrrolidine

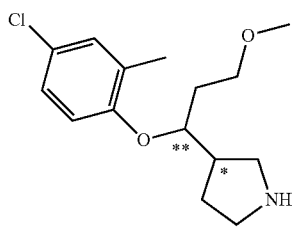 [SMILES: COCCC(Oc1ccc(Cl)cc1C)C1CCNC1]

3-(1-Hydroxy-3-methoxypropyl)pyrrolidine-1-carboxylic acid t-butyl ester (50 mg, 0.2 mmol) was dissolved in DMF (1.00 mL). While stirring, 60% NaH in oil (0.4:0.6, NaH: mineral oil, 40 mg, 0.6 mmol) was slowly added, and the mixture was stirred for 15 minutes. 5-Chloro-2-fluorotoluene (74 uL, 610 µmol) was added. The mixture was stirred at room temperature for 15 minutes before heating at 80° C. for 3 hours. The reaction was quenched with MeOH (2 mL) and stirred for 15 minutes. The solvent was removed and the crude material was dissolved in 1.25M HCl in EtOH (1.0 mL, 1.2 mmol) and stirred overnight at room temperature. The solvent was removed and the product was purified by purified by preparative HPLC to yield two mixtures of stereoisomers as mono-TFA salts: a mixture of the RS/SR stereoisomers and a mixture of the RR/SS stereoisomers.

$1^{st}$ peak (10.7 mg, 100% purity): LSMS m/z: $[M+H]^+$ calcd for $C_{15}H_{22}ClNO_2$, 283.79. found 284.4. $^1$H-NMR (400 MHz, $CD_3OD$): δ (ppm)=7.17-7.13 (dd 2H), 7.03-7.01 (d, 1H), 4.70-4.65 (m, 1H), 3.51-3.48 (m, 2H), 3.40-3.37 (m, 2H), 3.30 (s, 3H), 3.26-3.18 (m, 2H), 2.86-2.78 (m, 1H), 2.25 (s, 3H), 1.97-1.94 (m, 2H), 1.93-1.82 (m, 2H).

$2^{nd}$ peak (8.2 mg, 100% purity): LSMS m/z: [M+H] calcd for $C_{15}H_{22}ClNO_2$, 283.79. found 284.4. $^1$H-NMR (400 MHz, $CD_3OD$): δ (ppm)=7.18-7.03 (dd 2H), 7.02-7.00 (d, 1H), 4.71-4.68 (m, 1H), 3.53-3.48 (m, 2H), 3.45-3.40 (m, 2H), 3.30 (s, 3H), 3.08-3.03 (m, 2H), 2.84-2.79 (m, 1H), 2.26 (s, 3H), 2.10-2.05 (m, 2H), 1.98-1.92 (m, 2H).

Preparation 6

(S)-3-(R)-2-Ethoxy-1-hydroxyethyl)pyrrolidine-1-carboxylic Acid t-Butyl Ester (S)—(R)-3-Oxiranylpyrrolidine-1-carboxylic acid t-butyl ester (440 mg, 2.1 mmol) was added to 2M of sodium ethoxide in EtOH (2.1 mL, 4.1 mmol; prepared from EtOH and NaH). The resulting solution was placed in a microwave reactor for 10 minutes at 100° C., then cooled to room temperature. DCM (5 mL) was added, followed by washing with saturated aqueous NaCl (5 mL). The organic layer was collected, dried over $Na_2SO_4$, filtered, and concentrated. The crude product was purified by column chromatography (0-100% ether/Hexanes) to give the title compound as a clear oil (400 mg).

$^1$H-NMR (400 MHz, $CDCl_3$): δ (ppm)=3.67-3.61 (m, 1H), 3.58-3.38 (m, 5H), 3.32-3.20 (m, 2H), 3.04-2.98 (m, 1H), 2.28-2.16 (m, 1H), 2.11-2.02 (m, 1H), 1.85-1.74 (m, 1H), 1.45 (s, 9H), 1.27-1.18 (m, 4H).

Example 6

(S)-3-[(R)-1-(2,4-Dichlorophenoxy)-2-ethoxyethyl] pyrrolidine

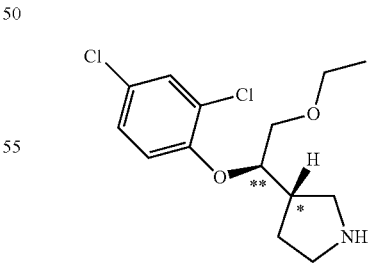

(S)-3-((R)-2-Ethoxy-1-hydroxyethyl)pyrrolidine-1-carboxylic acid t-butyl ester (25.0 mg, 96.4 µmol) was dissolved in DMF (200 µL). NaH (2776 µg, 115.7 mmol) was added and the mixture was stirred at room temperature for 15 minutes. 2,4-Dichloro-1-fluorobenzene (22.6 µL, 192.8 µmol) was added and the mixture was stirred at 70° C. for 3 hours. The mixture was concentrated then dissolved in 1.2M HCl in EtOH (1.0 mL, 1.2 mmol) and stirred overnight. The product was concentrated and purified by preparative HPLC (10-40%, 60 min, BDS) to yield the title compound as a mono-TFA salt oil (24.4 mg, 100% purity). MS m/z: [M+H]$^+$ calcd for $C_{14}H_{19}Cl_2NO_2$, 304.08. found 304.0.

Example 7

Following the procedures described in the examples above, and substituting the appropriate starting materials and reagents, compounds 7-1 to 7-32, having formula IIIb, were prepared as mono-TFA salts:

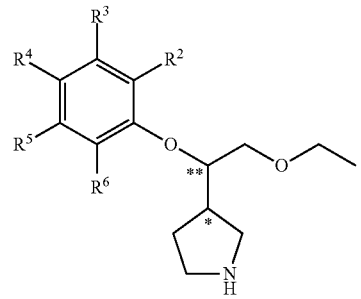

(IIIb)

| Ex. | * | ** | R² | R³ | R⁴ | R⁵ | R⁶ | Formula | MS m/z: [M + H]⁺ calcd | found |
|---|---|---|---|---|---|---|---|---|---|---|
| 1 | S | R | Cl | H | H | H | H | $C_{14}H_{20}ClNO_2$ | 270.12 | 270.2 |
| 2 | S | R | H | —CF₃ | H | H | H | $C_{15}H_{20}F_3NO_2$ | 304.14 | 304.0 |
| 3 | S | S | H | —CF₃ | H | H | H | $C_{15}H_{20}F_3NO_2$ | 304.14 | 304.2 |
| 4 | S | R | H | H | Cl | H | H | $C_{14}H_{20}ClNO_2$ | 270.12 | 270.2 |
| 5 | S | R | H | H | F | H | H | $C_{14}H_{20}FNO_2$ | 254.15 | 254.2 |
| 6 | S | R | H | H | —CF₃ | H | H | $C_{15}H_{20}F_3NO_2$ | 304.14 | 304.2 |
| 7 | S | R | Cl | Cl | H | H | H | $C_{14}H_{19}Cl_2NO_2$ | 304.08 | 304.0 |
| 8 | S | S | Cl | Cl | H | H | H | $C_{14}H_{19}Cl_2NO_2$ | 304.08 | 304.0 |
| 9 | S | R | Cl | F | H | H | H | $C_{14}H_{19}ClFNO_2$ | 288.11 | 288.0 |
| 10 | S | S | Cl | F | H | H | H | $C_{14}H_{19}ClFNO_2$ | 288.11 | 288.2 |
| 11 | S | R | F | F | H | H | H | $C_{14}H_{19}F_2NO_2$ | 272.14 | 272.2 |
| 12 | S | R | F | —CF₃ | H | H | H | $C_{15}H_{19}F_4NO_2$ | 322.14 | 322.2 |
| 13 | S | R | Me | Cl | H | H | H | $C_{15}H_{22}ClNO_2$ | 284.13 | 284.2 |
| 14 | S | S | Me | Cl | H | H | H | $C_{15}H_{22}ClNO_2$ | 284.13 | 284.2 |
| 15 | S | R | —CF₃ | Cl | H | H | H | $C_{15}H_{19}ClF_3NO_2$ | 338.11 | 338.0 |
| 16 | S | S | —CF₃ | Cl | H | H | H | $C_{15}H_{19}ClF_3NO_2$ | 338.11 | 338.0 |
| 17 | S | S | Cl | H | Cl | H | H | $C_{14}H_{19}Cl_2NO_2$ | 304.08 | 304.0 |
| 18 | S | R | Cl | H | F | H | H | $C_{14}H_{19}ClFNO_2$ | 288.11 | 288.0 |
| 19 | S | R | Cl | H | —CF₃ | H | H | $C_{14}H_{19}Cl_2NO_2$ | 304.08 | 304.0 |
| 20 | S | R | Cl | H | —CN | H | H | $C_{15}H_{19}ClN_2O_2$ | 295.11 | 295.2 |
| 21 | S | R | F | H | Cl | H | H | $C_{14}H_{19}ClFNO_2$ | 288.11 | 288.0 |
| 22 | S | R | Me | H | Cl | H | H | $C_{15}H_{22}ClNO_2$ | 284.13 | 284.2 |
| 23 | S | R | —CF₃ | H | Cl | H | H | $C_{15}H_{19}ClF_3NO_2$ | 338.11 | 338.2 |
| 24 | S | R | H | Cl | Cl | H | H | $C_{15}H_{19}ClF_3NO_2$ | 338.11 | 338.2 |
| 25 | S | R | H | Cl | —CN | H | H | $C_{15}H_{19}ClN_2O_2$ | 295.11 | 295.2 |
| 26 | S | R | H | F | Cl | H | H | $C_{14}H_{19}ClFNO_2$ | 288.11 | 288.0 |
| 27 | S | R | H | Cl | H | Cl | H | $C_{14}H_{19}Cl_2NO_2$ | 304.08 | 304.2 |
| 28 | S | R | H | Cl | H | F | H | $C_{14}H_{19}ClFNO_2$ | 288.11 | 288.2 |
| 29 | S | R | F | Cl | Cl | H | H | $C_{14}H_{18}Cl_2FNO_2$ | 322.07 | 322.0 |
| 30 | S | R | Cl | F | H | H | F | $C_{14}H_{18}ClF_2NO_2$ | 306.10 | 306.0 |
| 31 | S | R | Cl | H | F | H | Cl | $C_{14}H_{18}Cl_2FNO_2$ | 322.07 | 322.0 |
| 32 | S | R | Cl | H | H | Cl | F | $C_{14}H_{18}Cl_2FNO_2$ | 322.07 | 322.0 |

1. (S)-3-[(R)-1-(2-Chlorophenoxy)-2-ethoxyethyl]pyrrolidine
2. (S)-3-[(R)-2-Ethoxy-1-(3-trifluoromethylphenoxy)ethyl]pyrrolidine
3. (S)-3-[(S)-2-Ethoxy-1-(3-trifluoromethylphenoxy)ethyl]pyrrolidine
4. (S)-3-[(R)-1-(4-Chlorophenoxy)-2-ethoxyethyl]pyrrolidine
5. (S)-3-[(R)-2-Ethoxy-1-(4-fluorophenoxy)ethyl]pyrrolidine
6. (S)-3-[(R)-2-Ethoxy-1-(4-trifluoromethylphenoxy)ethyl]pyrrolidine
7. (S)-3-[(R)-1-(2,3-Dichlorophenoxy)-2-ethoxyethyl]pyrrolidine
8. (S)-3-[(S)-1-(2,3-Dichlorophenoxy)-2-ethoxyethyl]pyrrolidine
9. (S)-3-[(R)-1-(2-Chloro-3-fluorophenoxy)-2-ethoxyethyl]pyrrolidine
10. (S)-3-[(S)-1-(2-Chloro-3-fluorophenoxy)-2-ethoxyethyl]pyrrolidine
11. (S)-3-[(R)-1-(2,3-Difluorophenoxy)-2-ethoxyethyl]pyrrolidine
12. (S)-3-[(R)-2-Ethoxy-1-(2-fluoro-3-trifluoromethylphenoxy)ethyl]pyrrolidine
13. (S)-3-[(R)-1-(3-Chloro-2-methylphenoxy)-2-ethoxyethyl]pyrrolidine
14. (S)-3-[(S)-1-(3-Chloro-2-methylphenoxy)-2-ethoxyethyl]pyrrolidine
15. (S)-3-[(R)-1-(3-Chloro-2-trifluoromethylphenoxy)-2-ethoxyethyl]pyrrolidine
16. (S)-3-[(S)-1-(3-Chloro-2-trifluoromethylphenoxy)-2-ethoxyethyl]pyrrolidine
17. (S)-3-[(S)-1-(2,4-Dichlorophenoxy)-2-ethoxyethyl]pyrrolidine
18. (S)-3-[(R)-1-(2-Chloro-4-fluorophenoxy)-2-ethoxyethyl]pyrrolidine
19. (S)-3-[(R)-1-(2-Chloro-4-trifluoromethylphenoxy)-2-ethoxyethyl]pyrrolidine
20 3-Chloro-4-((R)-2-ethoxy-1-(S)-pyrrolidin-3-ylethoxy)benzonitrile
21. (S)-3-[(R)-1-(4-Chloro-2-fluorophenoxy)-2-ethoxyethyl]pyrrolidine
22. (S)-3-[(R)-1-(4-Chloro-2-methylphenoxy)-2-ethoxyethyl]pyrrolidine
23. (S)-3-[(R)-1-(4-Chloro-2-trifluoromethylphenoxy)-2-ethoxyethyl]pyrrolidine
24. (S)-3-[(R)-1-(3,4-Dichlorophenoxy)-2-ethoxyethyl]pyrrolidine
25. 2-Chloro-4-((R)-2-ethoxy-1-(S)-pyrrolidin-3-ylethoxy)benzonitrile

| Ex. * | ** | $R^2$ | $R^3$ | $R^4$ | $R^5$ | $R^6$ | Formula | MS m/z: [M + H]+ calcd | found |
|---|---|---|---|---|---|---|---|---|---|

26. (S)-3-[(R)-1-(4-Chloro-3-fluorophenoxy)-2-ethoxyethyl]pyrrolidine
27. (S)-3-[(R)-1-(3,5-Dichlorophenoxy)-2-ethoxyethyl]pyrrolidine
28. (S)-3-[(R)-1-(3-Chloro-5-fluorophenoxy)-2-ethoxyethyl]pyrrolidine
29. (S)-3-[(R)-1-(3,4-Dichloro-2-fluorophenoxy)-2-ethoxyethyl]pyrrolidine
30. (S)-3-[(R)-1-(2-Chloro-3,6-difluorophenoxy)-2-ethoxyethyl]pyrrolidine
31. (S)-3-[(R)-1-(2,6-Dichloro-4-fluorophenoxy)-2-ethoxyethyl]pyrrolidine
32. (S)-3-[(R)-1-(3,6-Dichloro-2-fluorophenoxy)-2-ethoxyethyl]pyrrolidine Preparation 7

(S)-3-((R)-1-Hydroxy-2-isopropoxyethyl)pyrrolidine-1-carboxylic Acid t-Butyl Ester Isopropyl alcohol (215 μL, 2.8 mmol) was dissolved in THF (428 μL), and the mixture was cooled at 0° C. NaH (33.8 mg, 1.4 mmol) was added in 4 portions, and the mixture stirred for 10 minutes at room temperature. (S)—(R)-3-Oxiranylpyrrolidine-1-carboxylic acid t-butyl ester (200 mg, 938 μmol) was added. The resulting solution was placed in a microwave reactor for 10 minutes at 100° C., then cooled to room temperature. The mixture was extracted with Hexanes (10 mL) and washed with water (10 mL). The organic layer was collected, dried over $Na_2SO_4$, filtered, and concentrated. The crude product was purified by column chromatography (0-100% EtOAc in hexanes) to give the title compound as a clear oil (162 mg).
$^1$H-NMR (400 MHz, DMSO): δ (ppm)=4.71 (d, J=5.2 Hz, 1H), 3.58-3.48 (septuplet, J=6.1 Hz, 1H), 3.47-3.41 (m, 1H), 3.36-3.20 (m, 4H), 3.15-3.04 (m, 1H), 3.00-2.90 (m, 1H), 2.21-2.10 (m, 1H), 1.90-1.80 (m, 1H), 1.72-1.57 (m, 1H), 1.38 (s, 9H), 1.0 (d, J=6.1 Hz, 6H).

Example 8

(S)-3-[(R)-1-(2,4-Dichlorophenoxy)-2-isopropoxyethyl]pyrrolidine

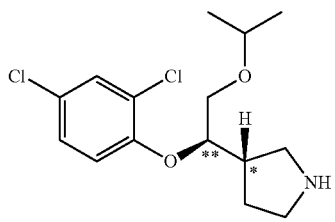 [SMILES: CC(C)OC[C@H](Oc1ccc(Cl)cc1Cl)[C@H]1CCNC1]

(S)-3-((R)-1-Hydroxy-2-isopropoxyethyl)pyrrolidine-1-carboxylic acid t-butyl ester (25.0 mg, 91.4 μmol) was dissolved in DMF (190 μL). NaH (2.6 mg, 109.7 μmol) was added and the mixture was stirred at room temperature for 15 minutes. 2,4-Dichloro-1-fluorobenzene (21.4 μL, 182.9 mmol) was added and the mixture was stirred at 70° C. for 3 hours. The mixture was concentrated then dissolved in 1.2M HCl in EtOH (949 μL, 1.1 mmol) and stirred overnight. The product was concentrated and purified by preparative HPLC to yield the title compound as a mono-TFA salt oil (29.5 mg, 97% purity). MS m/z: [M+H]+ calcd for $C_{15}H_{21}Cl_2NO_2$, 318.10. found 318.0.

Example 9

Following the procedures described in the examples above, and substituting the appropriate starting materials and reagents, compounds 9-1 to 9-29, having formula IIIc, were prepared as mono-TFA salts:

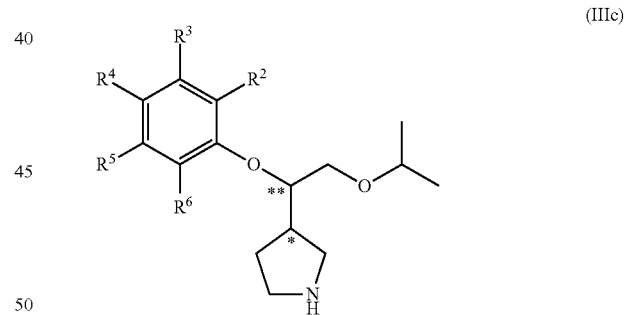

(IIIc)

| Ex. * | ** | $R^2$ | $R^3$ | $R^4$ | $R^5$ | $R^6$ | Formula | MS m/z: [M + H]+ calcd | found |
|---|---|---|---|---|---|---|---|---|---|
| 1 R | S | H | —$CF_3$ | H | H | H | $C_{16}H_{22}F_3NO_2$ | 318.16 | 318.2 |
| 2 R | R | H | —$CF_3$ | H | H | H | $C_{16}H_{22}F_3NO_2$ | 318.16 | 318.2 |
| 3 S | S | H | —$CF_3$ | H | H | H | $C_{16}H_{22}F_3NO_2$ | 318.16 | 318.2 |
| 4 S | R | H | —$CF_3$ | H | H | H | $C_{16}H_{22}F_3NO_2$ | 318.16 | 318.2 |
| 5 R | S | Cl | Cl | H | H | H | $C_{15}H_{21}Cl_2NO_2$ | 318.10 | 318.0 |
| 6 R | R | Cl | Cl | H | H | H | $C_{15}H_{21}Cl_2NO_2$ | 318.10 | 318.0 |
| 7 S | R | Cl | Cl | H | H | H | $C_{15}H_{21}Cl_2NO_2$ | 318.10 | 318.0 |
| 8 S | S | Cl | Cl | H | H | H | $C_{15}H_{21}Cl_2NO_2$ | 318.10 | 318.0 |
| 9 R | S | Cl | F | H | H | H | $C_{15}H_{21}ClFNO_2$ | 302.12 | 302.2 |
| 10 R | R | Cl | F | H | H | H | $C_{15}H_{21}ClFNO_2$ | 302.12 | 302.0 |
| 11 S | S | Cl | F | H | H | H | $C_{15}H_{21}ClFNO_2$ | 302.12 | 302.2 |
| 12 S | R | Cl | F | H | H | H | $C_{15}H_{21}ClFNO_2$ | 302.12 | 302.2 |

-continued

| Ex. | * | ** | $R^2$ | $R^3$ | $R^4$ | $R^5$ | $R^6$ | Formula | MS m/z: $[M+H]^+$ calcd | found |
|---|---|---|---|---|---|---|---|---|---|---|
| 13 | R | S | Me | Cl | H | H | H | $C_{16}H_{24}ClNO_2$ | 298.15 | 298.2 |
| 14 | R | R | Me | Cl | H | H | H | $C_{16}H_{24}ClNO_2$ | 298.15 | 298.2 |
| 15 | S | S | Me | Cl | H | H | H | $C_{16}H_{24}ClNO_2$ | 298.15 | 298.2 |
| 16 | S | R | Me | Cl | H | H | H | $C_{16}H_{24}ClNO_2$ | 298.15 | 298.2 |
| 17 | R | S | —$CF_3$ | Cl | H | H | H | $C_{16}H_{21}ClF_3NO_2$ | 352.12 | 352.2 |
| 18 | R | R | —$CF_3$ | Cl | H | H | H | $C_{16}H_{21}ClF_3NO_2$ | 352.12 | 352.0 |
| 19 | S | S | —$CF_3$ | Cl | H | H | H | $C_{16}H_{21}ClF_3NO_2$ | 352.12 | 352.2 |
| 20 | S | R | —$CF_3$ | Cl | H | H | H | $C_{16}H_{21}ClF_3NO_2$ | 352.12 | 352.2 |
| 21 | R | S | Cl | H | Cl | H | H | $C_{15}H_{21}Cl_2NO_2$ | 318.10 | 318.0 |
| 22 | R | R | Cl | H | Cl | H | H | $C_{15}H_{21}Cl_2NO_2$ | 318.10 | 318.0 |
| 23 | S | S | Cl | H | Cl | H | H | $C_{15}H_{21}Cl_2NO_2$ | 318.10 | 318.0 |
| 24 | R | S | Me | H | Cl | H | H | $C_{16}H_{24}ClNO_2$ | 298.15 | 298.2 |
| 25 | R | R | Me | H | Cl | H | H | $C_{16}H_{24}ClNO_2$ | 298.15 | 298.2 |
| 26 | R | S | Cl | H | H | H | Cl | $C_{15}H_{21}Cl_2NO_2$ | 318.10 | 318.2 |
| 27 | R | R | Cl | H | H | H | Cl | $C_{15}H_{21}Cl_2NO_2$ | 318.10 | 318.0 |
| 28 | S | S | Cl | H | H | H | Cl | $C_{15}H_{21}Cl_2NO_2$ | 318.10 | 318.0 |
| 29 | S | R | Cl | H | H | H | Cl | $C_{15}H_{21}Cl_2NO_2$ | 318.10 | 318.0 |

1. (R)-3-[(S)-2-Isopropoxy-1-(3-trifluoromethylphenoxy)ethyl]pyrrolidine
2. (R)-3-[(R)-2-Isopropoxy-1-(3-trifluoromethylphenoxy)ethyl]pyrrolidine
3. (S)-3-[(S)-2-Isopropoxy-1-(3-trifluoromethylphenoxy)ethyl]pyrrolidine
4. (S)-3-[(R)-2-Isopropoxy-1-(3-trifluoromethylphenoxy)ethyl]pyrrolidine
5. (R)-3-[(S)-1-(2,3-Dichlorophenoxy)-2-isopropoxyethyl]pyrrolidine
6. (R)-3-[(R)-1-(2,3-Dichlorophenoxy)-2-isopropoxyethyl]pyrrolidine
7. (S)-3-[(R)-1-(2,3-Dichlorophenoxy)-2-isopropoxyethyl]pyrrolidine
8. (S)-3-[(S)-1-(2,3-Dichlorophenoxy)-2-isopropoxyethyl]pyrrolidine
9. (R)-3-[(S)-1-(2-Chloro-3-fluorophenoxy)-2-isopropoxyethyl]pyrrolidine
10. (R)-3-[(R)-1-(2-Chloro-3-fluorophenoxy)-2-isopropoxyethyl]pyrrolidine
11. (S)-3-[(S)-1-(2-Chloro-3-fluorophenoxy)-2-isopropoxyethyl]pyrrolidine
12. (S)-3-[(S)-1-(2-Chloro-3-fluorophenoxy)-2-isopropoxyethyl]pyrrolidine
13. (R)-3-[(S)-1-(3-Chloro-2-methylphenoxy)-2-isopropoxyethyl]pyrrolidine
14. (R)-3-[(R)-1-(3-Chloro-2-methylphenoxy)-2-isopropoxyethyl]pyrrolidine
15. (S)-3-[(S)-1-(3-Chloro-2-methylphenoxy)-2-isopropoxyethyl]pyrrolidine
16. (S)-3-[(R)-1-(3-Chloro-2-methylphenoxy)-2-isopropoxyethyl]pyrrolidine
17. (R)-3-[(S)-1-(3-Chloro-2-trifluoromethylphenoxy)-2-isopropoxyethyl]pyrrolidine
18. (R)-3-[(R)-1-(3-Chloro-2-trifluoromethylphenoxy)-2-isopropoxyethyl]pyrrolidine
19. (S)-3-[(S)-1-(3-Chloro-2-trifluoromethylphenoxy)-2-isopropoxyethyl]pyrrolidine
20. (S)-3-[(R)-1-(3-Chloro-2-trifluoromethyl-phenoxy)-2-isopropoxyethyl]pyrrolidine
21. (R)-3-[(S)-1-(2,4-Dichlorophenoxy)-2-isopropoxyethyl]pyrrolidine
22. (R)-3-[(R)-1-(2,4-Dichlorophenoxy)-2-isopropoxyethyl]pyrrolidine
23. (S)-3-[(S)-1-(2,4-Dichlorophenoxy)-2-isopropoxyethyl]pyrrolidine
24. (R)-3-[(S)-1-(4-Chloro-2-methylphenoxy)-2-isopropoxyethyl]pyrrolidine
25. (R)-3-[(R)-1-(3-Chloro-2-methylphenoxy)-2-isopropoxyethyl]pyrrolidine
26. (R)-3-[(S)-1-(2,6-Dichlorophenoxy)-2-isopropoxyethyl]pyrrolidine
27. (R)-3-[(R)-1-(2,6-Dichlorophenoxy)-2-isopropoxyethyl]pyrrolidine
28. (S)-3-[(S)-1-(2,6-Dichlorophenoxy)-2-isopropoxyethyl]pyrrolidine
29. (S)-3-[(R)-1-(2,6-Dichlorophenoxy)-2-isopropoxyethyl]pyrrolidine

Example 10

Following the procedures described in the examples above, and substituting the appropriate starting materials and reagents, compounds 10-1 to 10-5, having formula VIIIa, were prepared as mono-TFA salts:

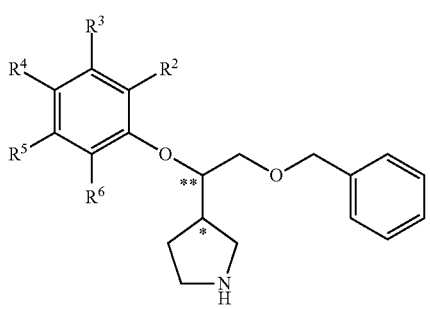

(VIIa)

| Ex. | * | ** | $R^2$ | $R^3$ | $R^4$ | $R^5$ | $R^6$ | Formula | MS m/z: $[M+H]^+$ calcd | found |
|---|---|---|---|---|---|---|---|---|---|---|
| 1 | S | R | Cl | H | H | H | H | $C_{19}H_{22}ClNO_2$ | 332.13 | 332.2 |
| 2 | S | R | Cl | Cl | H | H | H | $C_{19}H_{21}Cl_2NO_2$ | 366.10 | 366.0 |
| 3 | S | R | Cl | H | Cl | H | H | $C_{19}H_{21}Cl_2NO_2$ | 366.10 | 366.0 |
| 4 | S | R | Cl | H | H | H | Cl | $C_{19}H_{21}Cl_2NO_2$ | 366.10 | 366.0 |
| 5 | S | R | Me | H | Cl | H | H | $C_{20}H_{24}ClNO_2$ | 346.15 | 346.2 |

1. ((S)-3-[(R)-2-Benzyloxy-1-(2-chlorophenoxy)ethyl] pyrrolidine
2. ((S)-3-[(R)-2-Benzyloxy-1-(2,3-dichlorophenoxy)ethyl]pyrrolidine
3. ((S)-3-[(R)-2-Benzyloxy-1-(2,4-dichlorophenoxy)ethyl]pyrrolidine
4. ((S)-3-[(R)-2-Benzyloxy-1-(2,6-dichlorophenoxy)ethyl]pyrrolidine
5. ((S)-3-[(R)-2-Benzyloxy-1-(3-chloro-2-methylphenoxy)ethyl]pyrrolidine

Example 11

(S)-3-[(R)-2-Ethoxy-1-(naphthalen-1-yloxy)ethyl]
pyrrolidine

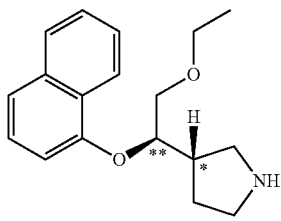 [SMILES: CCOC[C@H](Oc1cccc2ccccc12)[C@H]1CCNC1]

(S)-3-((R)-2-Ethoxy-1-hydroxyethyl)pyrrolidine-1-carboxylic acid t-butyl ester (200 mg, 0.8 mmol) and 1-fluoronaphthalene were dissolved in DMF (2.7 mL). NaH (27.8 mg, 1.2 mmol) was added and the mixture was stirred at room temperature for 15 minutes, then heated at 120° C. for 4 hours. The mixture was then cooled to room temperature. The mixture was concentrated then dissolved in 1.2M HCl in EtOH (19 mL, 23 mmol) and stirred overnight at room temperature. The product was concentrated and purified by preparative HPLC to yield the title compound as a mono-TFA salt (125 mg, 94% purity). MS m/z: [M+H]$^+$ calcd for $C_{18}H_{23}NO_2$, 286.17. found 286.2.

Preparation 8

4-Tetrahydropyranmagnesium Chloride

4-Chlorotetrahydropyran (650 μL, 6.0 mmol) was dissolved in THF (6 mL). Magnesium turnings (2.0 g, 80.7 mmol) was added to the mixture followed by methyl iodide (14 μL, 230 μmol). The mixture was stirred at 30° C. for 10 minutes and additional 4-chlorotetrahydropyran (9.3 g, 77 mmol) diluted in THF (60 mL) was added dropwise. 2.0M Isopropylmagnesium chloride in THF (2.0 mL) was added and the mixture was stirred overnight at 30° C. The mixture was cooled to room temperature to give a grey slurry of ~0.8M 4-tetrahydropyranmagnesium chloride in THF.

Preparation 9

(R)-3-[(S)—Hydroxy(tetrahydropyran-4-yl)methyl]pyrrolidine-1-carboxylic Acid t-Butyl Ester To a solution of (R)-3-hydroxymethyl-pyrrolidine-1-carboxylic acid t-butyl ester (20.0 g, 99.4 mmol) in DCM (200 mL, 3100 mmol) was added TEMPO ((310 mg, 2.0 mmol) and potassium bromide (590 mg, 5.0 mmol). This mixture was cooled at 0° C. and a 1:1 mixture of 0.7 M NaOCl in water (140 mL) and saturated aqueous NaHCO$_3$ solution (140 ml) was added dropwise over a period of 30 minutes. The resultant mixture was extracted with DCM (200 mL). The combined organic layers were washed with water (2×200 mL) and saturated aqueous NaCl (1×200 mL). The organic layer was dried over anhydrous Na$_2$SO$_4$, filtered and concentrated in vacuo to yield the title compound as an oil (15.5 g), which was used without further purification.

$^1$H-NMR (400 MHz, CDCl$_3$): δ (ppm)=9.68 (d, J=1.6 Hz, 1H), 3.76-3.60 (m, 1H), 3.58-3.44 (m, 1H), 3.44-3.28 (m, 2H), 3.08-2.96 (m, 1H), 2.28-2.00 (m, 2H), 1.45 (s, 9H).

A 0.8M solution of 4-tetrahydropyranmagnesium chloride in THF (37.6 mL) was cooled at 0° C. (R)-3-Formylpyrrolidine-1-carboxylic acid t-butyl ester (4.0 g, 20 mmol) in THF (40 mL) was added dropwise and the resulting mixture was allowed to warm to room temperature slowly overnight. The reaction was quenched by the addition of saturated aqueous NH$_4$Cl (50 mL) dropwise. The THF was removed in vacuo and the resulting solution was extracted with EtOAc (3×100 mL). The organic layer was washed with saturated aqueous NaCl (50 mL). The organic layer was collected, dried over Na$_2$SO$_4$, filtered, and concentrated. The crude product was purified by preparative HPLC (20-50%, c18 column packing material, 60 minutes) to give the separated isomers as clear oils:

(R)-3-[(R)-hydroxy(tetrahydropyran-4-yl)methyl]pyrrolidine-1-carboxylic acid t-butyl ester (1.4 g; 1$^{st}$ peak). $^1$H-NMR (400 MHz, DMSO): δ (ppm)=5.00-4.60 (br, 1H), 3.90-3.80 (m, 2H), 3.40-3.30 (m, 1H), 3.30-3.20 (m, 3H), 3.15-3.05 (m, 2H), 3.00-2.85 (m, 1H), 2.30-2.15 (m, 1H), 1.90-1.75 (m, 1H), 1.75-1.55 (m, 2H), 1.45-1.20 (m, 13H).

(R)-3-[(S)-hydroxy(tetrahydropyran-4-yl)methyl]pyrrolidine-1-carboxylic acid t-butyl ester (1.8 g; 2$^{nd}$ peak). $^1$H-NMR (400 MHz, DMSO): δ (ppm)=3.90-3.80 (m, 2H), 3.40-3.30 (m, 2H), 3.30-3.20 (m, 2H), 3.20-3.05 (m, 2H), 3.05-2.90 (m, 1H), 2.30-2.15 (m, 1H), 1.80-1.70 (m, 1H), 1.70-1.50 (m, 2H), 1.5-1.20 (m, 13H).

Example 12

(R)-3-[(S)-(2,3-Dichlorophenoxy)(tetrahydropyran-4-yl)-methyl]pyrrolidine

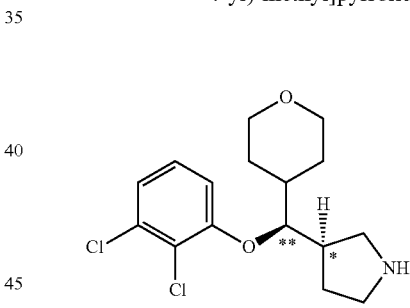

(R)-3-[(S)—Hydroxy(tetrahydropyran-4-yl)methyl]pyrrolidine-1-carboxylic acid t-butyl ester (30 mg, 0.1 mmol) was dissolved in DMF (380 μL). NaH (3.0 mg, 126 μmol) was added and the mixture was stirred at room temperature for 15 minutes. 1,2-Dichloro-3-fluorobenzene (34.7 mg, 210 μmol) was added and the mixture was stirred at 100° C. overnight. The mixture was concentrated then dissolved in 1.2M HCl in EtOH (510 μL, 610 μmol) and stirred overnight. The product was concentrated and purified by preparative HPLC to yield the title compound as a mono-TFA salt (10.8 mg, purity 100%). MS m/z: [M+H]$^+$ calcd for $C_{16}H_{21}Cl_2NO_2$, 330.10. found 330.0.

Example 13

Following the procedures described in the examples above, and substituting the appropriate starting materials and reagents, compounds 13-1 to 13-30, having formula IXa, were also prepared as mono-TFA salts:

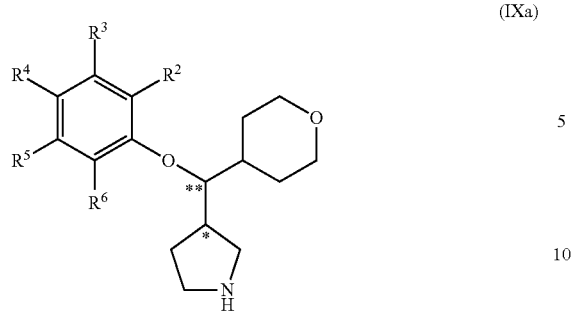

(IXa)

|  |  |  |  |  |  |  |  | MS m/z: [M + H]+ | |
|---|---|---|---|---|---|---|---|---|---|
| Ex. | * | ** | R² | R³ | R⁴ | R⁵ | R⁶ | Formula | calcd | found |
| 1 | S | S | Cl | H | H | H | H | $C_{16}H_{22}ClNO_2$ | 296.13 | 296.0 |
| 2 | R | R | Cl | H | H | H | H | $C_{16}H_{22}ClNO_2$ | 296.13 | 296.0 |
| 3 | R | S | Cl | H | H | H | H | $C_{16}H_{22}ClNO_2$ | 296.13 | 296.0 |
| 4 | S | R | Cl | H | H | H | H | $C_{16}H_{22}ClNO_2$ | 296.13 | 296.0 |
| 5 | R | S | H | F | H | H | H | $C_{16}H_{22}FNO_2$ | 280.16 | 280.2 |
| 6 | R | R | H | F | H | H | H | $C_{16}H_{22}FNO_2$ | 280.16 | 280.2 |
| 7 | R | R | H | —CF₃ | H | H | H | $C_{17}H_{22}F_3NO_2$ | 330.16 | 330.2 |
| 8 | S | S | H | —CF₃ | H | H | H | $C_{17}H_{22}F_3NO_2$ | 330.16 | 330.2 |
| 9 | R | R | H | H | Cl | H | H | $C_{16}H_{22}ClNO_2$ | 296.13 | 296.0 |
| 10 | R | R | H | H | F | H | H | $C_{16}H_{22}FNO_2$ | 280.16 | 280.2 |
| 11 | S | S | H | H | —CF₃ | H | H | $C_{17}H_{22}F_3NO_2$ | 330.16 | 330.2 |
| 12 | S | R | Cl | Cl | H | H | H | $C_{16}H_{21}Cl_2NO_2$ | 330.10 | 330.0 |
| 13 | R | R | Cl | Cl | H | H | H | $C_{16}H_{21}Cl_2NO_2$ | 330.10 | 330.0 |
| 14 | S | S | Cl | F | H | H | H | $C_{16}H_{21}ClFNO_2$ | 314.12 | 314.0 |
| 15 | S | R | Cl | F | H | H | H | $C_{16}H_{21}ClFNO_2$ | 314.12 | 314.0 |
| 16 | R | R | Cl | F | H | H | H | $C_{16}H_{21}ClFNO_2$ | 314.12 | 314.0 |
| 17 | R | S | Cl | F | H | H | H | $C_{16}H_{21}ClFNO_2$ | 314.12 | 314.0 |
| 18 | S | S | —CF₃ | Cl | H | H | H | $C_{17}H_{21}ClF_3NO_2$ | 364.12 | 364.0 |
| 19 | S | R | —CF₃ | Cl | H | H | H | $C_{17}H_{21}ClF_3NO_2$ | 364.12 | 364.0 |
| 20 | R | R | —CF₃ | Cl | H | H | H | $C_{17}H_{21}ClF_3NO_2$ | 364.12 | 364.0 |
| 21 | R | S | —CF₃ | Cl | H | H | H | $C_{17}H_{21}ClF_3NO_2$ | 364.12 | 364.0 |
| 22 | S | S | Cl | H | F | H | H | $C_{16}H_{21}Cl_2NO_2$ | 330.10 | 330.0 |
| 23 | R | R | —CF₃ | H | Cl | H | H | $C_{17}H_{21}ClF_3NO_2$ | 364.12 | 364.0 |
| 24 | S | S | Cl | H | H | H | Cl | $C_{16}H_{21}Cl_2NO_2$ | 330.10 | 330.0 |
| 25 | S | R | Cl | H | H | H | Cl | $C_{16}H_{21}Cl_2NO_2$ | 330.10 | 330.0 |
| 26 | R | R | Cl | H | H | H | Cl | $C_{16}H_{21}Cl_2NO_2$ | 330.10 | 330.0 |
| 27 | R | S | Cl | H | H | H | Cl | $C_{16}H_{21}Cl_2NO_2$ | 330.10 | 330.0 |
| 28 | S | S | H | Cl | H | Cl | H | $C_{16}H_{21}Cl_2NO_2$ | 330.10 | 330.0 |
| 29 | R | R | H | Cl | H | Cl | H | $C_{16}H_{21}Cl_2NO_2$ | 330.10 | 330.0 |
| 30 | R | S | H | Cl | H | Cl | H | $C_{16}H_{21}Cl_2NO_2$ | 330.10 | 330.0 |

1. (S)-3-[(S)-(2-Chlorophenoxy)(tetrahydropyran-4-yl)methyl]pyrrolidine
2. (R)-3-[(R)-(2-Chlorophenoxy)(tetrahydropyran-4-yl)methyl]pyrrolidine
3. (R)-3-[(S)-(2-Chlorophenoxy)(tetrahydropyran-4-yl) methyl]pyrrolidine
4. (S)-3-[(R)-(2-Chlorophenoxy)(tetrahydropyran-4-yl)methyl]pyrrolidine
5. (R)-3-[(S)-(3-Fluorophenoxy)(tetrahydropyran-4-yl)methyl]pyrrolidine
6. (R)-3-[(R)-(3-Fluorophenoxy)(tetrahydropyran-4-yl)methyl]pyrrolidine
7. (R)-3-[(R)-(Tetrahydropyran-4-yl)(3-trifluoromethylphenoxy)methyl]pyrrolidine
8. (S)-3-[(S)-(Tetrahydropyran-4-yl)(3-trifluoromethylphenoxy)methyl]pyrrolidine
9. (R)-3-[(R)-(4-Chlorophenoxy)(tetrahydropyran-4-yl)methyl]pyrrolidine
10. (R)-3-[(R)-(4-Fluorophenoxy)(tetrahydropyran-4-yl)methyl]pyrrolidine
11. (S)-3-[(S)-(Tetrahydropyran-4-yl)(4-trifluoromethylphenoxy)methyl]pyrrolidine
12. (S)-3-[(R)-(2,3-Dichlorophenoxy)(tetrahydropyran-4-yl)methyl]pyrrolidine
13. (R)-3-[(R)-(2,3-Dichlorophenoxy)(tetrahydropyran-4-yl)methyl]pyrrolidine
14. (S)-3-[(S)-(2-Chloro-3-fluorophenoxy)(tetrahydropyran-4-yl)methyl]pyrrolidine
15. (S)-3-[(R)-(2-Chloro-3-fluorophenoxy)(tetrahydropyran-4-yl)methyl]pyrrolidine
16. (R)-3-[(R)-(2-Chloro-3-fluoro-henoxy)(tetrahydropyran-4-yl)methyl]pyrrolidine
17. (R)-3-[(S)-(2-Chloro-3-fluorophenoxy)(tetrahydropyran-4-yl)methyl]pyrrolidine
18. (S)-3-[(S)-(3-Chloro-2-trifluoromethylphenoxy)(tetrahydropyran-4-yl)-methyl]-pyrrolidine
19. (S)-3-[(R)-(3-Chloro-2-trifluoromethylphenoxy)(tetrahydropyran-4-yl)-methyl]-pyrrolidine
20. (R)-3-[(R)-(3-Chloro-2-trifluoromethylphenoxy)(tetrahydropyran-4-yl)-methyl]-pyrrolidine
21. (R)-3-[(S)-(3-Chloro-2-trifluoromethylphenoxy)(tetrahydro-pyran-4-yl)-methyl]-pyrrolidine
22. (S)-3-[(S)-(2,4-Dichlorophenoxy)(tetrahydropyran-4-yl)methyl]pyrrolidine
23. (R)-3-[(R)-(4-Chloro-2-trifluoromethylphenoxy)(tetrahydropyran-4-yl)methyl]pyrrolidine
24. (S)-3-[(S)-(2,6-Dichlorophenoxy)(tetrahydropyran-4-yl)methyl]pyrrolidine
25. (S)-3-[(R)-(2,6-Dichlorophenoxy)(tetrahydropyran-4-yl)methyl]pyrrolidine
26. (R)-3-[(R)-(2,6-Dichlorophenoxy)(tetrahydropyran-4-yl)methyl]pyrrolidine
27. (R)-3-[(S)-(2,6-Dichlorophenoxy)(tetrahydropyran-4-yl)methyl]pyrrolidine
28. (S)-3-[(S)-(3,5-Dichlorophenoxy)(tetrahydropyran-4-yl)methyl]pyrrolidine
29. (R)-3-[(R)-(3,5-Dichlorophenoxy)(tetrahydropyran-4-yl)methyl]pyrrolidine
30. (R)-3-[(S)-(3,5-Dichlorophenoxy)(tetrahydropyran-4-yl)methyl]pyrrolidine Preparation 10

(S)-3-((R)-1-Hydroxy-2-methylsulfanylethyl)pyrrolidine-1-carboxylic Acid t-Butyl Ester Sodium methyl mercaptide (296 mg, 4.2 mmol) was dissolved in THF (1.0 mL), and the mixture was stirred for 10 minutes at room temperature. (S)—(R)-3-Oxiranylpyrrolidine-1-carboxylic acid t-butyl ester (300 mg, 1.41 mmol) was dissolved in THF (0.4 mL) and added to the mixture. The resulting solution was placed in a microwave reactor for 30 minutes at 100° C., then cooled to room temperature. Hexanes (3×10 mL) was added, followed by water (10 mL). The organic layer was collected, dried over $Na_2SO_4$, filtered, and concentrated. The crude product was purified by column chromatography (0-100% EtOAc in hexanes) to yield the title compound as a clear oil (207 mg).

$^1$H-NMR (400 MHz, $CDCl_3$): δ (ppm)=3.65-3.28 (m, 3H), 3.25-3.07 (m, 2H), 2.94 (t, J=8.0, 1H), 2.58 (dd, J=4.0, 16.0, 1H), 2.40 (t, J=12.0, 1H), 2.27-2.10 (m, 1H), 2.10-1.90 (m, 4H), 1.84-1.65 (m, 1H), 1.36 (s, 9H).

Example 14

(S)-3-[(R)-1-(4-Chloro-2-methylphenoxy)-2-methylsulfanylethyl]pyrrolidine

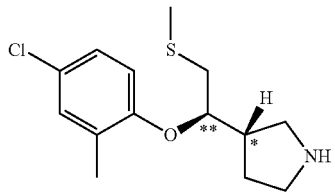 [SMILES: CSC[C@H](Oc1ccc(Cl)cc1C)[C@H]1CCNC1]

(S)-3-(R)-1-Hydroxy-2-methylsulfanylethyl)pyrrolidine-1-carboxylic acid t-butyl ester (20 mg, 80 μmol) was dissolved in DMF (367 μL). NaH (3.7 mg, 153 μmol) was added and the mixture was stirred at room temperature for 15 minutes. 5-Chloro-2-fluorotoluene (33.2 mg mg, 230 μmol) was added and the mixture was stirred at 100° C. for 1 hour. The mixture was cooled to room temperature, concentrated then dissolved in 1.2M HCl in EtOH (2.2 mL, 2.7 mmol) and stirred overnight at room temperature. The product was concentrated and purified by preparative HPLC to yield the title compound as a mono-TFA salt (0.6 mg, purity 85%). MS m/z: $[M+H]^+$ calcd for $C_{14}H_{20}ClNOS$, 286.10. found 286.0.

Example 15

Following the procedures described in the examples above, and substituting the appropriate starting materials and reagents, compounds 15-1 to 15-14, having formula IVa, were prepared as mono-TFA salts:

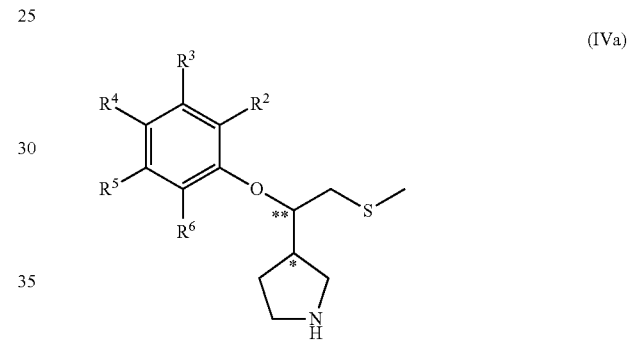

(IVa)

| Ex. | * | ** | $R^2$ | $R^3$ | $R^4$ | $R^5$ | $R^6$ | Formula | MS m/z: $[M + H]^+$ calcd | found |
|---|---|---|---|---|---|---|---|---|---|---|
| 1 | S | R | Cl | Cl | H | H | H | $C_{13}H_{17}Cl_2NOS$ | 306.04 | 306.0 |
| 2 | S | S | Cl | Cl | H | H | H | $C_{13}H_{17}Cl_2NOS$ | 306.04 | 306.0 |
| 3 | S | R | Cl | F | H | H | H | $C_{13}H_{17}ClFNOS$ | 290.07 | 290.0 |
| 4 | S | S | Cl | F | H | H | H | $C_{13}H_{17}ClFNOS$ | 290.07 | 290.0 |
| 5 | S | R | Me | Cl | H | H | H | $C_{14}H_{20}ClNOS$ | 286.10 | 286.0 |
| 6 | S | S | Me | Cl | H | H | H | $C_{14}H_{20}ClNOS$ | 286.10 | 286.0 |
| 7 | S | R | —$CF_3$ | Cl | H | H | H | $C_{14}H_{17}ClF_3NOS$ | 340.07 | 340.0 |
| 8 | S | S | —$CF_3$ | Cl | H | H | H | $C_{14}H_{17}ClF_3NOS$ | 340.07 | 340.0 |
| 9 | S | R | H | —$CF_3$ | H | H | H | $C_{14}H_{18}F_3NOS$ | 306.11 | 306.0 |
| 10 | S | S | H | —$CF_3$ | H | H | H | $C_{14}H_{18}F_3NOS$ | 306.11 | 306.2 |
| 11 | S | R | Cl | H | Cl | H | H | $C_{13}H_{17}Cl_2NOS$ | 306.04 | 306.0 |
| 12 | S | S | Cl | H | Cl | H | H | $C_{13}H_{17}Cl_2NOS$ | 306.04 | 306.0 |
| 13 | S | S | Cl | H | Cl | H | Me | $C_{14}H_{19}Cl_2NOS$ | 320.06 | 320.3 |
| 14 | S | S | F | F | F | H | H | $C_{13}H_{16}F_3NOS$ | 292.09 | 292.2 |

1. (S)-3-[(R)-1-(2,3-Dichlorophenoxy)-2-methylsulfanylethyl]pyrrolidine
2. (S)-3-[(S)-1-(2,3-Dichlorophenoxy)-2-methylsulfanylethyl]pyrrolidine
3. (S)-3-[(R)-1-(2-Chloro-3-fluorophenoxy)-2-methylsulfanylethyl] pyrrolidine
4. (S)-3-[(S)-1-(2-Chloro-3-fluorophenoxy)-2-methylsulfanylethyl]pyrrolidine
5. (S)-3-[(R)-1-(3-Chloro-2-methylphenoxy)-2-methylsulfanylethyl]pyrrolidine
6. (S)-3-[(S)-1-(3-Chloro-2-methylphenoxy)-2-methylsulfanylethyl]pyrrolidine
7. (S)-3-[(R)-1-(3-Chloro-2-trifluoromethylphenoxy)-2-methylsulfanylethyl]-pyrrolidine
8. (S)-3-[(S)-1-(3-Chloro-2-trifluoromethylphenoxy)-2-methylsulfanylethyl]pyrrolidine
9. (S)-3-[(R)-2-Methylsulfanyl-1-(3-trifluoromethylphenoxy)ethyl]pyrrolidine
10. (S)-3-[(S)-2-Methylsulfanyl-1-(3-trifluoromethylphenoxy)ethyl]pyrrolidine
11. (S)-3-[(R)-1-(2,4-Dichlorophenoxy)-2-methylsulfanylethyl]pyrrolidine
12. (S)-3-[(S)-1-(2,4-Dichlorophenoxy)-2-methylsulfanylethyl]pyrrolidine
13. (S)-3-[(S)-1-(2,4-Dichloro-6-methylphenoxy)-2-methylsulfanylethyl]pyrrolidine
14. (S)-3-[(S)-2-Methylsulfanyl-1-(2,3,4-trifluorophenoxy)ethyl]pyrrolidine

Preparation 11

(S)-3-((R)-2-Ethylsulfanyl-1-hydroxyethyl)pyrrolidine-1-carboxylic Acid t-Butyl Ester Ethanethiol (312 µL, 4.2 mmol) was dissolved in THF (1.0 mL), and the mixture was cooled to 0° C. NaH (50.6 mg, 2.1 mmol) was slowly added in four portions and the mixture was stirred at room temperature for 10 minutes. (S)—(R)-3-Oxiranylpyrrolidine-1-carboxylic acid t-butyl ester (300 mg, 1.4 mmol) was dissolved in THF (0.4 mL) and added to the mixture. The resulting solution was placed in a microwave reactor for 30 minutes at 100° C., then cooled to room temperature. Hexanes (3×10 mL) was added, followed by water (10 mL). The organic layer was collected, dried over $Na_2SO_4$, filtered, and concentrated. The crude product was purified by column chromatography (0-100% EtOAc in hexanes) to yield the title compound as a clear oil (315 mg).

$^1$H-NMR (400 MHz, $CDCl_3$): δ (ppm)=3.58-3.32 (m, 3H), 3.32-3.15 (m, 2H), 2.97 (dd, J=4.0, 12.0, 1H), 2.70 (dd, J=4.0, 12.0, 1H), 2.56-2.37 (m, 3H), 2.30-2.10 (m, 1H), 2.10-1.96 (m, 1H), 1.84-1.68 (m, 1H), 1.38 (s, 9H), 1.21 (t, J=4.0, 3H).

Example 16

(S)-3-[(R)-1-(3-Chloro-2-trifluoromethylphenoxy)-2-ethylsulfanylethyl]-pyrrolidine

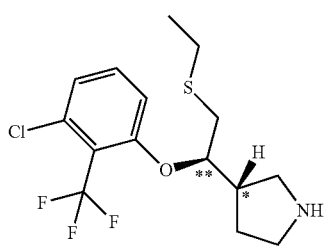 [SMILES: CCSC[C@H](Oc1cccc(Cl)c1C(F)(F)F)[C@H]1CCNC1]

(S)-3-((R)-2-Ethylsulfanyl-1-hydroxyethyl)pyrrolidine-1-carboxylic acid t-butyl ester (10 mg, 40 µmol) was dissolved in DMF (174 µL). NaH (1.3 mg, 54.5 µmol) was added and the mixture was stirred at room temperature for 15 minutes. 2-Chloro-6-fluorobenzotrifluoride (21.6 mg, 109 µmol) was added and the mixture was stirred at 100° C. for 1 hour. The mixture was cooled to room temperature, concentrated then dissolved in 1.2M HCl in EtOH (890 µL, 1.1 mmol) and stirred overnight at room temperature. The product was concentrated and the crude product was dissolved in 1:1 AcOH/$H_2O$ (1.5 mL) then purified by preparative HPLC to yield the title compound as a mono-TFA salt (3.4 mg, purity 97%). MS m/z: [M+H] calcd for $C_{15}H_{19}ClF_3NOS$, 354.08. found 354.0.

Example 17

Following the procedures described in the examples above, and substituting the appropriate starting materials and reagents, compounds 17-1 to 17-14, having formula IVb, were prepared as mono-TFA salts:

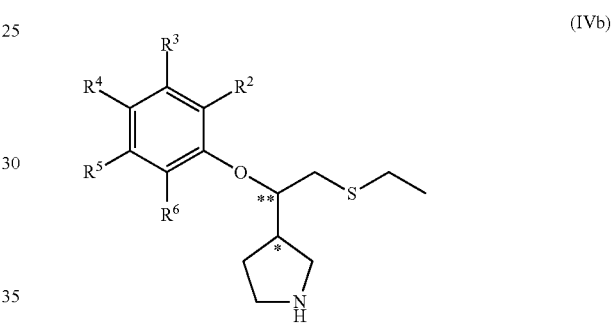

(IVb)

| Ex. | * | ** | $R^2$ | $R^3$ | $R^4$ | $R^5$ | $R^6$ | Formula | MS m/z: [M + H]$^+$ calcd | found |
|---|---|---|---|---|---|---|---|---|---|---|
| 1 | S | R | Cl | Cl | H | H | H | $C_{14}H_{19}Cl_2NOS$ | 320.06 | 320.0 |
| 2 | S | S | Cl | Cl | H | H | H | $C_{14}H_{19}Cl_2NOS$ | 320.06 | 320.0 |
| 3 | S | R | Cl | F | H | H | H | $C_{14}H_{19}ClFNOS$ | 304.09 | 304.0 |
| 4 | S | S | Cl | F | H | H | H | $C_{14}H_{19}ClFNOS$ | 304.09 | 304.2 |
| 5 | S | R | Me | Cl | H | H | H | $C_{15}H_{22}ClNOS$ | 300.11 | 300.2 |
| 6 | S | S | Me | Cl | H | H | H | $C_{15}H_{22}ClNOS$ | 300.11 | 300.0 |
| 7 | S | R | Cl | H | Cl | H | H | $C_{14}H_{19}Cl_2NOS$ | 320.06 | 320.0 |
| 8 | S | S | Cl | H | Cl | H | H | $C_{14}H_{19}Cl_2NOS$ | 320.06 | 320.0 |
| 9 | S | R | H | Cl | Cl | H | H | $C_{14}H_{19}Cl_2NOS$ | 320.06 | 320.0 |
| 10 | S | R | H | H | Cl | H | H | $C_{14}H_{20}ClNOS$ | 286.10 | 286.0 |
| 11 | S | R | H | H | —$CF_3$ | H | H | $C_{15}H_{20}F_3NOS$ | 320.12 | 320.2 |
| 12 | S | S | H | —$CF_3$ | H | H | H | $C_{15}H_{20}F_3NOS$ | 320.12 | 320.2 |
| 13 | S | R | —$CF_3$ | H | Cl | H | H | $C_{15}H_{19}ClF_3NOS$ | 354.08 | 354.0 |
| 14 | S | S | —$CF_3$ | Cl | H | H | H | $C_{15}H_{19}ClF_3NOS$ | 354.08 | 354.0 |

1. (S)-3-[(R)-1-(2,3-Dichlorophenoxy)-2-ethylsulfanylethyl]pyrrolidine
2. (S)-3-[(S)-1-(2,3-Dichlorophenoxy)-2-ethylsulfanylethyl]pyrrolidine
3. (S)-3-[(R)-1-(2-Chloro-3-fluorophenoxy)-2-ethylsulfanylethyl]pyrrolidine
4. (S)-3-[(S)-1-(2-Chloro-3-fluorophenoxy)-2-ethylsulfanylethyl]pyrrolidine
5. (S)-3-[(R)-1-(3-Chloro-2-methylphenoxy)-2-ethylsulfanylethyl]pyrrolidine
6. (S)-3-[(S)-1-(3-Chloro-2-methylphenoxy)-2-ethylsulfanylethyl]pyrrolidine
7. (S)-3-[(R)-1-(2,4-Dichlorophenoxy)-2-ethylsulfanylethyl]pyrrolidine
8. (S)-3-[(S)-1-(2,4-Dichlorophenoxy)-2-ethylsulfanylethyl]pyrrolidine
9. (S)-3-[(R)-1-(3,4-Dichlorophenoxy)-2-ethylsulfanyl-ethyl]pyrrolidine
10. (S)-3-[(R)-1-(4-Chlorophenoxy)-2-ethylsulfanylethyl]-pyrrolidine
11. (S)-3-[(R)-2-Ethylsulfanyl-1-(4-trifluoromethylphenoxy)ethyl]pyrrolidine
12. (S)-3-[(S)-2-Ethylsulfanyl-1-(3-trifluoromethylphenoxy)ethyl]pyrrolidine
13. (S)-3-[(R)-1-(4-Chloro-2-trifluoromethylphenoxy)-2-ethylsulfanylethyl]pyrrolidine
14. (S)-3-[(S)-1-(3-Chloro-2-trifluoromethylphenoxy)-2-ethylsulfanyethyl]pyrrolidine

Preparation 12

(S)-3-((R)-1-Hydroxy-2-isopropylsulfanylethyl) pyrrolidine-1-carboxylic Acid t-Butyl Ester 2-Propanethiol (98.0 μL, 1.1 mmol) was dissolved in THF (250 μL), and the mixture was cooled to 0° C. NaH (12.6 mg, 527 μmol) was slowly added in four portions and the mixture was stirred at room temperature for 10 minutes. (S)—(R)-3-Oxiranylpyrrolidine-1-carboxylic acid t-butyl ester (75 mg, 350 μmol) was dissolved in THF (0.1 mL) and added to the mixture. The resulting solution was placed in a microwave reactor for 30 minutes at 100° C., then cooled to room temperature. Hexanes (3×10 mL) was added, followed by water (10 mL). The organic layer was collected, dried over $Na_2SO_4$, filtered, and concentrated. The crude product was purified by column chromatography (0-100% EtOAc in hexanes) to yield the title compound as a clear oil (60 mg).

$^1$H-NMR (400 MHz, $CDCl_3$): δ (ppm)=3.58-3.30 (m, 3H), 3.27-3.10 (m, 1H), 2.95 (dd, J=4.0, 12.0, 1H), 2.90-2.78 (m, 2H), 2.72 (dd, J=4.0, 12.0, 1H), 2.47-2.35 (m, 1H), 2.26-2.10 (m, 1H), 2.10-1.93 (m, 1H), 1.80-1.65 (m, 1H), 1.34 (s, 9H), 1.30-1.10 (m, 6H).

Example 18

(S)-3-[(R)-1-(3-Chloro-2-trifluoromethylphenoxy)-2-isopropylsulfanylethyl]pyrrolidine

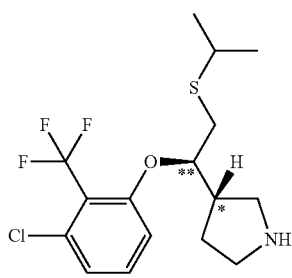 [SMILES: CC(C)SC[C@H](Oc1cccc(Cl)c1C(F)(F)F)[C@H]1CCNC1]

(S)-3-((R)-1-Hydroxy-2-isopropylsulfanylethyl)pyrrolidine-1-carboxylic acid t-butyl ester (10 mg, 0.030 μmol) was dissolved in DMF (166 μL). NaH (1.7 mg, 69.1 μmol) was added and the mixture was stirred at room temperature for 15 minutes. 2-Chloro-6-fluorobenzotrifluoride (20.6 mg, 104 μmol) was added and the mixture was stirred at 100° C. for 1 hour. The mixture was cooled to room temperature, concentrated then dissolved in 1.2M HCl in EtOH (1.0 mL, 1.2 mmol) and stirred overnight at room temperature. The product was concentrated and the crude product was dissolved in 1:1 AcOH/$H_2O$ (1.5 mL) then purified by preparative HPLC to yield the title compound as a mono-TFA salt (9.2 mg, purity 94%). MS m/z: [M+H] calcd for $C_{16}H_{21}ClF_3NOS$, 368.10. found 368.0.

Example 19

Following the procedures described in the examples above, and substituting the appropriate starting materials and reagents, compounds 19-1 to 19-7, having formula IVc, were prepared as mono-TFA salts:

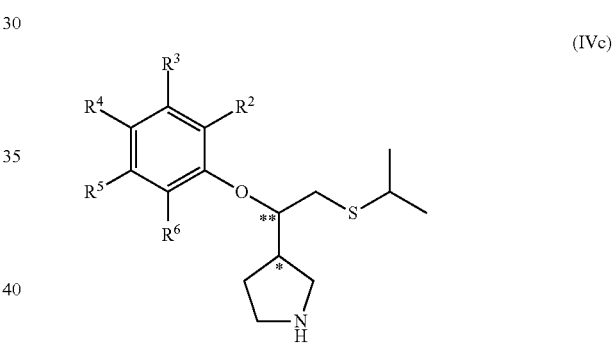

(IVc)

| Ex. | * | ** | $R^2$ | $R^3$ | $R^4$ | $R^5$ | $R^6$ | Formula | MS m/z: [M + H]$^+$ calcd | found |
|---|---|---|---|---|---|---|---|---|---|---|
| 1 | S | R | Cl | Cl | H | H | H | $C_{15}H_{21}Cl_2NOS$ | 334.07 | 334.0 |
| 2 | S | S | Cl | Cl | H | H | H | $C_{15}H_{21}Cl_2NOS$ | 334.07 | 334.0 |
| 3 | S | R | Cl | F | H | H | H | $C_{15}H_{21}ClFNOS$ | 318.10 | 318.0 |
| 4 | S | S | Cl | F | H | H | H | $C_{15}H_{21}ClFNOS$ | 318.10 | 318.2 |
| 5 | S | S | Cl | H | Cl | H | H | $C_{15}H_{21}Cl_2NOS$ | 334.07 | 334.0 |
| 6 | S | S | —$CF_3$ | Cl | H | H | H | $C_{16}H_{21}ClF_3NOS$ | 368.10 | 368.2 |
| 7 | S | R | H | Cl | Cl | H | H | $C_{15}H_{21}Cl_2NOS$ | 334.07 | 334.0 |

1. (S)-3-[(R)-1-(2,3-Dichlorophenoxy)-2-isopropylsulfanylethyl]pyrrolidine
2. (S)-3-[(S)-1-(2,3-Dichlorophenoxy)-2-isopropylsulfanylethyl]pyrrolidine
3. (S)-3-[(R)-1-(2-Chloro-3-fluorophenoxy)-2-isopropylsulfanylethyl]pyrrolidine
4. (S)-3-[(S)-1-(2-Chloro-3-fluorophenoxy)-2-isopropylsulfanylethyl]pyrrolidine
5. (S)-3-[(S)-1-(2,4-Dichlorophenoxy)-2-isopropylsulfanylethyl]pyrrolidine
6. (S)-3-[(S)-1-(3-Chloro-2-trifluoromethylphenoxy)-2-isopropylsulfanylethyl]pyrrolidine
7. (S)-3-[(R)-1-(3,4-Dichlorophenoxy)-2-isopropylsulfanylethyl]-pyrrolidine

Preparation 13

3-(1-Hydroxy-3-methylsulfanylpropyl)pyrrolidine-1-carboxylic Acid t-Butyl Ester 2-Oxopyrrolidine-1-carboxylic acid t-butyl ester (4.1 g, 22.0 mmol) was dissolved in THF (30 mL) under nitrogen, then cooled at −78° C. 2M Lithium diisopropylamide in heptane/THF/ethylbenzene (22.0 mL, 43.9 mmol) was added dropwise via syringe over 1 hour, and the resulting mixture was stirred for 1.5 hours at −78° C. 3-Methylthiopropionyl chloride (3.0 g, 22 mmol) was dissolved in THF (30 mL) and slowly added dropwise via syringe to the mixture over 1 hour, then stirred overnight at room temperature. The reaction was quenched with saturated aqueous $NH_4Cl$ (50 mL), and the mixture stirred at room temperature for 30 minutes. The mixture was extracted with EtOAc (200 mL). The organic layer was washed with saturated aqueous $NaHCO_3$ (2×75 mL), then saturated aqueous NaCl (2×75 mL). The aqueous layers were combined and re-extracted with EtOAc (75 mL). The organic layers were combined, dried over $Na_2SO_4$, filtered, and concentrated by rotary evaporation. The material was then placed on high vacuum for 10 minutes to yield a crude orange oil (7.0 g). The oil was purified by preparative HPLC (2×3.5 g crude; sample dissolved in 50% $AcOH/H_2O$; 2-50% $MeCN/H_2O$; 0.05% TFA; over 80 minutes on a 2" column at 40 mL/min). The fractions were collected as a white solid (606 mg) corresponding to the desired product, 3-(3-methylsulfanylpropionyl)-2-oxo-pyrrolidine-1-carboxylic acid t-butyl ester. LCMS m/z: [M+H] calcd for $C_{13}H_{21}NO_4S$, 287.37. found 288.4.

3-(3-Methylsulfanylpropionyl)-2-oxo-pyrrolidine-1-carboxylic acid t-butyl ester (188 mg, 654 μmol) was dissolved in THF (531 μL) under nitrogen. 2M $BH_3$-$Me_2S$ in THF (981 μL) was added via syringe over 15 minutes. The mixture was stirred at room temperature for 1 hour, then heated at 65° C. for 1 hours, then cooled to room temperature. The mixture was cooled on an ice bath and the reaction was slowly quenched with cold MeOH (100 mL). The mixture was stirred overnight and then diluted with EtOAc (30 mL) and washed with saturated aqueous $NaHCO_3$ (2×50 mL). The organic layer was dried over $Na_2SO_4$, filtered, and concentrated by rotary evaporation to yield a yellow oil (300 mg), which was used without further purification. LCMS m/z: $[M+H]^+$ calcd for $C_{13}H_{25}NO_3S$, 275.40. found 276.4.

Example 20

3-[1-(2,3-Dichlorophenoxy)-3-methylsulfanylpropyl]pyrrolidine

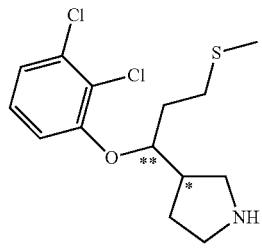 [SMILES: CSCCC(Oc1cccc(Cl)c1Cl)C1CCNC1]

3-(1-Hydroxy-3-methylsulfanylpropyl)pyrrolidine-1-carboxylic acid t-butyl ester (49 mg, 180 μmol) was dissolved in DMF (550 μL). 60% NaH in oil (60:40, NaH:mineral oil, 8.5 mg, 210 μmol) was slowly added, and the mixture was stirred for 15 minutes at room temperature. 1,2-Dichloro-3-fluorobenzene (62 μL, 530 μmol) was added, and the resulting mixture was heated at 90° C. for 24 hours. The reaction was quenched with MeOH, and DMF/MeOH was removed in vacuo. The product was dissolved in 1.25M HCl in EtOH (1.4 mL, 1.8 mmol) and stirred overnight at room temperature. The product was then purified by preparative HPLC to yield the title compound as a mixture of all 4 stereoisomers (R,R, R,S, S,S, and S,R) as mono-TFA salts (20 mg, 100% purity). MS m/z: [M+H] calcd for $C_{14}H_{19}Cl_2NOS$, 320.06. found 320.0.

Example 21

Following the procedures described in the examples above, and substituting the appropriate starting materials and reagents, compound 21-1, having formula IVd, was prepared as a mono-TFA salt:

(IVd)

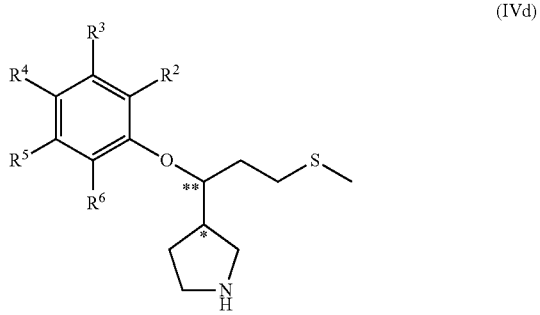

| # | * | ** | $R^2$ | $R^3$ | $R^4$ | $R^5$ | $R^6$ | Formula | MS m/z: $[M + H]^+$ calcd | found |
|---|---|----|-------|-------|-------|-------|-------|---------|-------|-------|
| 1 | mixture | | —$CF_3$ | H | Cl | H | H | $C_{15}H_{19}ClF_3NOS$ | 354.08 | 354.0 |

1. 3-[1-(4-Chloro-2-trifluoromethylphenoxy)-3-methylsulfanylpropyl]pyrrolidine

ASSAY 1 hSERT, hNET, and hDAT Binding Assays

Membrane radioligand binding assays were used to measure inhibition of labeled ligand ($^3$H-citalopram or $^3$H-nisoxetine or $^3$H-WIN35428) binding to membranes prepared from cells expressing the respective human recombinant transporter (hSERT or hNET or hDAT) in order to determine the $pK_i$ values of test compounds at the transporters.

Membrane Preparation From Cells Expressing hSERT, hNET, or hDAT

Recombinant human embryonic kidney (HEK-293) derived cell lines stably transfected with hSERT or hNET, respectively, were grown in DMEM medium supplemented with 10% dialyzed FBS (for hSERT) or FBS (for hNET), 100 µg/ml penicillin, 100 µg/ml streptomycin, 2 mM L-glutamine and 250 µg/ml of the aminoglycoside antibiotic G418, in a 5% $CO_2$ humidified incubator at 37° C. When cultures reached 80% confluence, the cells were washed thoroughly in PBS (without $Ca^{2+}$ and $Mg^{2+}$) and lifted with 5 mM EDTA in PBS. Cells were pelleted by centrifugation, resuspended in lysis buffer (10 mM Tris-HCl, pH 7.5 containing 1 mM EDTA), homogenized, pelleted by centrifugation, then resuspended in 50 mM Tris-HCl, pH 7.5 and 10% sucrose at 4° C. Protein concentration of the membrane suspension was determined using a Bio-Rad Bradford Protein Assay kit. Membranes were snap frozen and stored at −80° C. Chinese hamster ovary membranes expressing hDAT (CHO-DAT) were purchased from PerkinElmer and stored at −80° C.

Binding Assays

Binding assays were performed in a 96-well assay plate in a total volume of 200 µl assay buffer (50 mM Tris-HCl, 120 mM NaCl, 5 mM KCl, pH 7.4) with 0.5, 1, and 3 µg membrane protein, for SERT, NET and DAT, respectively. Saturation binding studies, to determine radioligand $K_d$ values for $^3$H-citalopram, $^3$H-nisoxetine, or $^3$H-WIN35428, respectively were conducted using 12 different radioligand concentrations ranging from 0.005-10 nM ($^3$H-citalopram); 0.01-20 nM ($^3$H-nisoxetine) and 0.2-50 nM ($^3$H-WIN35428). Inhibition assays for determination of $pK_i$ values of test compounds were conducted with 1.0 nM $^3$H-citalopram, 1.0 nM $^3$H-nisoxetine or 3.0 nM $^3$H-WIN35428, at 11 different concentrations of test compound ranging from 10 µM to 100 µM.

Stock solutions (10 mM in DMSO) of test compound were prepared and serial dilutions made using Dilution Buffer (50 mM Tris-HCl, 120 mM NaCl, 5 mM KCl, pH 7.4, 0.1% BSA, 400 µM ascorbic acid). Non-specific radioligand binding was determined in the presence of 1 µM duloxetine, 1 µM desipramine or 10 µM GBR12909 (each in Dilution Buffer) for the hSERT, hNET or hDAT assays, respectively.

Following a 60 minute incubation at 22° C. (or a period sufficient to reach equilibrium), the membranes were harvested by rapid filtration over a 96-well UniFilter GF/B plate, pretreated with 0.3% polyethyleneimine, and washed 6 times with 300 wash buffer (50 mM Tris-HCl, 0.9% NaCl, pH 7.5 at 4° C.). Plates were dried overnight at room temperature, approximately 45 µA of MicroScint™-20 (Perkin Elmer) added and bound radioactivity quantitated via liquid scintillation spectroscopy. Inhibition curves and saturation isotherms were analyzed using GraphPad Prism Software package (GraphPad Software, Inc., San Diego, Calif.). $IC_{50}$ values were generated from concentration response curves using the Sigmoidal Dose Response (variable slope) algorithm in Prism GraphPad. $K_d$ and $B_{max}$ values for the radioligand were generated from saturation isotherms using the Saturation Binding Global Fit algorithm in Prism GraphPad. $pK_i$ (negative decadic logarithm of $K_i$) values for test compounds were calculated from the best-fit $IC_{50}$ values, and the $K_d$ value of the radioligand, using the Cheng-Prusoff equation (Cheng & Prusoff (1973) *Biochem. Pharmacol.* 22(23):3099-3108): $K_i=IC_{50}/(1+[L]/K_d)$, where [L]=concentration radioligand.

Compounds of the invention that were tested in this assay, were found to exhibit the following SERT $pK_i$ and NET $pK_i$ values:

| Ex. | SERT $pK_i$ | NET $pK_i$ |
|---|---|---|
| Prep 3 | n.d. | n.d. |
| 1 | n.d. | n.d. |
| 2-1 | n.d. | n.d. |
| 2-2 | n.d. | n.d. |
| 3 | ≥8.0 | ≥8.0 |
| 4-1 | ≥7.0 | ≥7.0 |
| 4-2 | ≥7.0 | ≥8.0 |
| 4-3 | ≥7.0 | ≥7.0 |
| 4-4 | ≥8.0 | ≥7.0 |
| 4-5 | ≥8.0 | ≥8.0 |
| 4-6 | ≥8.0 | ≥8.0 |
| 4-7 | ≥8.0 | ≥8.0 |
| 4-8 | ≥8.0 | ≥7.0 |
| 4-9 | ≥8.0 | ≥8.0 |
| 4-10 | ≥8.0 | ≥8.0 |
| 4-11 | ≥7.0 | ≥7.0 |
| 4-12 | ≥7.0 | ≥8.0 |
| 4-13 | ≥8.0 | ≥8.0 |
| 4-14 | ≥8.0 | ≥7.0 |
| 4-15 | ≥8.0 | ≥8.0 |
| 4-16 | ≥8.0 | ≥8.0 |
| 4-17 | ≥8.0 | ≥7.0 |
| 4-18 | ≥8.0 | ≥8.0 |
| 4-19 | ≥7.0 | ≥7.0 |
| 4-20 | ≥8.0 | ≥8.0 |
| 4-21 | ≥8.0 | ≥8.0 |
| 4-22 | ≥8.0 | ≥7.0 |
| 4-23 | ≥8.0 | ≥7.0 |
| 4-24 | ≥7.0 | ≥7.0 |
| 4-25 | ≥8.0 | ≥8.0 |
| 4-26 | ≥8.0 | ≥8.0 |
| 4-27 | ≥7.0 | ≥7.0 |
| 4-28 | ≥7.0 | ≥8.0 |
| 4-29 | ≥8.0 | ≥7.0 |
| 4-30 | ≥8.0 | ≥7.0 |
| 5 (1$^{st}$ peak) | ≥8.0 | ≥7.0 |
| 5 (2$^{nd}$ peak) | ≥8.0 | ≥8.0 |
| 6 | n.d. | n.d. |
| 7-1 | n.d. | n.d. |
| 7-2 | n.d. | n.d. |
| 7-3 | n.d. | n.d. |
| 7-4 | n.d. | n.d. |
| 7-5 | n.d. | n.d. |
| 7-6 | n.d. | n.d. |
| 7-7 | n.d. | n.d. |
| 7-8 | ≥8.0 | ≥8.0 |
| 7-9 | n.d. | n.d. |
| 7-10 | n.d. | n.d. |
| 7-11 | n.d. | n.d. |
| 7-12 | n.d. | n.d. |
| 7-13 | n.d. | n.d. |
| 7-14 | n.d. | n.d. |
| 7-15 | n.d. | n.d. |
| 7-16 | n.d. | n.d. |
| 7-17 | n.d. | n.d. |
| 7-18 | n.d. | n.d. |
| 7-19 | n.d. | n.d. |
| 7-20 | n.d. | n.d. |
| 7-21 | n.d. | n.d. |
| 7-22 | n.d. | n.d. |
| 7-23 | n.d. | n.d. |
| 7-24 | n.d. | n.d. |

| Ex. | SERT pK$_i$ | NET pK$_i$ |
| --- | --- | --- |
| 7-25 | n.d. | n.d. |
| 7-26 | n.d. | n.d. |
| 7-27 | n.d. | n.d. |
| 7-28 | n.d. | n.d. |
| 7-29 | n.d. | n.d. |
| 7-30 | n.d. | n.d. |
| 7-31 | n.d. | n.d. |
| 7-32 | n.d. | n.d. |
| 8 | n.d. | n.d. |
| 9-1 | ≥7.0 | ≥6.0 |
| 9-2 | ≥7.0 | ≥5.0 |
| 9-3 | n.d. | n.d. |
| 9-4 | n.d. | n.d. |
| 9-5 | ≥8.0 | ≥8.0 |
| 9-6 | ≥8.0 | ≥7.0 |
| 9-7 | n.d. | n.d. |
| 9-8 | n.d. | n.d. |
| 9-9 | ≥8.0 | ≥7.0 |
| 9-10 | ≥7.0 | ≥7.0 |
| 9-11 | n.d. | n.d. |
| 9-12 | n.d. | n.d. |
| 9-13 | ≥8.0 | ≥8.0 |
| 9-14 | ≥8.0 | ≥7.0 |
| 9-15 | n.d. | n.d. |
| 9-16 | n.d. | n.d. |
| 9-17 | ≥8.0 | ≥7.0 |
| 9-18 | ≥8.0 | ≥7.0 |
| 9-19 | n.d. | n.d. |
| 9-20 | n.d. | n.d. |
| 9-21 | ≥8.0 | ≥7.0 |
| 9-22 | ≥8.0 | ≥6.0 |
| 9-23 | n.d. | n.d. |
| 9-24 | ≥8.0 | ≥7.0 |
| 9-25 | ≥8.0 | ≥7.0 |
| 9-26 | ≥7.0 | ≥7.0 |
| 9-27 | ≥6.0 | ≥6.0 |
| 9-28 | n.d. | n.d. |
| 9-29 | n.d. | n.d. |
| 10-1 | n.d. | n.d. |
| 10-2 | n.d. | n.d. |
| 10-3 | n.d. | n.d. |
| 10-4 | n.d. | n.d. |
| 10-5 | n.d. | n.d. |
| 11 | n.d. | n.d. |
| 12 | ≥8.0 | ≥8.0 |
| 13-1 | ≥7.0 | ≥8.0 |
| 13-2 | ≥7.0 | ≥8.0 |
| 13-3 | ≥8.0 | ≥8.0 |
| 13-4 | ≥8.0 | ≥7.0 |
| 13-5 | ≥7.0 | ≥7.0 |
| 13-6 | ≥7.0 | ≥8.0 |
| 13-7 | ≥7.0 | ≥7.0 |
| 13-8 | ≥7.0 | ≥7.0 |
| 13-9 | ≥8.0 | ≥8.0 |
| 13-10 | ≥7.0 | ≥7.0 |
| 13-11 | ≥8.0 | ≥7.0 |
| 13-12 | ≥8.0 | ≥8.0 |
| 13-13 | ≥8.0 | ≥8.0 |
| 13-14 | ≥8.0 | ≥8.0 |
| 13-15 | ≥8.0 | ≥8.0 |
| 13-16 | ≥8.0 | ≥8.0 |
| 13-17 | ≥8.0 | ≥8.0 |
| 13-18 | ≥8.0 | ≥7.0 |
| 13-19 | ≥8.0 | ≥7.0 |
| 13-20 | ≥8.0 | ≥8.0 |
| 13-21 | ≥8.0 | ≥7.0 |
| 13-22 | ≥7.0 | ≥8.0 |
| 13-23 | ≥8.0 | ≥7.0 |
| 13-24 | ≥8.0 | ≥8.0 |
| 13-25 | ≥7.0 | ≥7.0 |
| 13-26 | ≥7.0 | ≥8.0 |
| 13-27 | ≥7.0 | ≥8.0 |
| 13-28 | ≥8.0 | ≥7.0 |
| 13-29 | ≥8.0 | ≥8.0 |
| 13-30 | ≥8.0 | ≥8.0 |
| 14 | n.d. | n.d. |
| 15-1 | n.d. | n.d. |
| 15-2 | n.d. | n.d. |
| 15-3 | n.d. | n.d. |
| 15-4 | n.d. | n.d. |
| 15-5 | n.d. | n.d. |
| 15-6 | n.d. | n.d. |
| 15-7 | n.d. | n.d. |
| 15-8 | n.d. | n.d. |
| 15-9 | n.d. | n.d. |
| 15-10 | n.d. | n.d. |
| 15-11 | n.d. | n.d. |
| 15-12 | n.d. | n.d. |
| 15-13 | n.d. | n.d. |
| 15-14 | n.d. | n.d. |
| 16 | n.d. | n.d. |
| 17-1 | n.d. | n.d. |
| 17-2 | n.d. | n.d. |
| 17-3 | n.d. | n.d. |
| 17-4 | n.d. | n.d. |
| 17-5 | n.d. | n.d. |
| 17-6 | n.d. | n.d. |
| 17-7 | n.d. | n.d. |
| 17-8 | n.d. | n.d. |
| 17-9 | n.d. | n.d. |
| 17-10 | n.d. | n.d. |
| 17-11 | n.d. | n.d. |
| 17-12 | n.d. | n.d. |
| 17-13 | n.d. | n.d. |
| 17-14 | n.d. | n.d. |
| 18 | n.d. | n.d. |
| 19-1 | n.d. | n.d. |
| 19-2 | n.d. | n.d. |
| 19-3 | n.d. | n.d. |
| 19-4 | n.d. | n.d. |
| 19-5 | n.d. | n.d. |
| 19-6 | n.d. | n.d. |
| 19-7 | n.d. | n.d. |
| 20 | ≥8.0 | ≥8.0 |
| 21 | ≥8.0 | ≥7.0 | n.d. = not determined

ASSAY 2 hSERT, hNET and hDAT Neurotransmitter Uptake Assays

Neurotransmitter uptake assays were used to measure inhibition of $^3$H-serotonin ($^3$H-5-HT), $^3$H-norepinephrine ($^3$H-NE), and $^3$H-dopamine ($^3$H-DA) uptake into cells expressing the respective transporter (hSERT, hNET or hDAT) in order to determine the pIC$_{50}$ values of test compounds at the transporters.

$^3$H-5-HT, $^3$H-NE, and $^3$H-DA Uptake Assays

HEK-293 derived cell lines stably-transfected with hSERT, hNET, or hDAT, respectively, were grown in DMEM medium supplemented with 10% dialyzed FBS (for hSERT) or FBS (for hNET and hDAT), 100 µg/ml penicillin, 100 µg/ml streptomycin, 2 mM L-glutamine and 250 µg/ml of the aminoglycoside antibiotic G418 (for hSERT and hNET) or 800 ug/ml (for hDAT), in a 5% CO$_2$ humidified incubator at 37° C. When cultures reached 80% confluence, the cells were washed thoroughly in PBS (without Ca$^{2+}$ and Mg$^{2+}$) and lifted with 5 mM EDTA in PBS. Cells were harvested by centrifugation at 1100 rpm for 5 minutes, washed once by resuspension in PBS, then centrifuged. The supernatant was discarded and the cell pellet resuspended, by gentle trituration, in room temperature Krebs-Ringer bicarbonate buffer containing HEPES (10 mM), CaCl$_2$ (2.2 mM), ascorbic acid (200 µM) and pargyline (200 µM), pH 7.4. The final concentration of cells in the cell suspension was 7.5×10$^4$ cells/ml, 1.25×10$^5$ cells/ml, and 5.0×10$^4$ cells/ml for SERT, NET, and DAT cell lines, respectively.

Neurotransmitter uptake assays were performed in a 96-well assay plate in a total volume of 400 µl assay buffer (Krebs-Ringer bicarbonate buffer containing HEPES (10 mM), CaCl$_2$ (2.2 mM), ascorbic acid (200 µM) and pargyline (200 µM), pH 7.4) with 1.5×10$^4$ and 2.5×10$^4$ cells, for SERT, NET, and DAT, respectively. Inhibition assays for determination of pIC$_{50}$ values of test compounds were conducted with 11 different concentrations, ranging from 10 pM to 100 µM. Stock solutions (10 mM in DMSO) of test compound were prepared and serial dilutions prepared using 50 mM Tris-HCl, 120 mM NaCl, 5 mM KCl, pH 7.4, 0.1% BSA, 400 µM ascorbic acid. Test compounds were incubated for 30 minutes at 37° C. with the respective cells, prior to addition of radiolabeled neurotransmitter, $^3$H-5-HT (20 nM final concentration), $^3$H-NE (50 nM final concentration) or $^3$H-DA (100 nM final concentration). Non-specific neurotransmitter uptake was determined in the presence of 2.5 µM duloxetine, 2.5 µM desipramine, or 10 uM GBR-12909 (each in Dilution Buffer) for the hSERT, hNET, or hDAT assays, respectively.

Following a 10 minute incubation, at 37° C., with radioligand, the cells were harvested by rapid filtration over a 96-well UniFilter GF/B plate, pretreated with 1% BSA, and washed 6 times with 650 µl wash buffer (ice cold PBS). Plates were dried overnight at 37° C., ~45 µl of MicroScint™-20 (Perkin Elmer) added and incorporated radioactivity quantitated via liquid scintillation spectroscopy Inhibition curves were analyzed using GraphPad Prism Software package (GraphPad Software, Inc., San Diego, Calif.). IC$_{50}$ values were generated from concentration response curves using the Sigmoidal Dose Response (variable slope) algorithm in Prism GraphPad.

Compounds of the invention that were tested in this assay or in a fluorescence-based assay as described in Tsuruda et al. (2010) *Journal of Pharmacological and Toxicological Methods* 61(2):192-204 (data indicated by an asterisk in the table), were found to have serotonin and norepinephrine reuptake inhibition pIC$_{50}$ values as follows:

| Ex. | SERT pIC$_{50}$ | NET pIC$_{50}$ |
|---|---|---|
| Prep 3 | ≥8.0* | ≥8.0* |
| 1 | ≥8.0* | ≥8.0* |
| 2-1 | ≥7.0 | ≥7.0 |
| 2-2 | ≥7.0* | ≥8.0* |
| 3 | ≥8.0 | ≥8.0 |
| 4-1 | n.d. | n.d. |
| 4-2 | n.d. | n.d. |
| 4-3 | n.d. | n.d. |
| 4-4 | n.d. | n.d. |
| 4-5 | ≥7.0 | ≥8.0 |
| 4-6 | ≥7.0 | ≥8.0 |
| 4-7 | ≥8.0 | ≥8.0 |
| 4-8 | n.d. | n.d. |
| 4-9 | ≥8.0 | ≥8.0 |
| 4-10 | ≥8.0 | ≥8.0 |
| 4-11 | n.d. | n.d. |
| 4-12 | n.d. | n.d. |
| 4-13 | ≥7.0 | ≥7.0 |
| 4-14 | n.d. | n.d. |
| 4-15 | ≥7.0 | ≥8.0 |
| 4-16 | ≥8.0 | ≥8.0 |
| 4-17 | n.d. | n.d. |
| 4-18 | ≥7.0 | ≥8.0 |
| 4-19 | n.d. | n.d. |
| 4-20 | ≥7.0 | ≥8.0 |
| 4-21 | ≥7.0 | ≥8.0 |
| 4-22 | n.d. | n.d. |
| 4-23 | ≥8.0 | ≥7.0 |
| 4-24 | n.d. | n.d. |
| 4-25 | ≥8.0 | ≥8.0 |
| 4-26 | ≥7.0 | ≥8.0 |
| 4-27 | n.d. | n.d. |
| 4-28 | n.d. | n.d. |
| 4-29 | n.d. | n.d. |
| 4-30 | n.d. | n.d. |
| 5 (1$^{st}$ peak) | n.d. | n.d. |
| 5 (2$^{nd}$ peak) | ≥8.0 | ≥8.0 |
| 6 | ≥8.0* | ≥8.0* |
| 7-1 | ≥7.0* | ≥8.0* |
| 7-2 | ≥7.0* | ≥7.0* |
| 7-3 | ≥7.0* | ≥7.0* |
| 7-4 | ≥8.0* | ≥8.0* |
| 7-5 | ≥7.0* | ≥7.0* |
| 7-6 | ≥8.0* | ≥7.0* |
| 7-7 | ≥8.0* | ≥8.0* |
| 7-8 | ≥8.0 | ≥8.0 |
| 7-9 | ≥7.0* | ≥8.0* |
| 7-10 | ≥8.0* | ≥8.0* |
| 7-11 | ≥7.0* | ≥8.0* |
| 7-12 | ≥7.0* | ≥7.0* |
| 7-13 | ≥8.0* | ≥8.0* |
| 7-14 | ≥8.0* | ≥8.0* |
| 7-15 | ≥8.0* | ≥8.0* |
| 7-16 | ≥8.0* | ≥7.0* |
| 7-17 | ≥8.0* | ≥7.0* |
| 7-18 | ≥7.0* | ≥8.0* |
| 7-19 | ≥8.0* | ≥8.0* |
| 7-20 | ≥8.0* | ≥7.0* |
| 7-21 | ≥8.0* | ≥8.0* |
| 7-22 | ≥8.0* | ≥8.0* |
| 7-23 | ≥8.0* | ≥8.0* |
| 7-24 | ≥8.0* | ≥7.0* |
| 7-25 | ≥8.0* | ≥7.0* |
| 7-26 | ≥8.0* | ≥8.0* |
| 7-27 | ≥7.0* | ≥8.0* |
| 7-28 | ≥7.0* | ≥8.0* |
| 7-29 | ≥8.0* | ≥8.0* |
| 7-30 | ≥7.0* | ≥8.0* |
| 7-31 | ≥7.0* | ≥8.0* |
| 7-32 | ≥7.0* | ≥8.0* |
| 8 | ≥8.0* | ≥8.0* |
| 9-1 | ≥7.0* | ≥6.0* |
| 9-2 | ≥7.0* | ≥6.0* |
| 9-3 | ≥8.0* | ≥7.0* |
| 9-4 | ≥7.0* | ≥7.0* |
| 9-5 | ≥8.0* | ≥8.0* |
| 9-6 | ≥7.0* | ≥7.0* |
| 9-7 | ≥8.0* | ≥8.0* |
| 9-8 | ≥8.0* | ≥8.0* |
| 9-9 | ≥7.0* | ≥8.0* |
| 9-10 | ≥7.0* | ≥7.0* |
| 9-11 | ≥8.0* | ≥8.0* |
| 9-12 | ≥8.0* | ≥8.0* |
| 9-13 | ≥8.0* | ≥8.0* |
| 9-14 | ≥8.0* | ≥7.0* |
| 9-15 | ≥8.0* | ≥8.0* |
| 9-16 | ≥8.0* | ≥8.0* |
| 9-17 | ≥7.0* | ≥7.0* |
| 9-18 | ≥7.0* | ≥7.0* |
| 9-19 | ≥8.0* | ≥8.0* |
| 9-20 | ≥7.0* | ≥8.0* |
| 9-21 | ≥7.0* | ≥7.0* |
| 9-22 | ≥8.0* | ≥6.0* |
| 9-23 | ≥8.0* | ≥7.0* |
| 9-24 | ≥8.0* | ≥7.0* |
| 9-25 | ≥8.0* | ≥7.0* |
| 9-26 | ≥6.0* | ≥7.0* |
| 9-27 | ≥6.0* | ≥7.0* |
| 9-28 | ≥7.0* | ≥8.0* |
| 9-29 | ≥7.0* | ≥8.0* |

| Ex. | SERT pIC$_{50}$ | NET pIC$_{50}$ |
|---|---|---|
| 10-1 | ≥7.0* | ≥8.0* |
| 10-2 | ≥8.0* | ≥8.0* |
| 10-3 | ≥8.0* | ≥7.0* |
| 10-4 | ≥7.0* | ≥8.0* |
| 10-5 | ≥8.0* | ≥8.0* |
| 11 | ≥8.0 | ≥8.0 |
| 12 | ≥8.0 | ≥8.0 |
| 13-1 | ≥6.0 | ≥8.0 |
| 13-2 | n.d. | n.d. |
| 13-3 | ≥7.0 | ≥8.0 |
| 13-4 | ≥7.0 | ≥7.0 |
| 13-5 | n.d. | n.d. |
| 13-6 | n.d. | n.d. |
| 13-7 | n.d. | n.d. |
| 13-8 | n.d. | n.d. |
| 13-9 | ≥8.0 | ≥8.0 |
| 13-10 | n.d. | n.d. |
| 13-11 | ≥8.0* | ≥7.0* |
| 13-12 | ≥8.0 | ≥8.0 |
| 13-13 | ≥7.0 | ≥8.0 |
| 13-14 | ≥7.0 | ≥8.0 |
| 13-15 | ≥8.0 | ≥8.0 |
| 13-16 | ≥7.0 | ≥8.0 |
| 13-17 | ≥8.0 | ≥8.0 |
| 13-18 | n.d. | n.d. |
| 13-19 | n.d. | n.d. |
| 13-20 | ≥7.0 | ≥8.0 |
| 13-21 | n.d. | n.d. |
| 13-22 | ≥7.0 | ≥8.0 |
| 13-23 | n.d. | n.d. |
| 13-24 | ≥8.0 | ≥8.0 |
| 13-25 | n.d. | n.d. |
| 13-26 | n.d. | n.d. |
| 13-27 | n.d. | n.d. |
| 13-28 | n.d. | n.d. |
| 13-29 | ≥7.0 | ≥7.0 |
| 13-30 | ≥8.0 | ≥8.0 |
| 14 | ≥8.0* | ≥8.0* |
| 15-1 | ≥8.0* | ≥8.0* |
| 15-2 | ≥8.0* | ≥8.0* |
| 15-3 | ≥8.0* | ≥8.0* |
| 15-4 | ≥8.0* | ≥8.0* |
| 15-5 | ≥8.0* | ≥8.0* |
| 15-6 | ≥8.0* | ≥8.0* |
| 15-7 | ≥8.0* | ≥8.0* |
| 15-8 | ≥8.0* | ≥7.0* |
| 15-9 | ≥7.0* | ≥7.0* |
| 15-10 | ≥7.0* | ≥7.0* |
| 15-11 | ≥8.0* | ≥8.0* |
| 15-12 | ≥8.0* | ≥7.0* |
| 15-13 | ≥8.0* | ≥7.0* |
| 15-14 | ≥7.0* | ≥8.0* |
| 16 | ≥8.0* | ≥8.0* |
| 17-1 | ≥8.0* | ≥8.0* |
| 17-2 | ≥8.0* | ≥8.0* |
| 17-3 | ≥8.0* | ≥8.0* |
| 17-4 | ≥8.0* | ≥8.0* |
| 17-5 | ≥8.0* | ≥8.0* |
| 17-6 | ≥8.0* | ≥8.0* |
| 17-7 | ≥8.0* | ≥8.0* |
| 17-8 | ≥8.0* | ≥8.0* |
| 17-9 | ≥8.0* | ≥8.0* |
| 17-10 | ≥8.0* | ≥8.0* |
| 17-11 | ≥8.0* | ≥8.0* |
| 17-12 | ≥8.0* | ≥7.0* |
| 17-13 | ≥8.0* | ≥8.0* |
| 17-14 | ≥8.0* | ≥7.0* |
| 18 | ≥8.0* | ≥8.0* |
| 19-1 | ≥8.0* | ≥8.0* |
| 19-2 | ≥8.0* | ≥8.0* |
| 19-3 | ≥8.0* | ≥8.0* |
| 19-4 | ≥8.0* | ≥8.0* |
| 19-5 | ≥8.0* | ≥7.0* |
| 19-6 | ≥8.0* | ≥8.0* |
| 19-7 | ≥8.0* | ≥8.0* |
| 20 | n.d. | n.d. |
| 21 | n.d. | n.d. | n.d. = not determined

ASSAY 3

Ex Vivo SERT and NET Transporter Occupancy Studies

Ex vivo radioligand binding and neurotransmitter uptake assays are used to determine the in vivo occupancy of SERT and NET, in selected brain regions, following in vivo administration (acute or chronic) of test compounds. Following administration of test compound (by intravenous, intraperitoneal, oral, subcutaneous or other route) at the appropriate dose (0.0001 to 100 mg/kg), rats (≥n=4 per group) are euthanized at specific time points (10 minutes to 48 hours) by decapitation and the brain dissected on ice. Relevant brain regions are dissected, frozen and stored at −80° C. until use.

Ex Vivo SERT and NET Radioligand Binding Assays

For ex vivo radioligand binding assays, the initial rates of association of SERT ($^3$H-citalopram), and NET- ($^3$H-nisoxetine) selective radioligands with rat brain crude homogenates, prepared from vehicle and test compound-treated animals, are monitored (see Hess et al. (2004) *J. Pharmacol. Exp. Ther.* 310(2):488-497). Crude brain tissue homogenates are prepared by homogenizing frozen tissue pieces in 0.15 ml (per mg wet weight) of 50 mM Tris-HCl, 120 mM NaCl, 5 mM KCl, pH 7.4 buffer. Radioligand association assays are performed in a 96-well assay plate in a total volume of 200 µl assay buffer (50 mM Tris-HCl, 120 mM NaCl, 5 mM KCl, 0.025% BSA, pH 7.4) with 650 µg wet weight tissue (equivalent to 25 µg protein). Homogenates are incubated for up to 5 minutes with $^3$H-citalopram (3 nM) and $^3$H-nisoxetine (5 nM), respectively, prior to termination of the assay by rapid filtration over a 96-well UniFilter GF/B plate, pretreated with 0.3% polyethyleneimine. Filters then are washed 6 times with 300 µl wash buffer (50 mM Tris-HCl, 0.9% NaCl, pH 7.4 at 4° C.). Non-specific radioligand binding is determined in the presence of 1 µM duloxetine, or 1 µM despiramine, for $^3$H-citalopram or $^3$H-nisoxetine, respectively. The plates are dried overnight at room temperature, ~45 µA of MicroScint™-20 (Perkin Elmer) is added and bound radioactivity quantitated via liquid scintillation spectroscopy. The initial rates of association of $^3$H-citalopram and $^3$H-nisoxetine are determined by linear regression using GraphPad Prism Software package (GraphPad Software, Inc., San Diego, Calif.). The average rate of radioligand association to brain tissue homogenates from vehicle-treated animals us determined. The % occupancy of test compounds then us determined using the following equation:

% occupancy=100×(1−(initial rate association for test compound-treated tissue/mean rate association for vehicle-treated tissue))

ED$_{50}$ values are determined by plotting the log 10 of the dose of the test compound against the % occupancy. ED$_{50}$ values are generated from concentration response curves using the Sigmoidal Dose Response (variable slope) algorithm in GraphPad Prism.

Ex Vivo SERT and NET Uptake Assays

Ex vivo neurotransmitter uptake assays, in which the uptake of $^3$H-5-HT or $^3$H-NE into rat brain crude homogenates, prepared from vehicle and test compound-treated animals, are used to measure in vivo SERT and NET transporter occupancy (see Wong et al. (1993) *Neuropsychopharmacology* 8(1):23-33). Crude brain tissue homogenates are prepared by homogenizing frozen tissue pieces in 0.5 ml (per mg wet weight) of 10 mM HEPES buffer pH 7.4, containing 0.32 M sucrose, 200 µM ascorbic acid and 200 µM pargyline, at 22° C. Neurotransmitter uptake assays are performed in a 96-well Axygen plate in a total volume of 350 µl assay buffer (Krebs-Ringer bicarbonate buffer with 10 mM HEPES, 2.2 mM CaCl$_2$, 200 µM ascorbic acid and 200 µM pargyline, pH 7.4) with 50 µg protein. Homogenates are incubated for 5 minutes at 37° C. with $^3$H-5-HT (20 nM) and $^3$H-NE (50 nM), respectively, prior to termination of the assay by rapid filtration over a 96-well UniFilter GF/B plate, pretreated with 1% BSA. Plates are washed 6 times with 650 µl wash buffer (ice cold PBS) and dried overnight at 37° C., prior to addition of ~45 µl of MicroScint™-20 (Perkin Elmer). Incorporated radioactivity is quantitated via liquid scintillation spectroscopy. Non-specific neurotransmitter uptake is determined in parallel assays in which tissue homogenates are incubated with $^3$H-5-HT (20 nM) or $^3$H-NE (50 nM) for 5 minutes at 4° C.

ASSAY 4

Other Assays

Other assays that are used to evaluate the pharmacological properties of test compounds include, but are not limited to, cold ligand binding kinetics assays (Motulsky and Mahan (1984) *Molecular Pharmacol.* 25(1):1-9) with membranes prepared from cells expressing hSERT or hNET; conventional membrane radioligand binding assays using radiolabeled, for example, tritiated, test compound; radioligand binding assays using native tissue from, for example rodent or human brain; neurotransmitter uptake assays using human or rodent platelets; neurotransmitter uptake assays using crude, or pure, synaptosome preparations from rodent brain.

ASSAY 5

Formalin Paw Test

Compounds are assessed for their ability to inhibit the behavioral response evoked by a 50 µl al injection of formalin (5%). A metal band is affixed to the left hind paw of male Sprague-Dawley rats (200-250 g) and each rat is conditioned to the band for 60 minutes within a plastic cylinder (15 cm diameter). Compounds are prepared in pharmaceutically acceptable vehicles and administered systemically (i.p., p.o.) at pre-designated times before formalin challenge. Spontaneous nociceptive behaviors consisting of flinching of the injected (banded) hind paw are counted continuously for 60 minutes using an automated nociception analyzer (UCSD Anesthesiology Research, San Diego, Calif.). Antinociceptive properties of test articles are determined by comparing the number of flinches in the vehicle and compound-treated rats (Yaksh T L et al., "An automated flinch detecting system for use in the formalin nociceptive bioassay" (2001) *J. Appl. Physiol.* 90(6):2386-2402).

ASSAY 6

Spinal Nerve Ligation Model

Compounds are assessed for their ability to reverse tactile allodynia (increased sensitivity to an innocuous mechanical stimulus) induced by nerve injury. Male Sprague-Dawley rats are surgically prepared as described in Kim and Chung "An experimental model for peripheral neuropathy produced by segmental spinal nerve ligation in the rat" (1992) *Pain* 50(3): 355-363. Mechanical sensitivity is determined as the 50% withdrawal response to innocuous mechanical stimuli (Chaplan et al., "Quantitative assessment of tactile allodynia in the rat paw" (1994) *J. Neurosci. Methods* 53(1):55-63) before and after nerve injury. One to four weeks post-surgery, compounds are prepared in pharmaceutically acceptable vehicles and administered systemically (i.p., p.o.). The degree of nerve injury-induced mechanical sensitivity before and after treatment serves as an index of the compounds' antinociceptive properties.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:
1. A method of treating a patient that is suffering from a disorder or disease that is treated by the inhibition of the serotonin and/or the norepinephrine transporter, comprising administering a therapeutically effective amount of a compound of formula I:

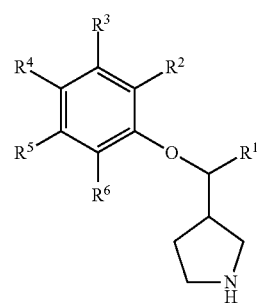

(I)

where:
R$^1$ is selected from —CH$_2$OH, —C$_{1-2}$alkylene-O—C$_{1-6}$alkyl, —C$_{1-2}$alkylene-S—C$_{1-6}$alkyl, —C$_{1-2}$alkylene-O-phenyl, —C$_{1-2}$alkylene-S-phenyl, —C$_{1-2}$alkylene-O-benzyl, —C$_{1-2}$alkylene-S-benzyl, tetrahydropyranyl, and tetrahydrofuranyl; and
R$^2$ through R$^6$ are independently selected from hydrogen, halo, —C$_{1-6}$alkyl, —CF$_3$, —O—C$_{1-6}$alkyl, —CN, —C(O)—C$_{1-6}$alkyl, —S—C$_{1-6}$alkyl, —C$_{3-8}$cycloalkyl, and —NO$_2$; or R$^4$ and R$^5$ are taken together to form —CH=CH—CH=CH—; or $R^5$ and $R^6$ are taken together to form —CH—CH=CH—CH—;

or a pharmaceutically acceptable salt thereof; wherein the disorder or disease is selected from a pain disorder, a depressive disorder, an affective disorder, attention deficit hyperactivity disorder, a cognitive disorder, stress urinary incontinence, chronic fatigue syndrome, obesity, and vasomotor symptoms associated with menopause.

2. The method of claim 1, wherein the pain disorder is neuropathic pain, fibromyalgia, or chronic pain.

3. The method of claim 1, wherein the disorder or disease is an attention deficit hyperactivity disorder.

4. The method of claim 1, where $R^1$ is —CH$_2$OH, —CH$_2$—O—CH$_3$, —(CH$_2$)$_2$—O—CH$_3$, —CH$_2$—O—CH$_2$CH$_3$, —CH$_2$—O—CH(CH$_3$)$_2$, —(CH$_2$)$_2$—S—CH$_3$, —CH$_2$—O-benzyl, or tetrahydropyranyl.

5. The method of claim 1, where $R^2$ is hydrogen, halo, —C$_{1-6}$alkyl, or —CF$_3$.

6. The method of claim 1, where $R^3$ is hydrogen, halo, or —CF$_3$.

7. The method of claim 1, where $R^4$ is hydrogen, halo, —C$_{1-6}$alkyl, —CF$_3$, or —CN.

8. The method of claim 1, where $R^5$ is hydrogen or halo.

9. The method of claim 1, where $R^6$ is hydrogen or halo.

10. The method of claim 1, where $R^5$ and $R^6$ are taken together to form —CH=CH—CH=CH—.

* * * * *